(12) United States Patent
Brenchley et al.

(10) Patent No.: US 8,957,078 B2
(45) Date of Patent: Feb. 17, 2015

(54) COMPOUNDS USEFUL AS INHIBITORS OF ATR KINASE

(71) Applicant: Vertex Pharmaceuticals Incorporated, Cambridge, MA (US)

(72) Inventors: Guy Brenchley, West Hanney (GB); Jean-Damien Charrier, Wantage (GB); Chris Davis, Salisbury (GB); Steven Durrant, Abingdon (GB); Gorka Etxebarria I Jardi, Abingdon (GB); Damien Fraysse, Abingdon (GB); Juan-Miguel Jimenez, Abingdon (GB); David Kay, Purton (GB); Ronald Knegtel, Abingdon (GB); Francoise Pierard, Abingdon (GB); Joanne Pinder, Didcot (GB); David Shaw, Oxford (GB); Pierre-Henri Storck, Abingdon (GB); John Studley, Witney (GB); Heather Twin, Wantage (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/098,640

(22) Filed: Dec. 6, 2013

(65) Prior Publication Data
US 2014/0275009 A1    Sep. 18, 2014

Related U.S. Application Data

(60) Provisional application No. 61/787,478, filed on Mar. 15, 2013.

(51) Int. Cl.
| C07D 487/04 | (2006.01) |
| A61K 31/437 | (2006.01) |
| C07D 453/02 | (2006.01) |
| C07D 471/08 | (2006.01) |
| C07D 491/107 | (2006.01) |

(52) U.S. Cl.
CPC ............ *C07D 487/04* (2013.01); *C07D 453/02* (2013.01); *C07D 471/08* (2013.01); *C07D 491/107* (2013.01)
USPC ........................................ 514/259.3; 544/281

(58) Field of Classification Search
USPC ...................................... 544/281; 514/259.31
See application file for complete search history.

(56) References Cited

U.S. PATENT DOCUMENTS

| 6,060,478 A | 5/2000 | Gilligan et al. |
| 6,191,131 B1 | 2/2001 | He et al. |
| 6,235,741 B1 | 5/2001 | Bilodeau et al. |
| 7,528,138 B2 | 5/2009 | Knegtel et al. |
| 7,550,470 B2 | 6/2009 | Fraley et al. |
| 2002/0041880 A1 | 4/2002 | DeFeo-Jones et al. |
| 2006/0156482 A1 | 7/2006 | Lim |
| 2009/0318436 A1 | 12/2009 | Albrecht et al. |
| 2012/0046295 A1 | 2/2012 | Charrier et al. |
| 2013/0017273 A1 | 1/2013 | Everitt et al. |
| 2013/0018035 A1 | 1/2013 | MacCormick et al. |
| 2013/0034616 A1 | 2/2013 | Storck et al. |

FOREIGN PATENT DOCUMENTS

| CN | 101537007 A | 9/2009 |
| CN | 103373996 | 10/2013 |
| CN | 101671336 | 11/2013 |
| JP | 2001302666 | 10/2001 |
| WO | WO9635690 A1 | 11/1996 |
| WO | WO9835110 A1 | 1/1998 |
| WO | WO9833799 A1 | 8/1998 |
| WO | WO9854093 A1 | 12/1998 |
| WO | WO0053605 A1 | 9/2000 |

(Continued)

OTHER PUBLICATIONS

S. Ahmed et al., "Synthesis of some Pyrazolopyrimidines as Purine Analogues", J. Heterocyclic Chem., 44, 803 (2007).

(Continued)

*Primary Examiner* — Bruck Kifle
(74) *Attorney, Agent, or Firm* — Rory C. Stewart

(57) ABSTRACT

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

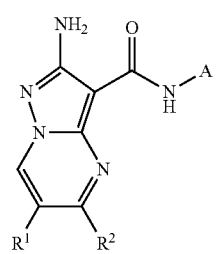

or a pharmaceutically acceptable salt, wherein the variables are as defined herein.

82 Claims, No Drawings

(56) References Cited

FOREIGN PATENT DOCUMENTS

| | | |
|---|---|---|
| WO | WO0140231 A1 | 6/2001 |
| WO | WO0192257 A1 | 12/2001 |
| WO | WO0240485 A2 | 5/2002 |
| WO | WO02066481 A1 | 8/2002 |
| WO | WO03000187 A2 | 1/2003 |
| WO | WO03037900 A2 | 5/2003 |
| WO | WO03101993 A2 | 12/2003 |
| WO | WO2004022559 A1 | 3/2004 |
| WO | WO2004022560 A1 | 3/2004 |
| WO | WO2004022561 A1 | 3/2004 |
| WO | WO2004026229 A2 | 4/2004 |
| WO | WO2004052315 A2 | 6/2004 |
| WO | WO2004076458 A1 | 9/2004 |
| WO | WO2005028434 A2 | 3/2005 |
| WO | WO2005051906 A2 | 6/2005 |
| WO | WO2005077954 A2 | 8/2005 |
| WO | WO2005080396 A2 | 9/2005 |
| WO | WO2005117909 A2 | 12/2005 |
| WO | WO2006052913 A1 | 5/2006 |
| WO | WO2006071752 A1 | 7/2006 |
| WO | WO2006087120 A2 | 8/2006 |
| WO | WO2006128184 A2 | 11/2006 |
| WO | WO2007041712 A1 | 4/2007 |
| WO | WO2007044401 A2 | 4/2007 |
| WO | WO2007044407 A2 | 4/2007 |
| WO | WO2007044410 A1 | 4/2007 |
| WO | WO2007044420 A2 | 4/2007 |
| WO | WO2007044426 A1 | 4/2007 |
| WO | WO2007044441 A2 | 4/2007 |
| WO | WO2007044449 A2 | 4/2007 |
| WO | WO2007046548 A1 | 4/2007 |
| WO | WO2007048066 A2 | 4/2007 |
| WO | WO2007126841 A2 | 11/2007 |
| WO | WO2007139732 A1 | 12/2007 |
| WO | WO2007139856 A2 | 12/2007 |
| WO | WO2007139860 A2 | 12/2007 |
| WO | WO2008004698 A2 | 1/2008 |
| WO | WO2008008539 A2 | 1/2008 |
| WO | WO2008045266 A2 | 4/2008 |
| WO | WO2008045268 A2 | 4/2008 |
| WO | WO2008063671 A2 | 5/2008 |
| WO | WO2008130569 A1 | 10/2008 |
| WO | WO2008130570 A1 | 10/2008 |
| WO | WO2008151735 A2 | 12/2008 |
| WO | WO2009006580 A1 | 1/2009 |
| WO | WO2009017954 A1 | 2/2009 |
| WO | WO2009070567 A1 | 6/2009 |
| WO | WO2009075790 A1 | 6/2009 |
| WO | WO2009088986 | 7/2009 |
| WO | WO2009091374 A2 | 7/2009 |
| WO | WO2009095254 A1 | 8/2009 |
| WO | WO2009117157 A1 | 9/2009 |
| WO | WO2010002483 A1 | 1/2010 |
| WO | WO2010006086 A2 | 1/2010 |
| WO | WO2010017047 A1 | 2/2010 |
| WO | WO2010034738 A2 | 4/2010 |
| WO | WO2010051549 A1 | 5/2010 |
| WO | WO2010059836 A1 | 5/2010 |
| WO | WO2010086040 A1 | 8/2010 |
| WO | WO2010091409 A1 | 8/2010 |
| WO | WO2011003065 A2 | 1/2011 |
| WO | WO2011022439 A1 | 2/2011 |
| WO | WO2011068667 A1 | 6/2011 |
| WO | WO2011121096 A1 | 6/2011 |
| WO | WO2011113606 A1 | 9/2011 |
| WO | WO2011163518 A1 | 12/2011 |
| WO | WO2012007375 A1 | 1/2012 |
| WO | WO2012022045 A1 | 2/2012 |
| WO | 2012/027236 A1 | 3/2012 |
| WO | WO2012067822 A1 | 5/2012 |
| WO | WO2012078855 A1 | 6/2012 |
| WO | WO2012143510 A1 | 10/2012 |
| WO | WO2012143796 A2 | 10/2012 |
| WO | WO2012177997 A1 | 12/2012 |
| WO | WO2013010136 A1 | 1/2013 |
| WO | WO2013010136 A1 | 1/2013 |
| WO | WO2013052263 A2 | 4/2013 |
| WO | WO2013138436 A1 | 10/2013 |
| WO | WO2013151930 A1 | 10/2013 |
| WO | WO2013151938 A1 | 10/2013 |
| WO | WO2013154878 | 10/2013 |
| WO | WO2013174930 A2 | 11/2013 |
| WO | WO2013174931 A1 | 11/2013 |
| WO | WO2014011911 A2 | 1/2014 |
| WO | WO2014015523 A1 | 1/2014 |
| WO | WO2014023691 A1 | 2/2014 |
| WO | WO2014025850 A1 | 2/2014 |
| WO | WO2014025852 A1 | 2/2014 |
| WO | WO2014025854 A1 | 2/2014 |
| WO | WO2014026984 A1 | 2/2014 |
| WO | WO2014029723 A1 | 2/2014 |
| WO | WO2014035140 A2 | 3/2014 |
| WO | WO2014039831 A1 | 3/2014 |
| WO | WO2014042433 A2 | 3/2014 |
| WO | WO2014044691 A1 | 3/2014 |
| WO | WO2014047648 A1 | 3/2014 |
| WO | WO2014066435 | 5/2014 |
| WO | WO2014066552 | 5/2014 |
| WO | WO2014089379 | 6/2014 |

OTHER PUBLICATIONS

O. Ahmed et al., "Synthesis and anti-tumor activities of some new pyridines and pyrazolo[1,5-a]pyrimidines", European Journal of Medicinal Chemistry 44 (2009) 3519-3523.

M. Elnagdi et al., "Synthesis of Substituted Azaindenes: Synthesis of New Pyrazolo[1,5-a]pyrimidine Derivatives", Bull. Chem. Soc. Jpn., 63, 1854-1856 (1990).

Y. Ho, "Studies on the Synthesis of New 3-(3,5-Diamino-1-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines", Journal of the Chinese Chemical Society, 1999, 46, 955-967.

A. Hussein, "Novel Synthesis of Some New Pyrimido[1,6-a]pyrimidine and Pyrazolo[1,5-a]pyrimidine Derivatives", J. Heterocyclic Chem., 49, 446, (2012).

International Search Report received in the corresponding PCT Application No. PCT/US/2005040344.

I. Otero et al., "Syntheses of Acyclo-C-nucleoside Analogs from 2,3:4,5-Di-O-isopropylidene-Di-O-isopropylidene-D-xylose", Journal of Carbohydrate Chemistry, 24:809-829, 2005.

I. Otero et al., "Synthesis of Iso-C-nucleoside Analogues from 1-(Methyl 2-O-benzyl]-4,6-O-benzylidene-3-deoxy-a-D-altropyranosid-3-yl)but-3-yn-2-ones", Z. Naturforsch. 60b, 1175-1185 (2005).

V. Ram et al., "Synthesis of bioisosteric pyrazolo[1,5-a]pyrimidines as leishmanicides", Indian Journal of Chemistry, vol. 34B, Jun. 1995, pp. 514-520.

V. Ried "Synthese neuer Heterocyclen ausgehend von Aminopyrazolen", Chemiker-Zeitung, 113. Jahrgang (1989) Nr. 5.

Non-Final Office Action dated Jun. 27, 2014 in U.S. Appl. No. 14/098,655.

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Ala Ser Glu Leu Pro Ala Ser Gln Pro Gln Pro Phe Ser Ala Lys Lys
1               5                   10                  15

Lys
```

COMPOUNDS USEFUL AS INHIBITORS OF ATR KINASE

CROSS-REFERENCE TO RELATED APPLICATIONS

The present application claims the benefit under 35 U.S.C. §119 of U.S. Provisional Application No. 61/787,478, filed Mar. 15, 2013.

SEQUENCE LISTING

The instant application contains a Sequence Listing in .txt format which has been submitted via EFS-Web and is hereby incorporated by reference in its entirety. The Sequence Listing, created on Jun. 2, 2014, is named VPI13107US.txt and is 924 bytes in size.

BACKGROUND OF THE INVENTION

ATR ("ATM and Rad3 related") kinase is a protein kinase involved in cellular responses to certain forms of DNA damage (e.g., double strand breaks and replication stress). ATR kinase acts with ATM ("ataxia telangiectasia mutated") kinase and many other proteins to regulate a cell's response to double strand DNA breaks and replication stress, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinases ATR and ATM. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of the invention are very potent ATR inhibitors. These compounds also show surprising synergy with other cancer agents, such as cisplatin and gemcitabine, in combination therapies.

DETAILED DESCRIPTION OF THE INVENTION

Another aspect of the invention provides a compound of Formula I:

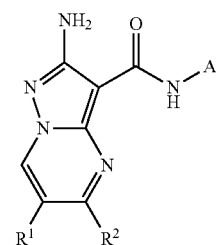

or a pharmaceutically acceptable salt or prodrug thereof, wherein:
$R^1$ and $R^2$ are independently selected from H; halo; —C($J^1$)$_2$CN; —CN; W; or M;
$J^1$ is independently selected from H or $C_{1-2}$alkyl; or two occurrences of $J^1$, together with the carbon atom to which they are attached, form an optionally substituted 3-4 membered carbocyclic ring;
M is a $C_{1-8}$aliphatic wherein up to three methylene units are optionally replaced with —O—, —NR—, —C(O)—, or —S(O)$_z$—, each M is optionally substituted with 0-3 occurrences of $R^{2a}$;
$R^{2a}$ is independently selected from halo; —CF$_3$; —CN; a $C_{1-4}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur;
W is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein W is optionally substituted with 0-5 occurrences of $J^W$;

$J^W$ is independently selected from —CN, halo, —CF$_3$; a C$_{1-4}$aliphatic wherein up to two methylene units are optionally replaced with —O—, —NR—, —C(O)—, or —S(O)$_z$—; or a 3-6 membered non-aromatic ring having 0-2 heteroatoms selected from oxygen, nitrogen, or sulfur;

two occurrences of $J^W$ on the same atom, together with atom to which they are joined, form a 3-6 membered ring having 0-2 heteroatoms selected from oxygen, nitrogen, or sulfur; or two occurrences of $J^W$, together with W, form a 6-10 membered saturated or partially unsaturated bridged ring system;

A is independently selected from:

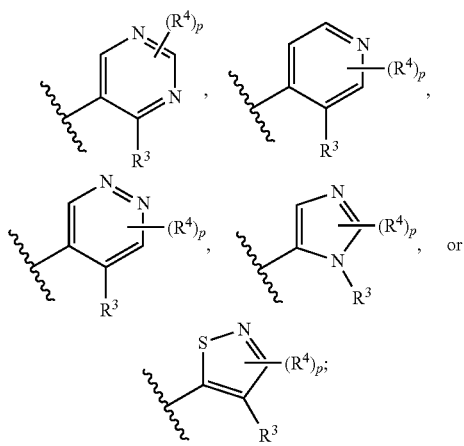

p is 0, 1, or 2;

R$^3$ is independently selected from -(L)$_n$-Q$^1$ or T;

L and T are each independently a C$_{1-10}$aliphatic chain wherein up to three methylene units of the aliphatic chain are optionally replaced with —O—, —NR—, —S(O)$_z$—, or —C(O)—; each L and T is independently substituted with 0-5 occurrences of $J^{LT}$;

$J^{LT}$ is independently selected from halo, —CN, or a C$_{1-4}$aliphatic chain wherein up to two methylene units of the aliphatic chain are optionally replaced with —O—, —NR—, —C(O)—, or —S(O)$_z$—;

n is 0 or 1;

Q$^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein Q$^1$ is independently substituted with 0-5 occurrences of $J^Q$;

$J^Q$ is independently selected from halo; —CN; ═O; Q$^2$; or a C$_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with Q$^1$, form a 6-10 membered saturated or partially unsaturated bridged ring system;

Q$^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^R$ is independently selected from halo; —CN; ═O; →O; Q$^3$; or a C$_{1-6}$aliphatic chain wherein up to two methylene units of the aliphatic chain are optionally replaced with —O—, —NR—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with Q$^2$, form a 6-10 membered saturated or partially unsaturated bridged ring system;

Q$^3$ is a 3-7 membered fully saturated, partially unsaturated, or aromatic monocyclic ring having 0-3 heteroatoms selected from oxygen, nitrogen, or sulfur; a 7-12 membered fully saturated, partially unsaturated, or aromatic bicyclic ring having 0-5 heteroatoms selected from oxygen, nitrogen, or sulfur;

$J^X$ is independently selected from halo or a C$_{1-4}$aliphatic chain wherein up to two methylene units of the aliphatic chain are optionally replaced with —O—, —NR—, —C(O)—, or —S(O)$_z$—; or $J^P$ is independently selected from halo; —CN; ═O; a C$_{1-6}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; each $J^P$ is optionally substituted with 0-3 occurrences of $J^M$; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with Q$^3$, form a 6-10 membered saturated or partially unsaturated bridged ring system;

R$^4$ is independently selected from H, halo, a C$_{3-4}$ membered cycloalkyl, 3-4 membered heterocyclyl, or C$_{1-4}$aliphatic chain wherein up to two methylene units of the aliphatic chain are optionally replaced with —O—, —NR—, —C(O)—, or —S(O)$_z$—;

$J^M$ is independently selected from halo or C$_{1-6}$aliphatic;

z is 0, 1, or 2; and

R is independently selected from H or C$_{1-4}$aliphatic.

Another aspect of the invention provides a compound of Formula I:

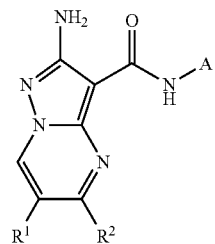

or a pharmaceutically acceptable salt or prodrug thereof, wherein:

R$^1$ is independently selected from H, fluoro, chloro, or —C(J$^1$)$_2$CN;

J$^1$ is independently selected from H or C$_{1-2}$alkyl; or two occurrences of $J^1$, together with the carbon atom to which they are attached, form an optionally substituted 3-4 membered carbocyclic ring;

$R^2$ is independently selected from H; halo; —CN; or a $C_{1-6}$aliphatic chain wherein up to two methylene units of the aliphatic chain are optionally replaced with —O—, —NR—, —C(O)—, or —S(O)$_z$—; each $R^2$ is optionally substituted with 0-3 occurrences of $R^{2a}$;

$R^{2a}$ is independently selected from halo, $C_{1-4}$alkyl, —CN, or a 3-6 membered non-aromatic ring having 0-2 heteroatoms selected from oxygen, nitrogen, or sulfur;

A is independently selected from:

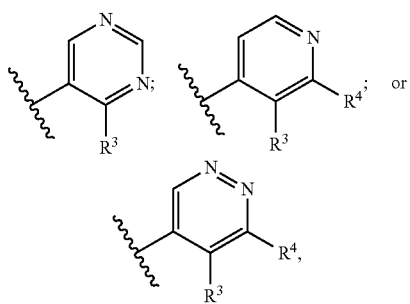

$R^3$ is independently selected from -(L)$_n$-Q$^1$ or T;

L and T are each independently a $C_{1-10}$aliphatic chain wherein up to three methylene units of the aliphatic chain are optionally replaced with —O—, —NR—, —S(O)$_z$—, or —C(O)—; each L and T is independently substituted with 0-5 occurrences of $J^{LT}$;

$J^{LT}$ is independently selected from halo, —CN, or a $C_{1-4}$aliphatic chain wherein up to two methylene units of the aliphatic chain are optionally replaced with —O—, —NR—, —C(O)—, or —S(O)$_z$—;

n is 0 or 1;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein $Q^1$ is independently substituted with 0-5 occurrences of $J^Q$;

$J^Q$ is independently selected from halo; —CN; =O; $Q^2$; or a $C_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^R$ is independently selected from halo; —CN; =O; →O; $Q^3$; or a $C_{1-6}$aliphatic chain wherein up to two methylene units of the aliphatic chain are optionally replaced with —O—, —NR—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; a 7-12 membered fully saturated, partially unsaturated, or aromatic bicyclic ring having 0-5 heteroatoms selected from oxygen, nitrogen, or sulfur;

$J^X$ is independently selected from halo or a $C_{1-4}$aliphatic chain wherein up to two methylene units of the aliphatic chain are optionally replaced with —O—, —NR—, —C(O)—, or —S(O)$_z$—; or $J^P$ is independently selected from halo; —CN; =O; a $C_{1-6}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with $Q^3$, form a 6-10 membered saturated or partially unsaturated bridged ring system;

$R^4$ is independently selected from H or $C_{1-3}$aliphatic;

z is 0, 1, or 2; and

R is independently selected from H or $C_{1-4}$aliphatic.

For purposes of this application, it will be understood that when two occurrences of $J^Q$, together with $Q^1$, form a bridged ring system, the two occurrences of $J^Q$ are attached to separate atoms of $Q^1$. Additionally, when two occurrences of $J^R$, together with $Q^2$, form a bridged ring system, the two occurrence of $J^R$ are attached to separate atoms of $Q^2$. Moreover, when two occurrences of $J^P$, together with $Q^3$, form a bridged ring system, the two occurrences of $J^P$ are attached to separate atoms of $Q^3$. Finally, when two occurrences of $J^W$, together with W, form a bridged ring system, the two occurrences of $J^W$ are attached to separate atoms of W;

In one embodiment, the present invention is a compound of formula I, wherein $R^1$ is fluoro. In another embodiment, the present invention is a compound of formula I, wherein $R^1$ is —CH$_2$CN or —CH(C$_{1-2}$alkyl)CN. In yet another embodiment, the present invention is a compound of formula I, wherein $R^1$ is chloro. In other embodiments, the present invention is a compound of formula I, wherein $R^1$ is H.

In some embodiments, the present invention is a compound of formula I, wherein $R^2$ is —CF$_3$. In another embodiment, the present invention is a compound of formula I, wherein $R^2$ is $C_{1-6}$aliphatic wherein up to two methylene units are optionally replaced with —O—, —NR—, —C(O)—, or S. In other embodiments, the present invention is a compound of formula I, wherein $R^2$ is —O(C$_{1-3}$alkyl)N(C$_{1-3}$alkyl) or —NR(C$_{1-3}$alkyl)N(C$_{1-3}$alkyl). In yet another embodiment, the present invention is a compound of formula I, wherein $R^2$ is H.

In some examples, the present invention is a compound of formula I, wherein A is:

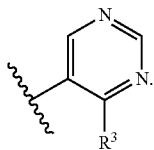

In other examples, the present invention is a compound of formula I, wherein A is:

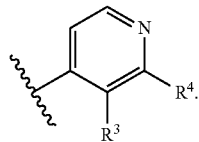

In yet further examples, the present invention is a compound of formula I, wherein
A is:

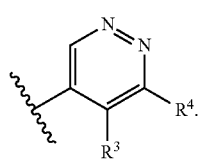

In one or more embodiments, the present invention is a compound of formula I, wherein $R^3$ is -(L)$_n$-Q$^1$. In another embodiment, the present invention is a compound of formula I, wherein $R^3$ is T.

In some embodiments, the present invention is a compound of formula I, wherein is 1. In other embodiments, the present invention is a compound of formula I, wherein n is 0.

In yet another example, the present invention is a compound of formula I, wherein L is —O—

In another aspect, the present invention is a compound of formula I, wherein $Q^1$ is independently selected from a 3-7 membered fully saturated, partially unsaturated, or aromatic monocyclic ring having 0-3 heteroatoms selected from oxygen, nitrogen, or sulfur. In other aspects, the present invention is a compound of formula I, wherein $Q^1$ is a 3-7 membered heterocyclyl or carbocyclyl. In yet another aspect, the present invention is a compound of formula I, wherein $Q^1$ is independently selected from cyclopropyl, cyclobutyl, cyclopentyl, cyclohexyl, cycloheptyl, pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, and azetidinyl. In some embodiments, the present invention is a compound of formula I, wherein $Q^1$ is independently selected from pyrrolidinyl, cyclopropyl, cyclohexyl, piperidinyl or piperazinyl.

In other embodiments, the present invention is a compound of formula I, wherein $Q^1$ is a 5-6 membered aryl or heteroaryl. In yet another embodiment, the present invention is a compound of formula I, wherein $Q^1$ is independently selected from phenyl, pyridinyl, pyrazinyl, pyrimidinyl, tetrahydropyridinyl, pyrrolyl, imidazolyl, pyrazolyl, 1,2,3-triazolyl, or 1,2,4-triazolyl. In further embodiments, the present invention is a compound of formula I, wherein $Q^1$ is pyridinyl.

In another example, the present invention is a compound of formula I, wherein $Q^1$ is a 7-12 membered fully saturated, partially unsaturated, or aromatic bicyclic ring having 1-5 heteroatoms selected from oxygen, nitrogen, or sulfur. In some examples, the present invention is a compound of formula I, wherein $Q^1$ is independently selected from octahydropyrrolo[1,2-a]pyrazinyl, 5,6,7,8-tetrahydroimidazo[1,2-a]pyridinyl, octahydro-1H-pyrazino[1,2-a]pyrazinyl, 5,6,7,8-tetrahydroimidazo[1,5-a]pyrazinyl, 2,5-diazabicyclo[4.1.0]heptane, or octahydropyrazino[2,1-a][1,4]oxazinyl.

In one or more aspects of the invention, the present invention is a compound of formula I, wherein $J^Q$ is $C_{1-6}$aliphatic chain wherein up to three methylene units of the aliphatic chain are optionally replaced with —O—, —NR—, or —C(O)—. In other aspects, the present invention is a compound of formula I, wherein $J^Q$ is independently selected from —C(O)—, $C_{1-4}$alkyl, —(C$_{0-4}$alkyl)NH$_2$, —(C$_{0-4}$alkyl)NH(C$_{1-4}$alkyl), —(C$_{0-4}$alkyl)N(C$_{1-4}$alkyl)$_2$, —(C$_{0-4}$alkyl)OH, —(C$_{0-4}$alkyl)O(C$_{1-4}$alkyl), —C(O)OH, —C(O)O(C$_{1-4}$alkyl), N(C$_{1-4}$alkyl)$_2$, —C(O)N(C$_{1-4}$alkyl)$_2$, or —(C$_{1-3}$alkyl)O(C$_{1-2}$alkyl)N(C$_{1-3}$alkyl)$_2$. In yet another aspect, the present invention is a compound of formula I, wherein $J^Q$ is independently selected from —C(O)—, $C_{1-4}$alkyl, or —(C$_{0-4}$alkyl)NH$_2$.

In some embodiments, the present invention is a compound of formula I, wherein $J^Q$ is $Q^2$. In another embodiment, the present invention is a compound of formula I, wherein $Q^2$ is a 3-7 membered fully saturated, partially unsaturated, or aromatic monocyclic ring having 0-3 heteroatoms selected from oxygen, sulfur, or nitrogen. In other embodiments, the present invention is a compound of formula I, wherein $Q^2$ is independently selected from selected from cyclopropyl, cyclobutyl, cyclopentyl, cyclohexyl, oxetanyl, tetrahydropyranyl, tetrahydrofuranyl, azetidinyl, pyrrolidinyl, piperidinyl, piperazinyl, thiomorpholinyl, or morpholinyl. In yet another embodiment, the present invention is a compound of formula I, wherein $Q^2$ is oxetanyl, pyrrolidinyl, tetrahydrofuranyl, or tetrahydropyranyl.

In one or more examples, the present invention is a compound of formula I, wherein $Q^2$ is a 7-12 membered fully saturated, partially unsaturated, or aromatic bicyclic ring having 0-5 heteroatoms selected from oxygen, nitrogen, or sulfur. In some examples, the present invention is a compound of formula I, wherein $Q^2$ is independently selected from 5,6,7,8-tetrahydroimidazo[1,5-a]pyrazinyl or 5,6,7,8-tetrahydroimidazo[1,2-a]pyrazinyl.

In another aspect, the present invention is a compound of formula I, wherein two occurrences of $J^Q$, together with $Q^1$, form a bridged ring system. In some aspects, the present invention is a compound of formula I, wherein two occurrences of $J^Q$ on the same atom, taken together with the atom to which they are joined, form a 3-6 membered non-aromatic ring having 0-2 heteroatoms selected from oxygen, nitrogen, or sulfur. In yet another aspect, the present invention is a compound of formula I, wherein the ring formed by the two occurrences of $J^Q$ on the same atom, taken together with the atom to which they are joined, is selected from oxetanyl, cyclobutyl, or azetidinyl.

In some embodiments, the present invention is a compound of formula I, wherein $J^R$ is a 3-6 membered heterocyclyl having 1-3 heteroatoms selected from oxygen, nitrogen, or sulfur. In another embodiment, the present invention is a compound of formula I, wherein $J^R$ is independently selected from oxetanyl, piperidinyl, azetidinyl, piperazinyl, pyrrolidinyl, 1,4-diazepanyl, or morpholinyl. In other embodiments, the present invention is a compound of formula I, wherein $J^R$ is a piperazinyl.

In yet another embodiment, the present invention is a compound of formula I, wherein $J^R$ is independently selected from halo, =O, —OH, $C_{1-4}$alkyl, —($C_{0-4}$alkyl)N($C_{1-4}$alkyl)$_2$, or —($C_{0-4}$alkyl)O($C_{1-4}$alkyl). In other embodiments, the present invention is a compound of formula I, wherein two occurrences of $J^R$ on the same atom, together with the atom to which they are joined, form a 3-6 membered aromatic or non-aromatic ring having 0-2 heteroatoms selected from oxygen, nitrogen, or sulfur.

In some aspects, the present invention is a compound of formula I, wherein $J^P$ is halo, —$C_{1-4}$alkyl, or a 3-6 membered non-aromatic ring having 0-2 heteroatoms selected from oxygen, nitrogen, or sulfur. In other aspects, the present invention is a compound of formula I, wherein $J^P$ is independently selected from pyrrolidinyl or oxetanyl.

In another aspect, the present invention is a compound of formula I, wherein T is independently selected from —($C_{1-4}$alkyl), —($C_{1-4}$alkyl)N($C_{1-4}$alkyl)$_2$, —($C_{1-3}$alkyl)O($C_{1-2}$alkyl)N($C_{1-3}$alkyl)$_2$, —($C_{1-4}$alkyl)OH, —($C_{1-4}$alkyl)NH$_2$, or —($C_{1-4}$alkyl)O($C_{1-4}$alkyl). In yet another aspect, the present invention is a compound of formula I, wherein $J^{LT}$ is halo or $C_{1-3}$alkyl.

In still other aspects, the present invention is a compound of formula I, wherein A is independently selected from:

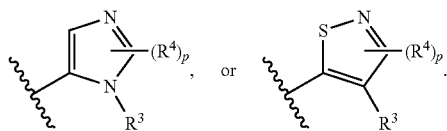

In some embodiments, the present invention is a compound of formula I, wherein p is 0. In other embodiments, the present invention is a compound of formula I, wherein p is 1.

In another embodiment, the present invention is a compound of formula I, wherein $R^4$ is independently selected from $C^{1-4}$alkyl or halo. In yet another embodiment, the present invention is a compound of formula I, wherein $R^4$ is independently selected from methyl or fluoro.

In some embodiments, the present invention is a compound of formula I, wherein $R^3$ is -(L)$_n$-$Q^1$.

In other embodiments, the present invention is a compound of formula I, wherein n is 0. In still other embodiments, the present invention is a compound of formula I, wherein n is 1.

In one or more aspects, the present invention is a compound of formula I, wherein L is independently selected from $C_{1-4}$alkyl.

In another embodiment, $Q^1$ the present invention is a compound of formula I, wherein is phenyl. In yet another embodiment, the present invention is a compound of formula I, wherein $Q^1$ is independently selected from a 3-6 membered carbocyclyl or a 4-6 membered heterocyclyl. In some embodiments, the present invention is a compound of formula I, wherein $Q^1$ is independently selected from cyclopropyl, morpholinyl, pyrrolidinyl, piperidinyl, piperazinyl, tetrahydropyran, dihydropyran, or tetrahydropyridine. In still other embodiments, the present invention is a compound of formula I, wherein $Q^1$ is a 5-6 membered heteroaryl. In other embodiments, the present invention is a compound of formula I, wherein $Q^1$ is independently selected from pyrazolyl, pyridinyl, or pyrimidinyl.

In some embodiments, the present invention is a compound of formula I, wherein $J^Q$ is independently selected from a $C_{1-6}$aliphatic chain wherein up to three methylene units of the aliphatic chain are optionally replaced with —O—, —NR—, or —C(O)—. In another embodiment, the present invention is a compound of formula I, wherein $J^Q$ is independently selected from —C(O)—, —C(O)$C_{1-4}$alkyl or $C_{1-4}$alkyl. In other embodiments, the present invention is a compound of formula I, wherein $J^Q$ is methyl.

In another example, the present invention is a compound of formula I, wherein $J^R$ is independently selected from piperidinyl or piperazinyl.

In yet another example, the present invention is a compound of formula I, wherein $J^P$ is independently selected from oxetanyl or azetidinyl. In some embodiments, the present invention is a compound of formula I, wherein $R^3$ is T. In still other embodiments, the present invention is a compound of formula I, wherein T is a $C_{1-6}$aliphatic chain wherein up to three methylene units of the aliphatic chain are optionally replaced with —O—, —NR—, or —C(O)—. In yet another embodiment, the present invention is a compound of formula I, wherein T is —($C_{1-3}$alkyl)O($C_{1-3}$alkyl).

In other embodiments, the compounds of the present invention are represented by formula I-A:

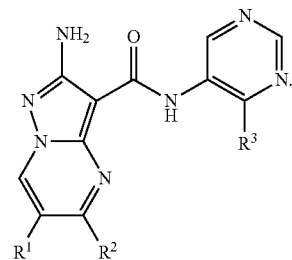

I-A

In some embodiments, the compounds of this invention are as represented in Table 1:

TABLE 1

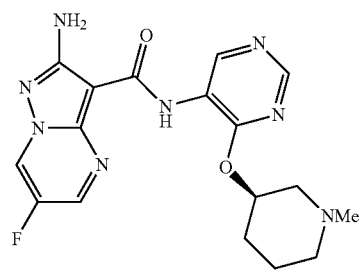 [SMILES: CN1CCC[C@@H](Oc2ncncc2NC(=O)c2c(N)nn3cc(F)cnc23)C1]

I-A-1

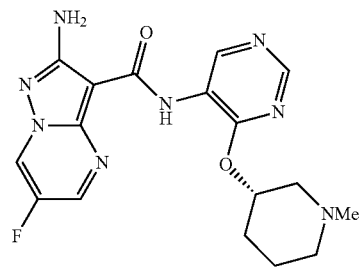 [SMILES: CN1CCC[C@H](Oc2ncncc2NC(=O)c2c(N)nn3cc(F)cnc23)C1]

I-A-2

TABLE 1-continued
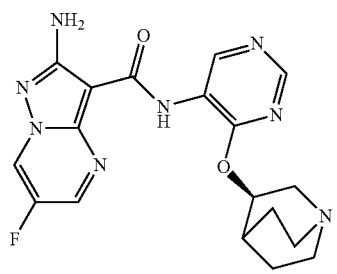 [SMILES: Nc1nn2cc(F)cnc2c1C(=O)Nc1cncnc1O[C@H]1CN2CCC1CC2]
I-A-3
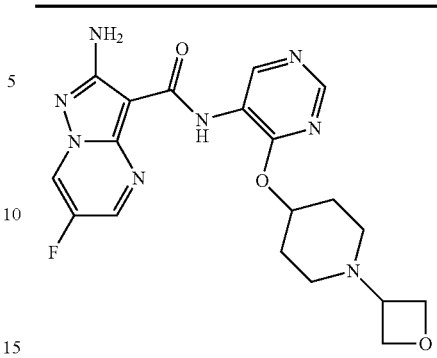
I-A-8, I-A-9
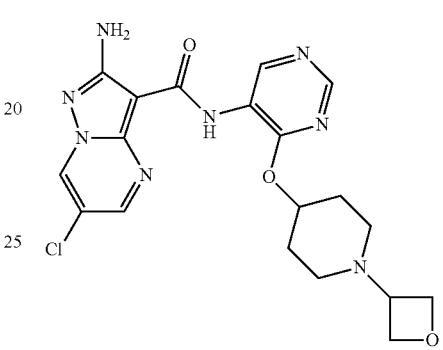
I-A-4, I-A-5
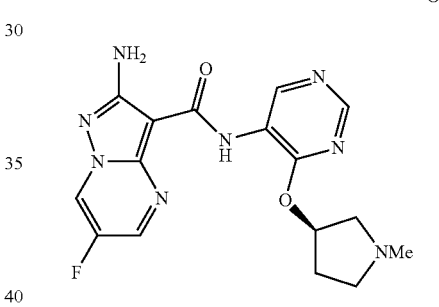
I-A-10
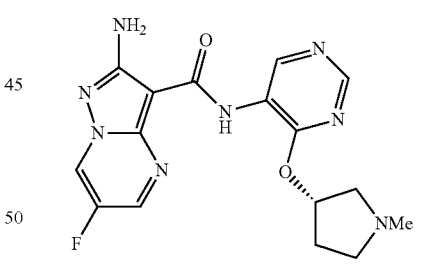
I-A-6, I-A-7
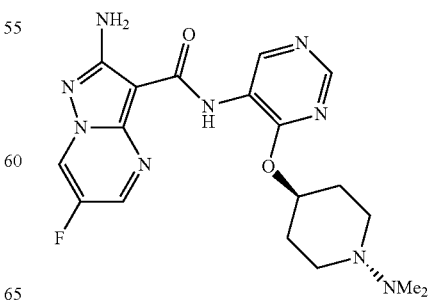
I-A-11, I-A-12

TABLE 1-continued
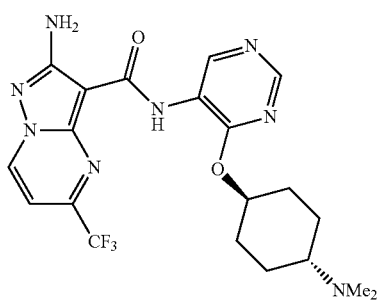 [SMILES: CN(C)[C@H]1CC[C@H](Oc2ncncc2NC(=O)c2c(N)nn3ccc(C(F)(F)F)nc23)CC1]
I-A-13
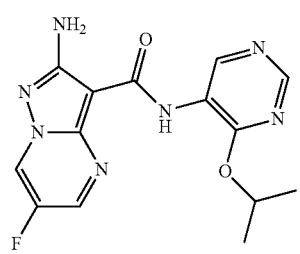 [SMILES: CC(C)Oc1ncncc1NC(=O)c1c(N)nn2cc(F)cnc12]
I-A-14
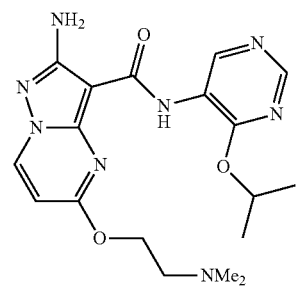 [SMILES: CC(C)Oc1ncncc1NC(=O)c1c(N)nn2ccc(OCCN(C)C)nc12]
I-A-15
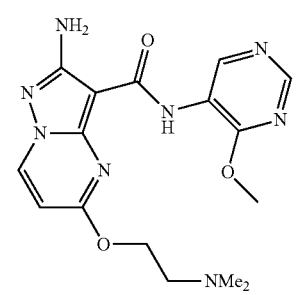 [SMILES: COc1ncncc1NC(=O)c1c(N)nn2ccc(OCCN(C)C)nc12]
I-A-16
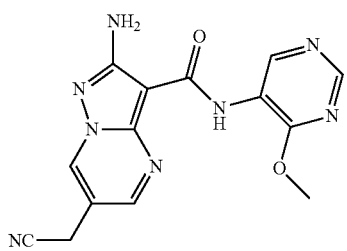 [SMILES: COc1ncncc1NC(=O)c1c(N)nn2cc(CC#N)cnc12]
I-A-17
TABLE 1-continued
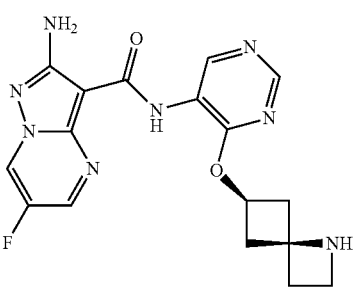 [SMILES: Nc1nn2cc(F)cnc2c1C(=O)Nc1cncnc1O[C@H]1C[C@]2(CCN2)C1]
I-A-18
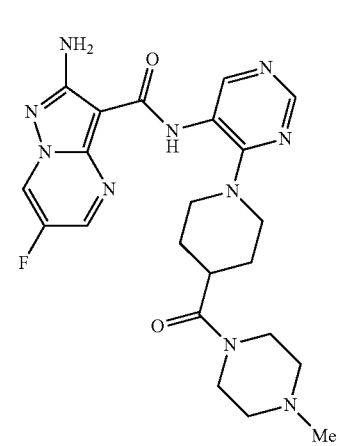 [SMILES: CN1CCN(C(=O)C2CCN(c3ncncc3NC(=O)c3c(N)nn4cc(F)cnc34)CC2)CC1]
I-A-19
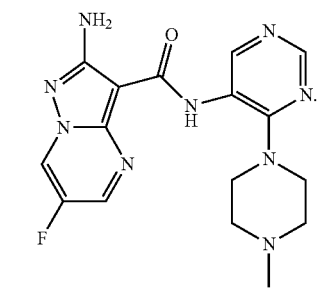 [SMILES: CN1CCN(c2ncncc2NC(=O)c2c(N)nn3cc(F)cnc23)CC1]
I-A-20
In one or more embodiments, the compounds of the present invention are represented by formula I-B:
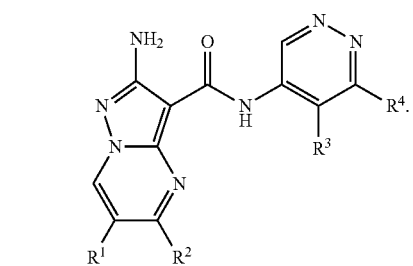
I-B
In yet another embodiment, the compounds of this invention are as represented in Table 2:

TABLE 2
I-B-1
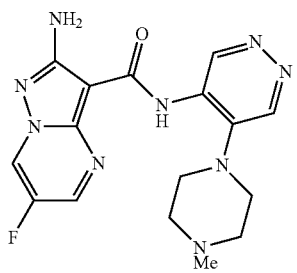
I-B-2
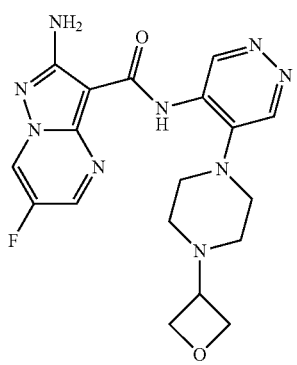 [SMILES: Nc1nn2cc(F)cnc2c1C(=O)Nc1cnncc1N1CCN(C2COC2)CC1]
I-B-3
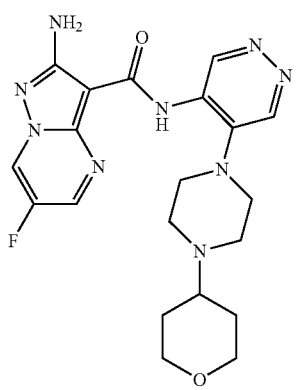 [SMILES: Nc1nn2cc(F)cnc2c1C(=O)Nc1cnncc1N1CCN(C2CCOCC2)CC1]
I-B-4
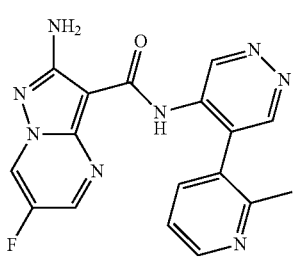 [SMILES: Cc1ncccc1-c1cnncc1NC(=O)c1c(N)nn2cc(F)cnc12]
TABLE 2-continued
I-B-5
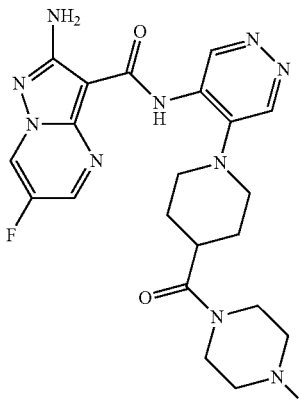
I-B-6
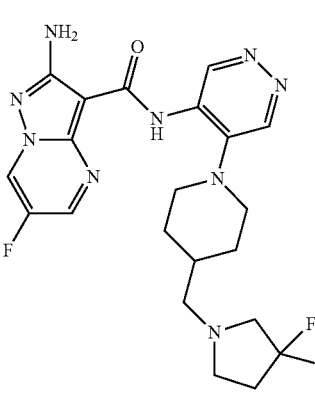
I-B-7
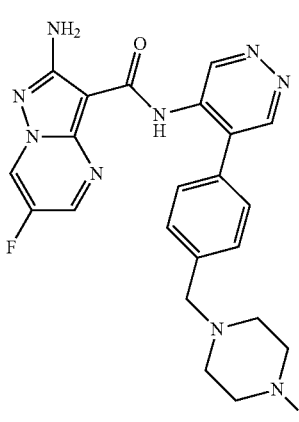
I-B-8
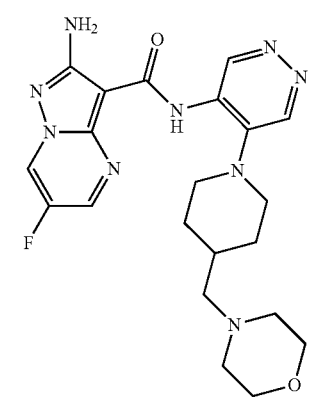 [SMILES: Nc1nn2cc(F)cnc2c1C(=O)Nc1cnncc1N1CCC(CN2CCOCC2)CC1]

TABLE 2-continued
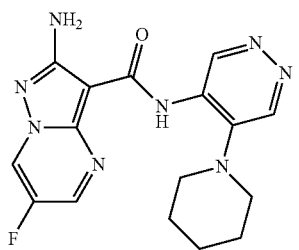 [SMILES: Nc1nn2cc(F)cnc2c1C(=O)Nc1cnncc1N1CCCCC1]
I-B-9
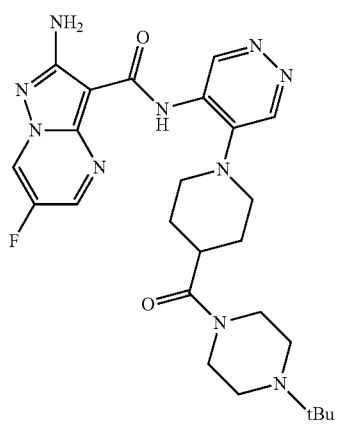
I-B-10
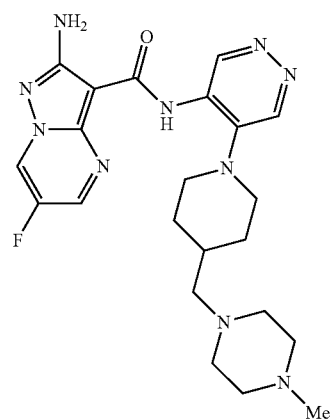 [SMILES: CN1CCN(CC2CCN(c3cnncc3NC(=O)c3c(N)nn4cc(F)cnc34)CC2)CC1]
I-B-11
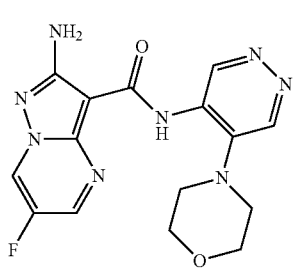
I-B-12
TABLE 2-continued
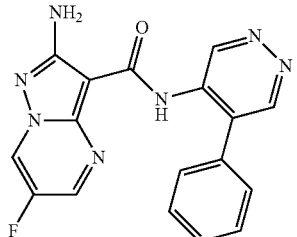
I-B-13
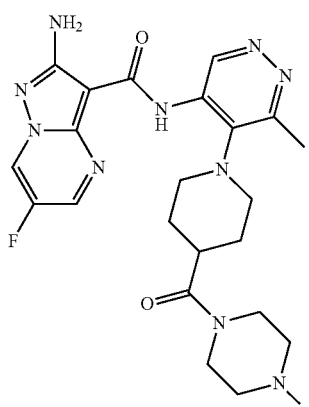
I-B-14
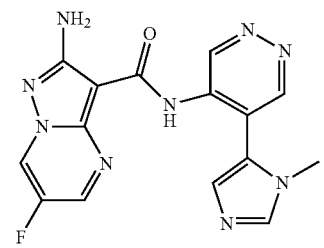
I-B-15
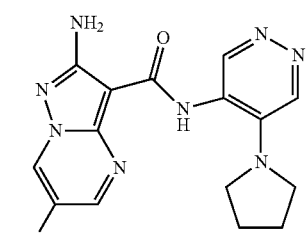
I-B-16
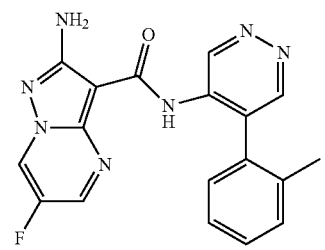
I-B-17

TABLE 2-continued
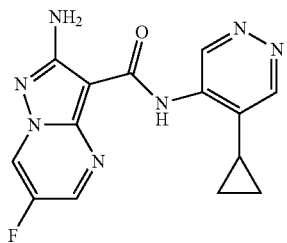 [SMILES: Nc1nn2cc(F)cnc2c1C(=O)Nc1cnncc1C1CC1]
I-B-18
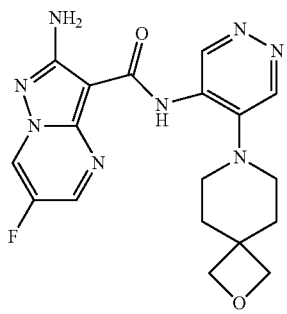 [SMILES: Nc1nn2cc(F)cnc2c1C(=O)Nc1cnncc1N1CCC2(CC1)COC2]
I-B-19
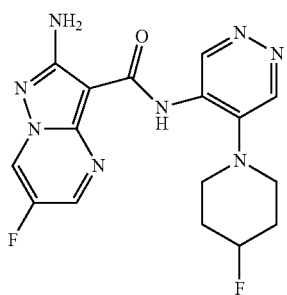 [SMILES: Nc1nn2cc(F)cnc2c1C(=O)Nc1cnncc1N1CCC(F)CC1]
I-B-20
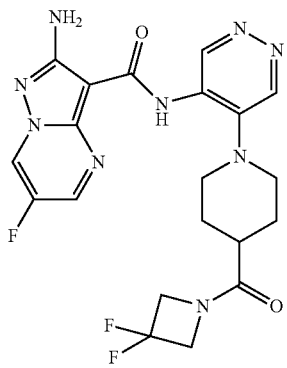 [SMILES: Nc1nn2cc(F)cnc2c1C(=O)Nc1cnncc1N1CCC(C(=O)N2CC(F)(F)C2)CC1]
I-B-21
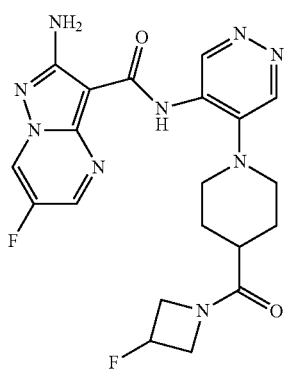 [SMILES: Nc1nn2cc(F)cnc2c1C(=O)Nc1cnncc1N1CCC(C(=O)N2CC(F)C2)CC1]
I-B-22
TABLE 2-continued
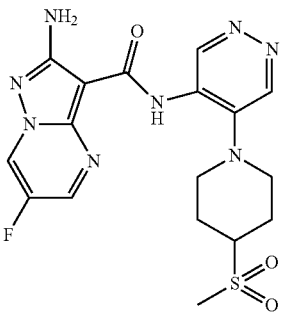
I-B-23
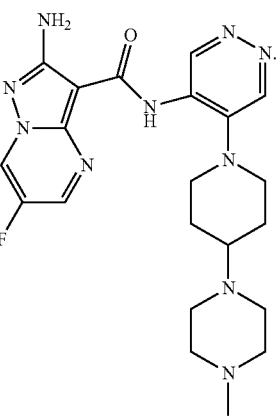
I-B-24
In another embodiment, the compounds of the present invention are represented by formula I-C:
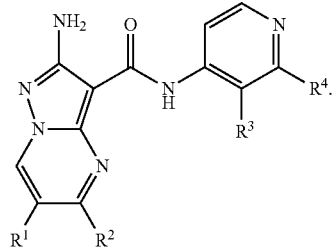
I-C
In other embodiments, the compounds of this invention are as represented in Table 3:
TABLE 3
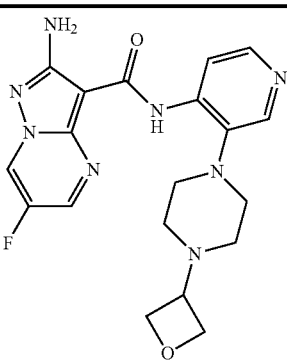
I-C-1

TABLE 3-continued
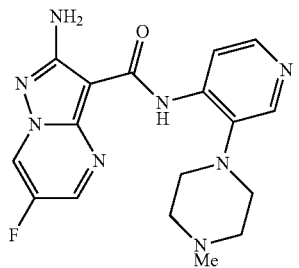 [SMILES: CN1CCN(c2cnccc2NC(=O)c2c(N)nn3cc(F)cnc23)CC1] I-C-2
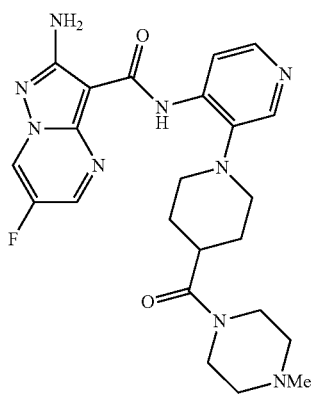 [SMILES: CN1CCN(C(=O)C2CCN(c3cnccc3NC(=O)c3c(N)nn4cc(F)cnc34)CC2)CC1] I-C-3
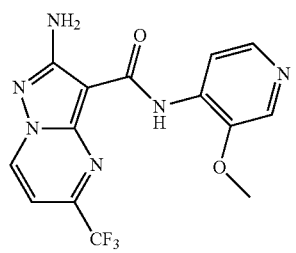 [SMILES: COc1cnccc1NC(=O)c1c(N)nn2ccc(C(F)(F)F)nc12] I-C-4
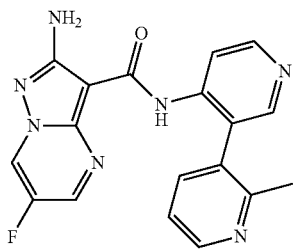 [SMILES: Cc1ncccc1-c1cnccc1NC(=O)c1c(N)nn2cc(F)cnc12] I-C-5
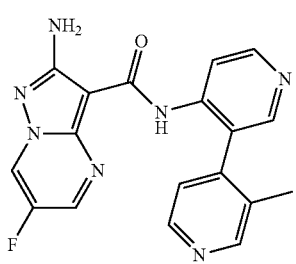 [SMILES: Cc1cnccc1-c1cnccc1NC(=O)c1c(N)nn2cc(F)cnc12] I-C-6
TABLE 3-continued
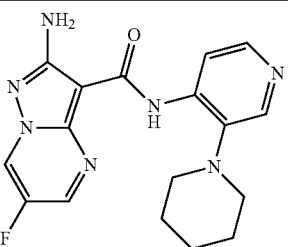 I-C-7
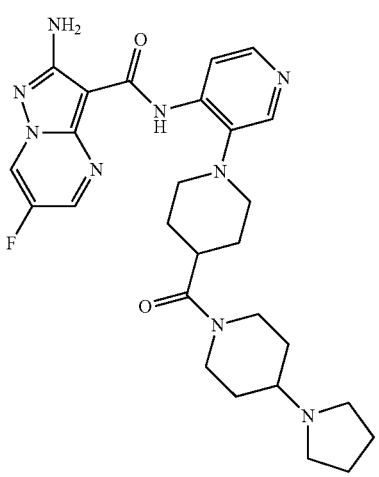 [SMILES: Nc1nn2cc(F)cnc2c1C(=O)Nc1ccncc1N1CCC(C(=O)N2CCC(N3CCCC3)CC2)CC1] I-C-8
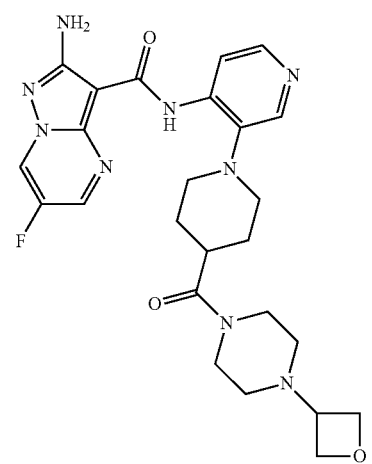 [SMILES: Nc1nn2cc(F)cnc2c1C(=O)Nc1ccncc1N1CCC(C(=O)N2CCN(C3COC3)CC2)CC1] I-C-9
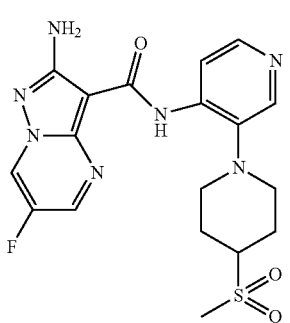 [SMILES: CS(=O)(=O)C1CCN(c2cnccc2NC(=O)c2c(N)nn3cc(F)cnc23)CC1] I-C-10

TABLE 3-continued

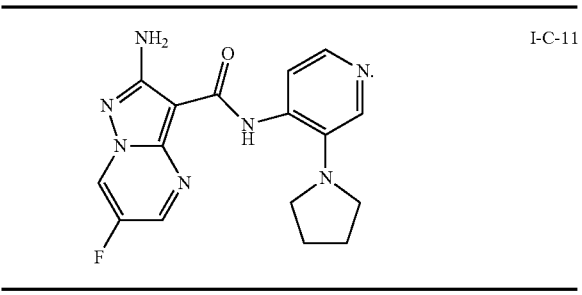

I-C-11

In another embodiment, the compounds of the present invention are represented by formula I-D:

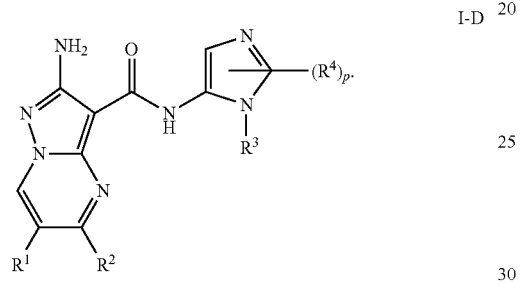

I-D

In other embodiments, the compounds of this invention are as represented in Table 4:

TABLE 4

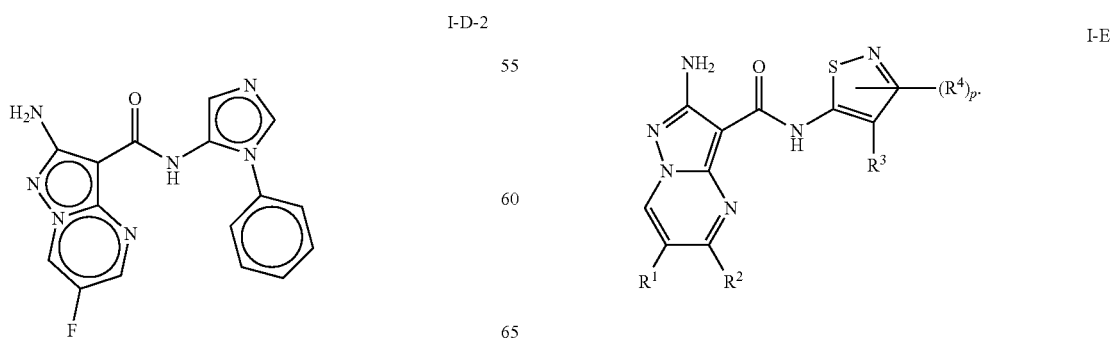

I-D-1

I-D-2

TABLE 4-continued

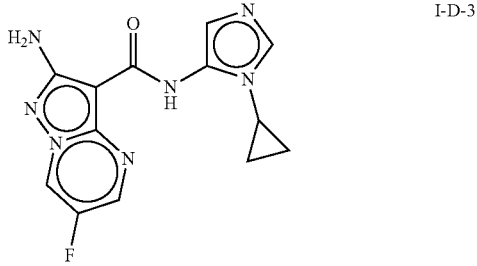

I-D-3

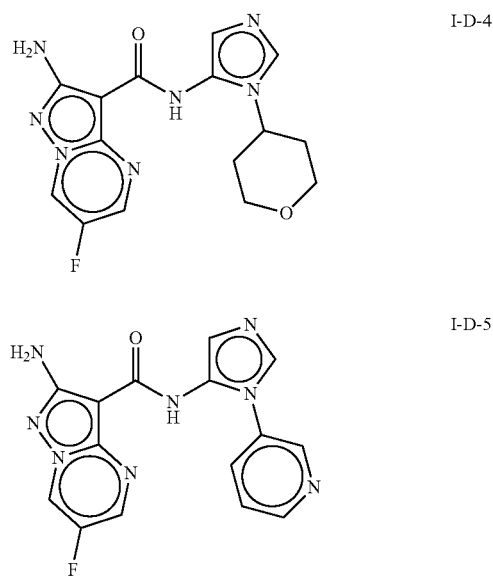

I-D-4

I-D-5

I-D-6

In another embodiment, the compounds of the present invention are represented by formula I-E:

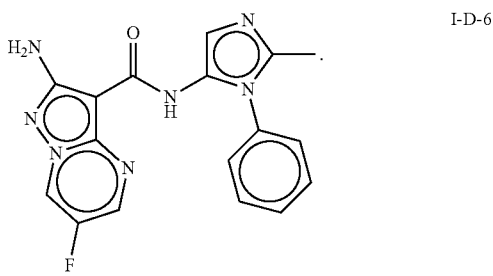

I-E

In other embodiments, the compounds of this invention are as represented in Table 5:

TABLE 5
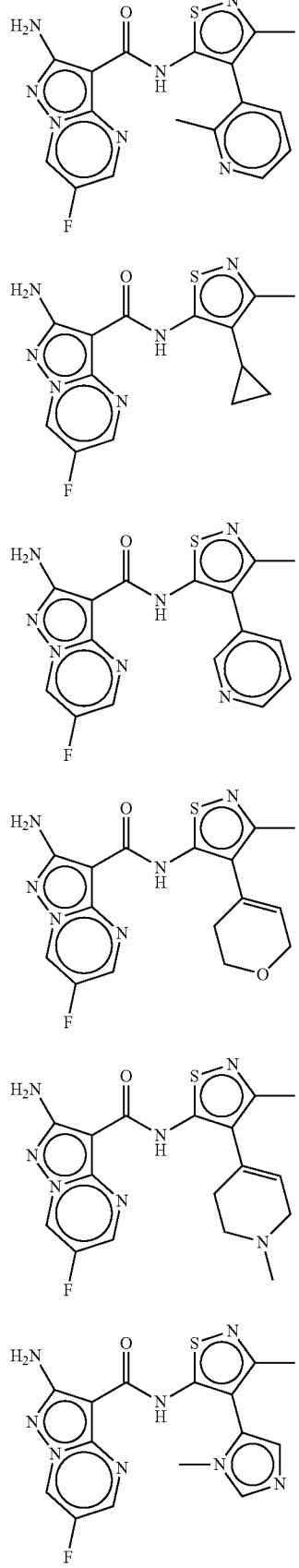
I-E-1
I-E-2
I-E-3
I-E-4
I-E-5
I-E-6
TABLE 5-continued
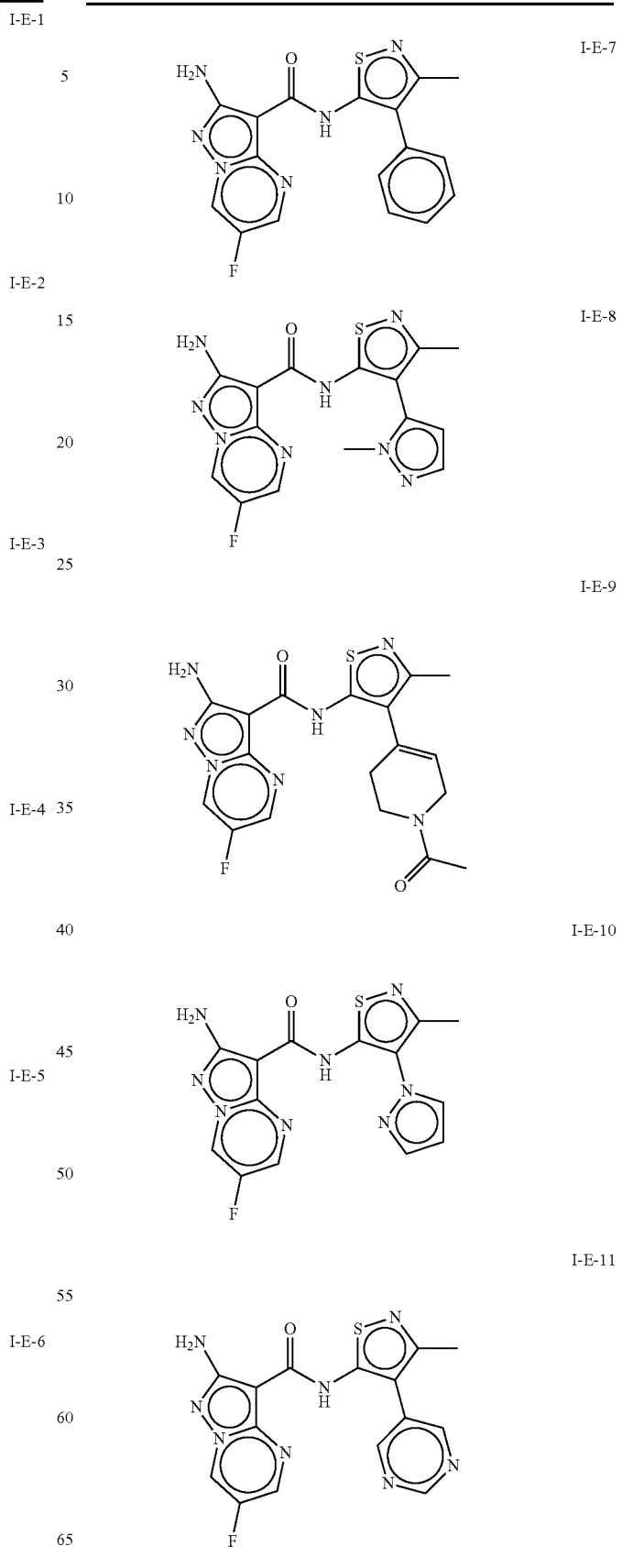
I-E-7
I-E-8
I-E-9
I-E-10
I-E-11

TABLE 5-continued
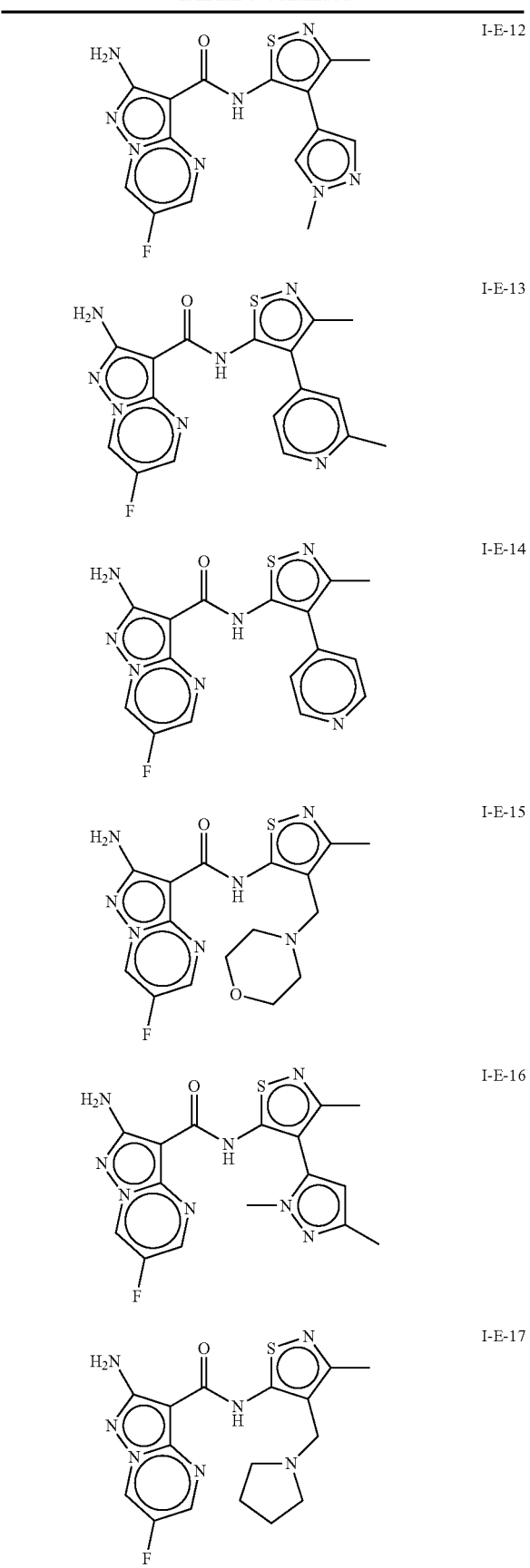
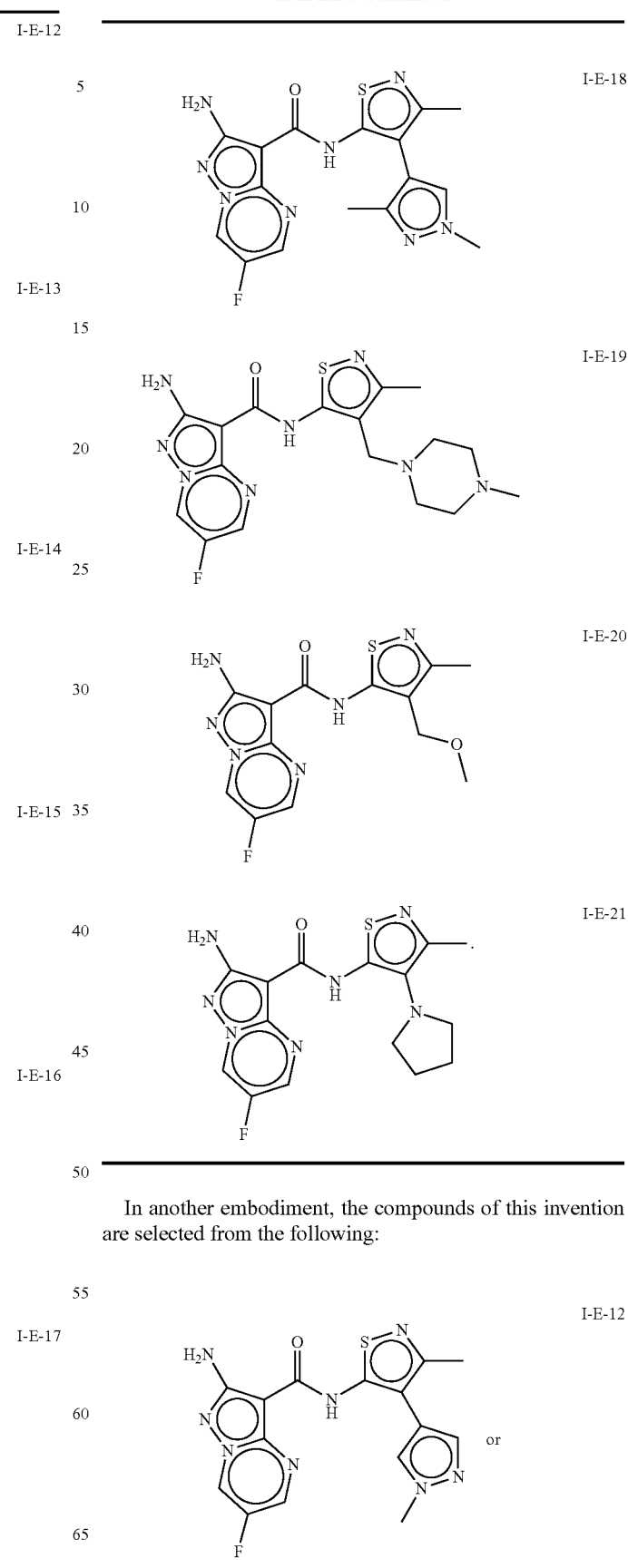
In another embodiment, the compounds of this invention are selected from the following:

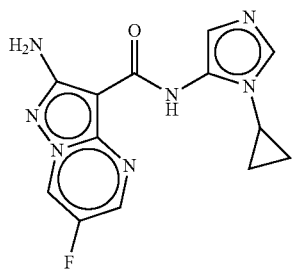

I-D-3

Another aspect of the present invention comprises a process for preparing a compound of formula I:

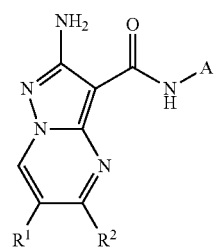

I comprising reacting a compound of formula 6:

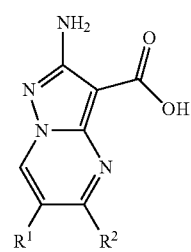

6 under suitable conditions to form an amide bond, wherein J, $R^1$, $R^2$, and A are as defined herein.

In some examples, the suitable conditions for forming the amide bond comprises reacting the compound of formula 6 with a substituted heteroaromatic amine in an aprotic solvent under heat. In other examples, the aprotic solvent is selected from NMP, optionally substituted pyridine, or DMF. In another embodiment, the aprotic solvent is optionally substituted pyridine. In still other embodiments, the reaction temperature is at least 80° C. In another embodiment, the reaction temperature is at least 100° C.

In another embodiment, the process, described above, further comprises preparing a compound of formula 6:

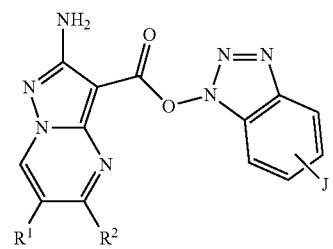

6 by reacting a compound of formula 5:

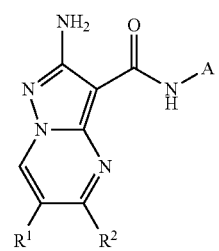

5 under suitable conditions to form an activated ester, wherein J, $R^1$, and $R^2$ are as defined herein.

In some embodiments, suitable conditions for forming the activated ester comprises reacting the compound of formula 5 with an amide coupling agent in the presence of an organic base. In another embodiment, the organic basis is an aliphatic amine. In still other embodiments, the organic base is independently selected from triethylamine or DIPEA. In one or more embodiments, the amide coupling agent is independently selected from EDCI, TBTU, TCTU, HATU, T3P, or COMU. In yet another embodiment, the amide coupling agent is independently selected from TBTU or TCTU. In still other embodiments, the amide coupling agent is TCTU Another aspect of the invention comprises a process for preparing a compound of formula I:

I comprising reacting a compound of formula 5:

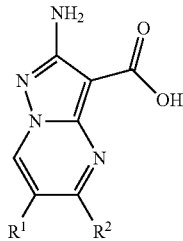

5 under suitable conditions to form an amide bond, wherein $R^1$, $R^2$, and A are as defined herein.

Yet another aspect of the present invention comprises a process for preparing a compound of formula 5:

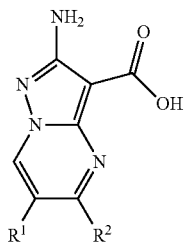

5 by reacting a compound of formula 4:

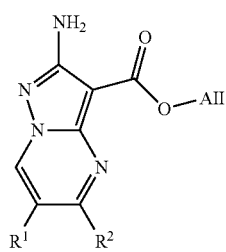

4 under suitable hydrolysis conditions, wherein $R^1$ and $R^2$ are as defined herein.

In some embodiments, suitable hydrolysis conditions comprise reacting the compound of formula 4 with a silane in the presence of a metal catalyst. In other embodiments, the silane is a phenylsilane. In another embodiment, the metal catalyst is a palladium catalyst. In yet another embodiment, the palladium catalyst is Pd(PPh$_3$)$_4$. In another embodiment, suitable hydrolytic conditions comprise reacting the compound of formula 4 with 4-methylbenzenesulfinate in the presence of a metal catalyst.

In still other embodiments, suitable hydrolytic conditions comprise reacting the compound of formula 4 with an aqueous alkali. In some embodiments, the aqueous alkali is selected from LiOH, NaOH or KOH.

Another aspect of the present invention comprises a process for preparing a compound of formula 4:

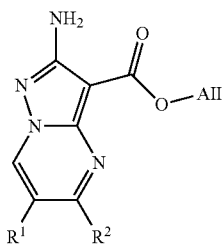

4 by reacting a compound of formula 3:

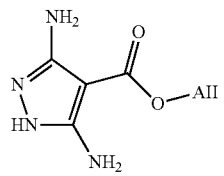

3 under suitable condensation conditions to form a pyrimidine ring.

In some embodiments, suitable condensation conditions to form a pyrimidine ring comprise reacting the compound of formula 3 with a 1,3-dielectrophilic species in the presence of a solvent. In some instances, the condensation reaction is carried out in the presence of a strong base. In some embodiments, the strong base is KOH. In another embodiment, the condensation reaction is carried out in the presence of a weak base. In yet another embodiment, the weak base is triethylamine. In another embodiment, the 1,3-dielectrophilic species is selected from 1,3-dialdehyde or a 3-(dialkylamino)-prop-2-enal. In still other embodiments, the solvent is selected from dioxane, DMF, or DMSO in water. In other embodiments, the 1,3-dielectrophilic species is generated in situ from a protected 1,3-dielectrophilic species. In other embodiments, the 1,3-dielectrophilic species is generated in situ from a protected 1,3-dielectrophilic species. In another embodiment the 1,3-dielectrophilic species is generated from a ketal in the presence of a sulfonic acid. In some embodiments, the sulfonic acid is PTSA.

Another aspect of the present invention comprises a process for preparing the compound of formula 3:

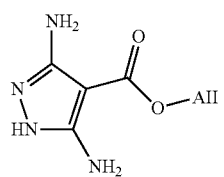

3 by reacting a compound of formula 2:

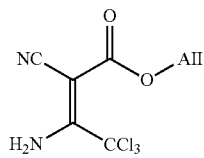

2 under suitable condensation conditions to form a pyrazole ring.

In some embodiments, suitable condensation conditions to form a pyrazole ring comprise reacting the compound of formula 2 with a hydrazine or hydrazine hydrate in the presence of an aprotic solvent under basic conditions. In another embodiment, the aprotic solvent is DMF. In yet another embodiment, the basic conditions comprise reacting the compound of formula 2 in the presence of potassium acetate or sodium acetate.

Yet another aspect of the present invention comprises a process for preparing a compound of formula 2:

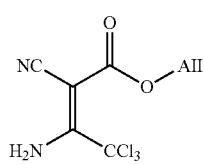

2 by reacting a compound of formula 1:

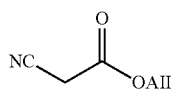

1 under suitable anion condensation conditions.

In some embodiments, suitable anion condensation conditions comprise 1) reacting the compound of formula 1 with a base, in the presence of a solvent, to generate the anion of the compound of formula 1; and 2) reacting the anion of the compound of formula 1 with trichloroacetonitrile. In still other embodiments, the base is potassium acetate. In yet another embodiment, the solvent is an alcohol. In other embodiments, the solvent is isopropylalcohol.

Another aspect of the invention, comprises a process for preparing a compound of formula I:

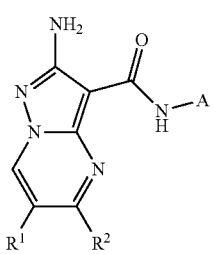

I comprising reacting a compound of formula 9:

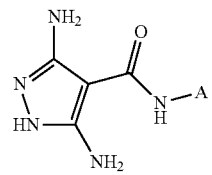

9 under suitable condensation conditions to form a pyrimidine ring, wherein $R^1$, $R^2$, and A are as defined herein.

In some embodiments, suitable condensation conditions to form a pyrimidine ring comprise reacting the compound of formula 9 with a 1,3-dielectrophilic species in the presence of a solvent. In another embodiment, the 1,3-dielectrophilic species is selected from 1,3-dialdehyde or a 3-(dialkylamino)-prop-2-enal. In still other embodiments, the solvent is selected from dioxane, iPrOH in water, DMF, or DMSO in water. In other embodiments, the 1,3-dielectrophilic species is generated in situ from a protected 1,3-dielectrophilic species. In another embodiment the 1,3-dielectrophilic species is generated from a ketal in the presence of a sulfonic acid. In yet another embodiment, the sulfonic acid is PTSA.

Yet another aspect of the present invention comprises a process for preparing a compound of formula 9:

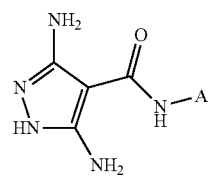

9 by reacting a compound of formula 8:

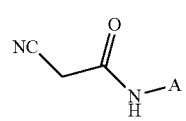

8 under suitable condensation conditions to form a pyrazole ring.

In some embodiments, suitable condensation conditions to form a pyrazole ring comprise 1) reacting the compound of formula 8 with a base, in the presence of a solvent, to generate the anion of the compound of formula 8; 2) reacting the anion with trichloroacetonitrile; and 3) reacting the product from 2) with a hydrazine or hydrazine hydrate in the presence of an aprotic solvent. In another embodiment, the aprotic solvent is NMP or DMF. In some embodiments, the base is selected from sodium acetate or potassium acetate.

Another embodiment comprises a process for preparing a compound of formula 8:

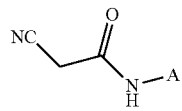

8 by reacting a compound of formula 7

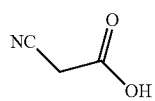

7 under suitable conditions to form an amide bond.

In some examples, the suitable conditions for forming the amide bond comprises reacting the compound of formula 7 with a substituted heteroaromatic amine with an amide coupling agent in the presence of an aprotic solvent and an organic base. In other examples, the aprotic solvent is selected from NMP, DCM, or DMF. In another embodiment, the organic base is an aliphatic amine. In still other embodiments, the organic base is independently selected from triethylamine or DIPEA. In yet another embodiment, the amide coupling agent is independently selected from TBTU or TCTU. In still other embodiments, the reaction temperature is at least 80° C. In another embodiment, the reaction temperature is at least 100° C.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^W$ can be bonded to any position on the pyridyl ring. For bicyclic rings, a bond drawn through both rings indicates that the substituent can be bonded from any position of the bicyclic ring. In example ii below, for instance, $J^W$ can be bonded to the 5-membered ring (on the nitrogen atom, for instance), and to the 6-membered ring.

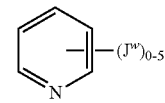

i

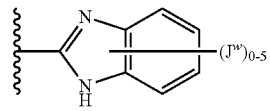

ii

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH₂-cyclopropyl, CH₂CH₂CH(CH₃)-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

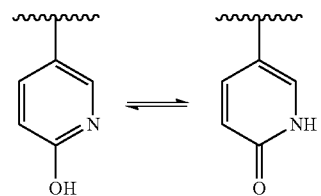

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$=CN. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. In another example, if a methylene unit of —CH$_2$CH$_2$CH$_3$ was optionally replaced with —NH—, the resulting compound could be —NHCH$_2$CH$_3$, —CH$_2$NHCH$_3$, or —CH$_2$CH$_2$NH$_2$. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

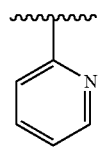

also represents

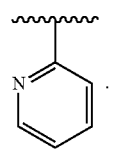

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

ABBREVIATIONS

The following abbreviations are used:
DMSO dimethyl sulfoxide
DCM dichloromethane
ATP adenosine triphosphate
$^1$HNMR proton nuclear magnetic resonance
HPLC high performance liquid chromatography
LCMS liquid chromatography-mass spectrometry
Rt retention time RT room temperature
TEA triethylamine
NMP N-methyl-2-pyrrolidone
TFA trifluoroacetic acid
DMF dimethylformamide
DIPEA N,N-diisopropylethylamine
mCPBA meta-chloroperoxybenzoic acid
Bp Boiling point
THF tetrahydrofuran
HOBT hydroxybenzotriazole
HATU 1-[Bis(dimethylamino)methylene]-1H-1,2,3-triazolo[4,5-b]pyridinium 3-oxid hexafluorophosphate
T3P Propylphosphonic anhydride
COMU 1-[(1-(Cyano-2-ethoxy-2-oxoethylideneaminooxy)-dimethylamino-morpholino)]uroniumhexafluorophosphate
TBTU 2-(1H-benzotriazole-1-yl)-1,1,3,3-tetramethyluronium tetrafluoroborate
TCTU 0-(6-Chloro-1-hydrocibenzotriazol-1-yl)-1,1,3,3-tetramethyluronium tetrafluoroborate
EDCI 1-Ethyl-3-(3-dimethylaminopropyl)carbodiimide Compound Uses One aspect of this invention provides compounds that are inhibitors of ATR kinase, and thus are useful for treating or lessening the severity of a disease, condition, or disorder in a subject or patient where ATR is implicated in the disease, condition, or disorder.

As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

Another aspect of this invention provides compounds that are useful for the treatment of diseases, disorders, and conditions characterized by excessive or abnormal cell proliferation. Such diseases include a proliferative or hyperproliferative disease. Examples of proliferative and hyperproliferative diseases include, without limitation, cancer and myeloproliferative disorders.

In some embodiments, said compounds are selected from the group consisting of a compound of formula I. In another aspect, said compounds are selected from the group consisting of formula I-A. In yet another aspect of the present invention, said compounds are selected from the group consisting of formula I-B. In still other embodiments, said compounds are selected from the group consisting of formula I-C. In another embodiment, said compounds are selected from the group consisting of formula I-D. In some embodiments, said compounds are selected from the group consisting of formula I-E. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological/Female: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from a cancer of the lung or the pancreas. In other embodiments, the cancer is selected from lung cancer, head and neck cancer, pancreatic cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the cancer is lung cancer. In other embodiments, the lung cancer is non-small cell lung cancer or small cell lung cancer. In another embodiment, the cancer is non-small cell lung cancer. In yet another embodiment, the non-small cell lung cancer is squamous non-small cell lung cancer.

Thus, the term "cancerous cell" as provided herein, includes a cell afflicted by any one of the above-identified conditions. In some embodiments, the cancer is selected from colorectal, thyroid, or breast cancer. In other embodiments, the cancer is triple negative breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the dosing schedule of the compounds of the present invention may vary.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions. Alternatively, a dosage of between 0.01-50 mg/kg body weight/dose of the inhibitor can be administered to a patient receiving these compounds.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, actinomycin) and Ultraviolet light.

Another embodiment provides administering a compound of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); Po1B, Po1G (polymerases); FEN1 (endonuclease) or Aprataxin. In other embodiments, the base excision repair protein is selected from PARP1, PARP2, or Po1B. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I, formula I-A, formula I-B, formula I-C, formula I-D, and formula I-E.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas.

In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the lung cancer is small cell lung cancer and the additional therapeutic agents are cisplatin and etoposide. In other examples, the lung cancer is non-small cell lung cancer and the additional therapeutic agents are gemcitabine and cisplatin. In yet other embodiments, the non-small cell lung cancer is squamous non-small cell lung cancer. In another embodiment, the cancer is breast cancer and the additional therapeutic agent is cisplatin. In other embodiments, the cancer is triple negative breast cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family include Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

In some embodiments, the additional therapeutic agent is ionizing radiation. In other embodiments, the additional therapeutic agent is Cisplatin or Carboplatin. In yet other embodiments, the additional therapeutic agent is Etoposide. In yet other embodiments, the additional therapeutic agent is Temozolomide.

In certain embodiments, the additional therapeutic agent is selected from one or more of the following: Cisplatin, Carboplatin, gemcitabine, Etoposide, Temozolomide, or ionizing radiation.

Another embodiment provides methods for treating pancreatic cancer by administering a compound described herein in combination with another known pancreatic cancer treatment. One aspect of the invention includes administering a compound described herein in combination with gemcitabine. In some embodiments, the pancreatic cancer comprises one of the following cell lines: PSN-1, MiaPaCa-2 or Panc-1. According to another aspect, the cancer comprises one of the following primary tumor lines: Panc-M or MRC5.

Another aspect of the invention includes administering a compound described herein in combination with radiation therapy. Yet another aspect provides a method of abolishing radiation-induced G2/M checkpoint by administering a compound described herein in combination with radiation treatment.

Another aspect provides a method of treating pancreatic cancer by administering to pancreatic cancer cells a compound described herein in combination with one or more cancer therapies. In some embodiments, the compound is combined with chemoradiation, chemotherapy, and/or radiation therapy. As would be understood by one of skill in the art, chemoradiation refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering a compound described herein in combination with the cancer therapy. In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering a compound described herein after treatment with gemcitabine (100 nM) and/or radiation (6 Gy) to a pancreatic cancer cell.

Another aspect provides method of radiosensitizing hypoxic PSN-1, MiaPaCa-2 or PancM tumor cells by administering a compound described herein to the tumor cell in combination with radiation therapy.

Yet another aspect provides a method of sensitizing hypoxic PSN-1, MiaPaCa-2 or PancM tumor cells by administering a compound described herein to the tumor cell in combination with gemcitabine.

Another aspect provides a method of sensitizing PSN-1 and MiaPaCa-2 tumor cells to chemoradiation by administering a compound described herein to the tumor cells in combination with chemoradiation.

Another aspect provides a method of disrupting damage-induced cell cycle checkpoints by administering a compound described herein in combination with radiation therapy to a pancreatic cancer cell.

Another aspect provides a method of inhibiting repair of DNA damage by homologous recombination in a pancreatic cancer cell by administering a compound described herein in combination with one or more of the following treatments: chemoradiation, chemotherapy, and radiation therapy.

In some embodiments, the chemotherapy is gemcitabine.

Another aspect provides a method of inhibiting repair of DNA damage by homologous recombination in a pancreatic cancer cell by administering a compound described herein in combination with gemcitabine and radiation therapy.

In some embodiments, the pancreatic cancer cells are derived from a pancreatic cell line selected from PSN-1, MiaPaCa-2 or Panc-1.

In other embodiments, the pancreatic cancer cells are in a cancer patient.

Another aspect of the invention provides a method of treating non-small cell lung cancer comprising administering to a patient a compound described herein in combination with one or more of the following additional therapeutic agents: Cisplatin or Carboplatin, Etoposide, and ionizing radiation. Some embodiments comprise administering to a patient a compound described herein in combination with Cisplatin or Carboplatin, Etoposide, and ionizing radiation. In some embodiments the combination is Cisplatin, Etoposide, and ionizing radiation. In other embodiments the combination is Carboplatin, Etoposide, and ionizing radiation.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. According to another embodiment, the method is used on a cancer, cancer cell, or cell expressing DNA damaging oncogenes.

In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (http://www.sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunhohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); Po1B, Po1G (polymerases); FEN1 (endonuclease) or Aprataxin.

In some embodiments, the base excision repair protein is PARP1, PARP2, or Po1B. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Compounds and Compositions for Use

One embodiment provides a compound or composition as described herein for use as a radio-sensitizer or a chemo-sensitizer. Another embodiment provides a compound or composition as described herein for use as a single agent (monotherapy) for treating cancer.

Another embodiment provides a compound or composition as described herein for treating patients having cancer with a DNA-damage response (DDR) defect. In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides compounds or compositions described herein for treating cancer. In some embodiments, the compound or composition is further combined with an additional therapeutic agent described herein. In some embodiments, the compound or composition is further combined with a DNA damaging agent described herein.

In some embodiments, the cancer has a defect in a pathway described herein.

Manufacture of Medicaments

One embodiment provides the use of a compound or composition described herein for the manufacture of a medicament for use as a radio-sensitizer or a chemo-sensitizer. Another embodiment provides the use of a compound or composition described herein for the manufacture of a medicament for the manufacture of a medicament for use as a single agent (monotherapy) for treating cancer.

Yet another embodiment provides the use of a compound or composition described herein for the manufacture of a medicament for the manufacture of a medicament for treating patients having cancer with a DNA-damage response (DDR) defect.

In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides the use of a compound or composition described herein for the manufacture of a medicament for treating cancer. In some embodiments, the compound or composition is combined with an additional therapeutic agent, such as a DNA damaging agent, described herein. In another embodiment, the cancer has a defect in a pathway described herein.

EXPERIMENTAL MATERIALS AND METHODS

All commercially available solvents and reagents were used as received. Microwave reactions were carried out using a CEM Discovery microwave. Flash chromatography was carried out on an ISCO© Combiflash® Companion™ system eluting with a 0 to 100% EtOAc/petroleum ether gradient. Samples were applied pre-absorbed on silica. Other methods known in the art were also utilized to perform Flash Chromotography. Where stated, supercritical fluid chromatography (SFC) was performed on a Berger Minigram SFC machine. All $^1$H NMR spectra were recorded using a Bruker Avance III 500 instrument at 500 MHz. MS samples were analyzed on a Waters SQD mass spectrometer with electrospray ionization operating in positive and negative ion mode. Samples were introduced into the mass spectrometer using chromatography. All final products had a purity ≥95%, unless specified otherwise in the experimental details. HPLC purity was measured on a Waters Acquity UPLC system with a Waters SQD MS instrument equipped with a Waters UPLC BEH C8 1.7 µm, 2.1×50 mm column and a Vanguard BEH C8 1.7 µm, 2.1×5 mm guard column.

As used herein, the term "Rt(min)" refers to the HPLC retention time, in minutes, associated with the compound.

magnetic resonance). The following generic schemes and examples illustrate how to prepare the compounds of the present disclosure. The examples are for the purpose of illustration only and are not to be construed as limiting the scope of the invention in any way.

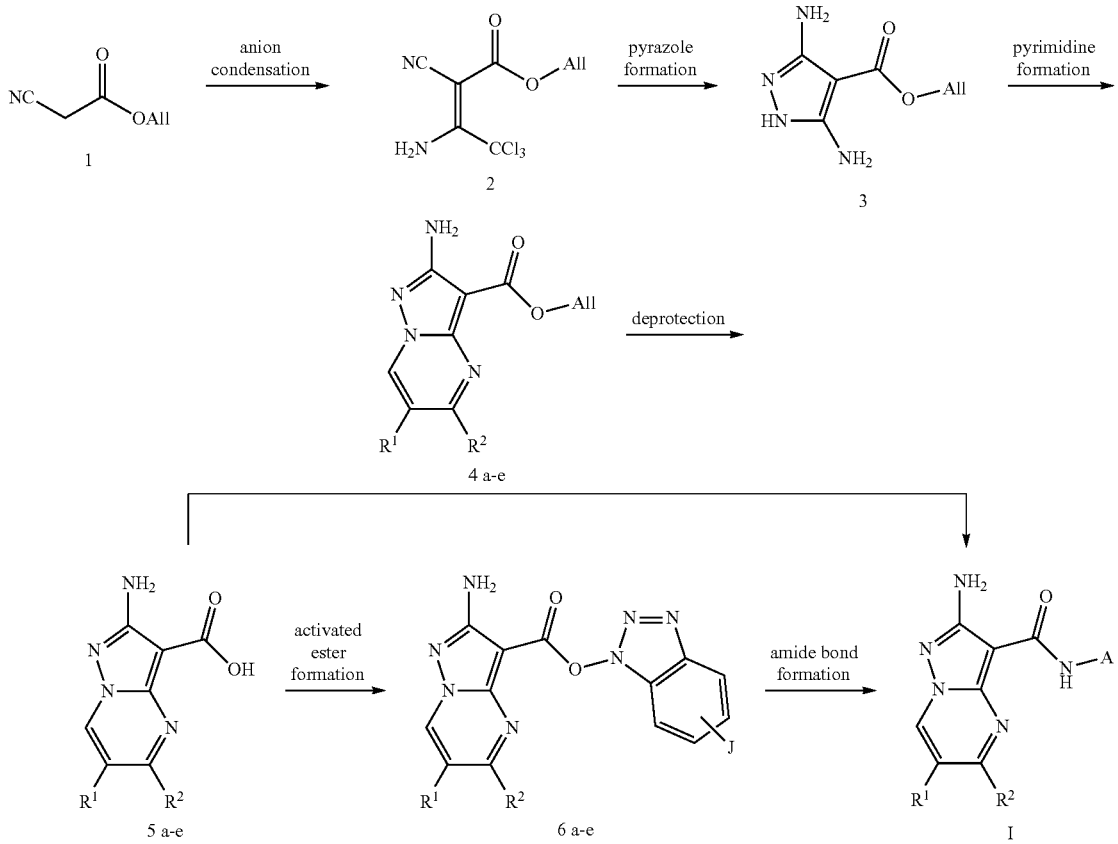

Scheme 1: General approach for the preparation of compounds of formula I

Unless otherwise indicated, the HPLC methods utilized to obtain the reported retention times are as described below:
HPLC Method
Instrument: Waters Acquity UPLC-MS;
Column: Waters UPLC BEH C8 1.7 µm, 2.1×50 mm with Vanguard BEH C8 1.7 µm, 2.1×5 mm guard column;
Column temperature: 45° C.;
Mobile Phase A: 10 mM ammonium formate in water:acetonitrile 95:5, pH 9;
Mobile Phase B: acetonitrile;
Detection: 210-400 nm;
Gradient: 0-0.40 min: 2% B, 0.40-4.85 min: 2% B to 98% B, 4.85-4.90 min: 98% B to 2% B, 4.90-5.00 min: hold at 2% B;
Flow rate: 0.6 mL/minute.

EXAMPLES AND SCHEMES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear Compounds of this invention can be synthesised according to methods similar to the one depicted in Scheme 1.

The anion of commercially available allyl cyanoacetate 1 can react with trichloroacetonitrile to provide intermediate 2. In the anion condensation step, the anion of commercially available allyl cyanoacetate 1 can be generated with a base such as potassium acetate in an appropriate solvent such as an alcohol (e.g., isopropylalcohol). The anion then reacts with trichloroacetonitrile at room temperature.

In the pyrazole formation step, intermediate 2 is reacted with hydrazine (or its hydrate) in an aprotic solvent, such as DMF, to provide the diaminopyrazole 3. The reaction occurs under basic conditions (eg in the presence of potassium acetate or AcONa) with heating (e.g., 110° C.) to ensure complete cyclisation. Intermediate 2 then reacts with hydrazine to form the diaminopyrazole 3, which can further be condensed with a dielectrophilic coupling partner to form the pyrimidine 4 a-e.

In the pyrimidine formation step, intermediate 3 is reacted with a 1,3-dielectrophilic species (e.g., a 1,3-dialdehyde or a 3-(dialkylamino)-prop-2-enal) in various types of solvents (e.g., DMF, or DMSO/water) to furnish the bicyclic cores 4a-e. In some instances, the reaction is carried out in the presence of a strong base, e.g., KOH. In other instances, the reaction is carried out in the presence of a weak base, e.g., triethylamine. When one or two of the electrophilic centers is protected/masked (eg aldehyde masked as a ketal), introduction of a sulfonic acid (eg PTSA) may be required to liberate the reactive functional group.

Deprotection, e.g., via hydrolysis, of the allyl ester leads to the carboxylic acids 5 a-e. In the deprotection step, compounds 4a-e are subjected to hydrolytic conditions that are known to those skilled in the art. For example, treatment of 4 with phenylsilane or 4-methylbenzenesulfinate in the presence of a catalytic amount of palladium (e.g., $Pd(PPh_3)_4$) leads to the formation of the corresponding carboxylic acid 5a-e. Alternatively, compounds 4a-e could be treated with aqueous alkali (e.g., NaOH or KOH) to produce acids 5a-e.

In the activated ester formation step, the carboxylic acids 5a-e are reacted with amide coupling agents known to those skilled in the art. When the coupling agent is chosen appropriately, the reactions can proceed rapidly (~1 h) at room temperature in the presence of an organic base (e.g., triethylamine, DIPEA) to provide the activated esters 6. For example, when the amide coupling agents TBTU [J=H] or TCTU [J=Cl] are used, compounds 6 are obtained readily by filtration of the reaction mixture.

Formation of the activated esters 6 a-e prior to the amide bond formation to prepare a compound of formula I is generally preferred, although a direct conversion of 5 a-e into the compounds of formula I of this invention is also possible. Alternative activated esters can also be utilised (isolated or formed in situ) and will be known to those skilled in the art (e.g, using TCTU, HATU, T3P, COMU coupling agents).

In the amide bond formation step, activated esters 6 can react with a substituted heteroaromatic amine to provide compounds I of this invention. The reaction conditions for the amide coupling are generally in a aprotic solvent (e.g., NMP, pyridine, DMF, etc) with heating (e.g., >90° C.). The heteroaromatic amine may be further functionalized following amide bond formation.

Alternatively, the two steps described above can be combined: carboxylic acids 5a-e can be used as starting points for the amide bond formation, the activated esters being generated in situ, using the same amide couplings agents as those described above. Compounds I of this invention are isolated in a similar manner to the one described above (specific details are given in Examples below).

Scheme 2: Alternative approach for the preparation of compounds of formula I

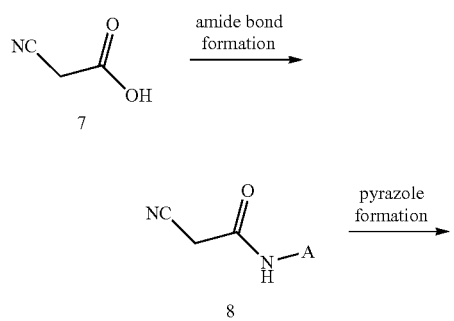

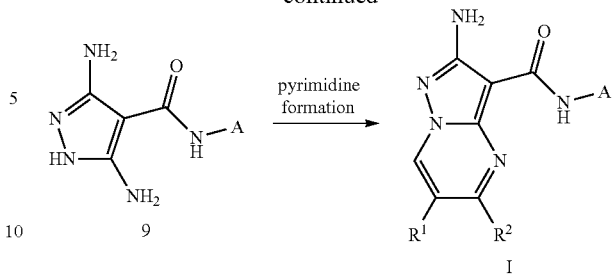

Alternatively, compounds of the present disclosure can be prepared according to methods similar to the one depicted in Scheme 2.

The amide 8 can readily be prepared from commercially available cyanoacetic acid 7. In the amide bond formation step, cyanoacetic acid 7 can react with a substituted heteroaromatic amine to provide compounds 8. The reaction conditions for the amide coupling are generally in a aprotic solvent (e.g., DCM, NMP, DMF, etc), in the presence of an organic base such as an aliphatic amine (e.g., triethylamine or DIPEA) and an amide coupling agent known to those skilled in the art: for example EDCI, TBTU, COMU, T3P, etc.

In the pyrazole formation step, the anion of cyanoamide 8 can be generated with a base (such as potassium or sodium acetate) in an appropriate solvent such as an alcohol (e.g., ethanol). The anion then reacts with trichloroacetonitrile at room temperature (specific details are given in Examples below). The resulting solid, which can be collected by filtration, is then reacted with hydrazine (or its hydrate) in an aprotic solvent, such as DMF or NMP, to provide the diaminopyrazole 9. Intermediate 9 is further condensed with a dielectrophilic coupling partner to form the pyrimidine portion of the compounds of formula I of this invention.

In the pyrimidine formation step, intermediate 9 is reacted with a 1,3-dielectrophilic species (e.g., a 1,3-dialdehyde or a 3-(dialkylamino)-prop-2-enal) in various types of solvents (e.g., iPrOH/water, DMF, or DMSO/water) to furnish the desired products of formula I. When one or two of the electrophilic centers is protected/masked (e.g., aldehyde masked as a ketal), introduction of a sulfonic acid (e.g., PTSA) is required to liberate the reactive functional group.

Preparation 1: Allyl 3,5-diamino-1H-pyrazole-4-carboxylate

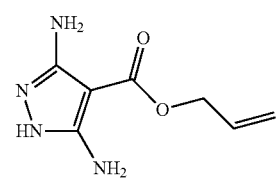

Step 1: allyl 3-amino-4,4,4-trichloro-2-cyanobut-2-enoate 2

To a solution of KOAc (589.4 g, 6.006 mol) in isopropanol (3 L) was added allyl cyanoacetate (429.4 g, 403.2 mL, 3.432 mol) and the reaction mixture was cooled to 5° C. Trichloroacetonitrile (495.5 g, 3.432 mol) was added in 50 mL portions, maintaining temperature below 15° C. The reaction mixture was then allowed to warm to 20° C. and stirred for 3 h. Water (~4 L) was added to dissolve the inorganic materials and precipitate out the desired product. The mixture was stirred for 20 minutes and the solid was isolated by filtration under vacuum. This solid was filtered, washed with water (2×0.5 L) and dried in a vacuum oven overnight at 40° C. to afford allyl 3-amino-4,4,4-trichloro-2-cyanobut-2-enoate 2 as an off-white powder (787 g, 85%)

Step 2: Allyl 3,5-diamino-1H-pyrazole-4-carboxylate 3

To a suspension of allyl 3-amino-4,4,4-trichloro-2-cyanobut-2-enoate 2 (619 g, 2.297 mol) and KOAc (676.3 g, 6.891 mol) in DMF (2.476 L) at 0° C. was slowly added hydrazine hydrate (172.5 g, 167.6 mL, 3.446 mol) over 15 min. The reaction mixture was then stirred at ambient temperature for 2 h, at which stage $^1$H NMR shows complete consumption of the starting material. Reaction mixture was then heated overnight at 110° C. before being allowed to cool to ambient and stirred for another 48 h. The mixture was filtered through a sintered glass funnel to remove the precipitated solid and the filtrate was evaporated under reduced pressure to give a thick liquid. DCM (approx 2 L) was added and the mixture filtered again to remove additional solids that have precipitated. The filtrate was purified through a 1 kg silica gel plug (gradient of DCM/MeOH as an eluent) and the solvent was removed to afford an orange solid which was suspended in acetonitrile and heated at about 70° C. until all the solid went into solution, at which point the solution was allowed to cool to ambient temperature, then to 2° C. The precipitate that formed was isolated by filtration under vacuum, washed with chilled MeCN (~50 mL) and dried to constant mass in a vacuum oven to furnish the title compound as an off-white powder (171.2 g, 41%).

Preparation 2a: 1H-benzo[d][1,2,3]triazol-1-yl 2-amino-6-fluoropyrazolo[1,5-a]pyrimidine-3-carboxylate

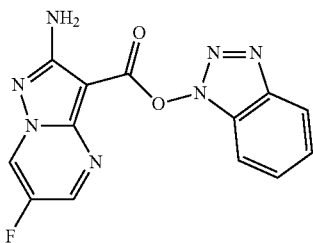

6a

Step 1: allyl 2-amino-6-fluoro-pyrazolo[1,5-a]pyrimidine-3-carboxylate 4a

To a suspension of allyl 3,5-diamino-1H-pyrazole-4-carboxylate 3 (42.72 g, 234.5 mmol) in DMSO (270.8 mL)/Water (270.8 mL), was added p-TsOH hydrate (46.72 g, 245.6 mmol) and 3-(diisopropylamino)-2-fluoro-prop-2-enal (described in Tetrahedron Letters, 33(3), 357-60; 1992) (38.69 g, 223.3 mmol). The reaction mixture was heated to 100° C. for 3 h during which time a solid slowly precipitated out of solution. The orange suspension was allowed to cool down to RT overnight. The solid was filtered, washed with water and dried under vacuum to give allyl 2-amino-6-fluoro-pyrazolo[1,5-a]pyrimidine-3-carboxylate 4a as a sand solid (45.05 g, 85% yield).

Step 2: 2-amino-6-fluoro-pyrazolo[1,5-a]pyrimidine-3-carboxylic acid 5a

To a suspension of allyl 2-amino-6-fluoro-pyrazolo[1,5-a]pyrimidine-3-carboxylate 4a (45 g, 190.5 mmol) in DCM (1.35 L) was added phenylsilane (41.23 g, 46.96 mL, 381.0 mmol), followed by Pd(PPh$_3$)$_4$ (8.805 g, 7.620 mmol). The reaction was stirred at room temperature for 2 h30 min. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-fluoro-pyrazolo[1,5-a]pyrimidine-3-carboxylic acid 5a as a light yellow solid (37.77 g, 100% yield).

In an alternative method, 4-methylbenzenesulfinate (anhydrous, 1.2 eqv, 22.6 g, 127 mmol) was suspended in dry DMSO (20 vol, 500 ml). The stirred mixture was warmed to 30° C. under a nitrogen atmosphere. Upon complete dissolution Pd(PPh$_3$)$_4$ (2 mol %, 2.4 g, 2.1 mmol) was added. The mixture was stirred for 10 min at 25-30° C. after which time a turbid yellow solution was present. Allyl 2-amino-6-fluoro-pyrazolo[1,5-a]pyrimidine-3-carboxylate (25 g, 105.8 mmol) was added portionwise, maintaining the temperature at 25-30° C. Once addition was complete the cloudy solution was stirred until the reaction was complete by HPLC (2-3 hrs). A heavy precipitate formed after 15 minutes post addition of the substrate. The mixture became thicker as the reaction proceeded. The reaction mixture was diluted with water (125 ml) and 2M HCl (66 ml) was added slowly, maintaining the temperature at 25-30° C. The slurry was stirred for 30 minutes, then filtered. The filtration was slow (2 hrs). The resulting solid was washed with water, then dried on the sinter. The solid was slurried in DCM (8 vol) for 1 hr. The solid was filtered (rapid filtration) and washed with DCM. The solid was re-slurried in chloroform (8 vol) for 1 hr. The acid was filtered and dried on the sinter. It was further dried in a vacuum oven at 50° C. for 24 hrs. The product was obtained as an off-white solid (18.6 g, 85%); $^1$H NMR (500 MHz, DMSO-d6) δ 12.14 (1H, brs), 9.31 (1H, dd), 8.69 (1H, m), 6.47 (2H, brS); 19F NMR (500 MHz, DMSO-d6) δ−153.65; MS (ES+) 197.1.

Step 3: 1H-benzo[d][1,2,3]triazol-1-yl 2-amino-6-fluoropyrazolo[1,5-a]pyrimidine-3-carboxylate 6a To a suspension of 2-amino-6-fluoro-pyrazolo[1,5-a]pyrimidine-3-carboxylic acid 5a (20 g, 102.0 mmol) in chloroform (300 mL) was added Et$_3$N (11.35 g, 15.63 mL, 112.2 mmol). The suspension was stirred for ~5 mins and then (benzotriazol-1-yloxy-dimethylamino-methylene)-dimethyl-ammonium Boron Tetrafluoride was added (32.75 g, 102.0 mmol). The suspension was heated to 60° C. for 1 h before the thick suspension was allowed to cool down to RT. The resulting suspension was filtered, washed with chloroform (200 mL) and dried under vacuum overnight to afford the title compound 6a as a light yellow powder (32.5 g, 88%).

Preparation 2b: (6-chlorobenzotriazol-1-yl)-2-amino-6-fluoro-pyrazolo[1,5-a]pyrimidine-3-carboxylate 6a*

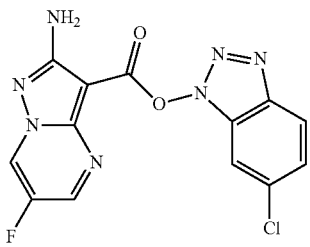

6a*

In a 2.5 L three-necked flask equipped with stirrer bar, condenser, nitrogen line and Hanna temperature probe was charged 2-amino-6-fluoro-pyrazolo[1,5-a]pyrimidine-3-carboxylic acid 5a (60 g, 305.9 mmol), chloroform (900.0 mL) and triethylamine (32.44 g, 44.68 mL, 320.6 mmol). [(6-chlorobenzotriazol-1-yl)oxy-(dimethylamino)methylene]-dimethyl-ammonium (Boron Tetrafluoride Ion (1)) (87.00 g, 244.7 mmol) was added portionwise over 5 mins (internal dropped from 22.7 to 21.5° C. on complete addition). Mixture heated at 60° C. (internal temp) for 2 h, still a cream suspension. Mixture cooled to room temperature then solid collected by filtration, washed well with chloroform (until filtrate runs essentially colourless) and dried by suction to leave product 6a* as a cream solid (82.2 g, 77% yield). $^1$H NMR (500 MHz, DMSO-$d_6$) δ 9.55 (dd, 1H), 8.91 (d, 1H), 8.22 (dd, 1H), 8.09 (dd, 1H), 7.57 (dd, 1H) and 6.87 (s, 2H). MS (ES+) 348.1.

In an alternative method, 2-Amino-6-fluoropyrazolo[1,5-a]pyrimidine-3-carboxylic acid 5a (30 g, 153 mmol) was slurried in acetonitrile (540 ml). Triethylamine (22.5 ml, 153 mmol) was added, followed by [(6-chlorobenzotriazol-1yl)oxy-(dimethylamino)methylene]-dimethylammonium tetrafluoroborate (TCTU, 54.4 g, 153 mmol). The mixture was stirred at room temperature for 2 hrs. The product was isolated by filtration—the filter cake was washed with acetonitrile (2×60 ml) (49.3 g, 93%); $^1$H NMR (500 MHz, DMSO-$d_6$) δ 9.55 (dd, 1H), 8.91 (d, 1H), 8.22 (dd, 1H), 8.09 (dd, 1H), 7.57 (dd, 1H) and 6.87 (s, 2H); 19F NMR (500 MHz, DMSO-d6) δ −150.1; MS (ES+) 348.1.

Preparation 3: 1H-benzo[d][1,2,3]triazol-1-yl 2-amino-6-chloropyrazolo[1,5-a]pyrimidine-3-carboxylate

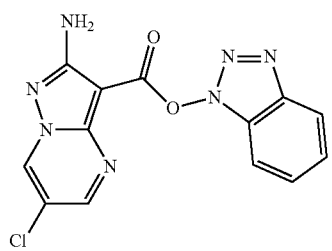

6b

Step 1: allyl 2-amino-6-chloro-pyrazolo[1,5-a]pyrimidine-3-carboxylate 4b

To a suspension of allyl 3,5-diamino-1H-pyrazole-4-carboxylate 3 (1 g, 5.489 mmol) in DMF (5 mL) was added (Z)-2-chloro-3-dimethylamino-prop-2-enylidene]-dimethyl-ammonium hexafluorophosphate (1.683 g, 5.489 mmol), followed by triethylamine (722.1 mg, 994.6 μL, 7.136 mmol). The reaction mixture was heated to 60° C. for 4 h during which time a solid slowly precipitated out of solution. The brown suspension was allowed to cool down to RT. The solid was filtered, washed with water and dried under vacuum to give allyl 2-amino-6-chloro-pyrazolo[1,5-a]pyrimidine-3-carboxylate 4b as a brown solid (1.092 g, 72% yield).

Step 2: 2-amino-6-chloro-pyrazolo[1,5-a]pyrimidine-3-carboxylic acid 5b

To a suspension of allyl 2-amino-6-chloro-pyrazolo[1,5-a]pyrimidine-3-carboxylate 4b (1 g, 3.96 mmol) in DCM (15 mL) was added phenylsilane (856.6 mg, 0.9756 mL, 7.916 mmol), followed by Pd(PPh$_3$)$_4$ (182.9 mg, 0.1583 mmol). The reaction was stirred at room temperature for 7 h. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-chloro-pyrazolo[1,5-a]pyrimidine-3-carboxylic acid 5b as a yellow solid (791 m, 94% yield).

Step 3: 1H-benzo[d][1,2,3]triazol-1-yl 2-amino-6-chloropyrazolo[1,5-a]pyrimidine-3-carboxylate 6b To a solution of 2-amino-6-chloro-pyrazolo[1,5-a]pyrimidine-3-carboxylic acid 2.5b (1.51 g, 7.103 mmol) in chloroform (15.1 mL) was added TBTU boron tetrafluoride (2.737 g, 8.524 mmol) and TEA (862.5 mg, 1.188 mL, 8.524 mmol). The reaction mixture was stirred at 50° C. for one hour. The resulting suspension was filtered, and the solid triturated in ethyl acetate to afford the title compound 6b as a yellow solid (2.05 g, 88%).

Scheme 3-Preparation of butanenitrile intermediates

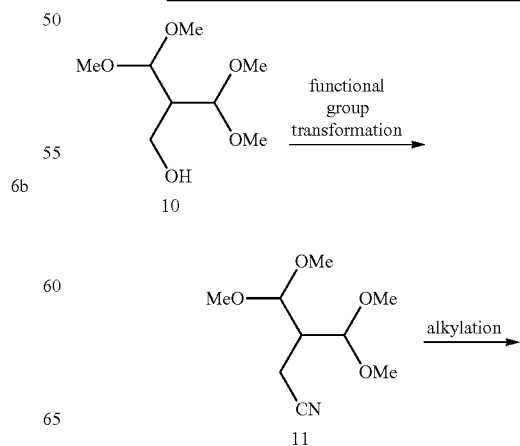

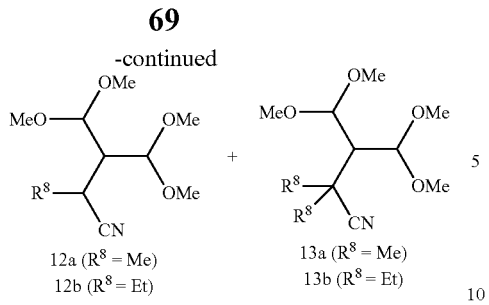

12a (R⁸ = Me)
12b (R⁸ = Et)

13a (R⁸ = Me)
13b (R⁸ = Et)

Step 1:
3-(dimethoxymethyl)-4,4-dimethoxybutanenitrile 11

2-(dimethoxymethyl)-3,3-dimethoxy-propan-1-ol 10 (Journal of the American Chemical Society (1973), 95(26), 8741) (92 g, 473.7 mmol) was dissolved in dry THF (920 mL) and the mixture was cooled down with an ice bath. Triethylamine (143.8 g, 198.1 mL, 1.421 mol) was added at once, followed by dropwise addition of methane sulfonyl chloride (59.69 g, 40.33 mL, 521.1 mmol), over 1 h and keeping the internal temperature below 5° C. The reaction mixture was stirred for 1 h and then allowed to warm to room temperature. The mixture was diluted with ethyl acetate (920 mL) and water (920 mL). The layers were separated and the organic layer was isolated, washed with a saturated solution of NaHCO₃, then brine. The organics were dried over MgSO₄, filtered and evaporated to give [2-(dimethoxymethyl)-3,3-dimethoxypropyl]methanesulfonate as an orange oil (125.31 g, 97%) which was used directly without further purification.

Tetraethylammonium cyanide (142.3 g, 910.8 mmol) was added portionwise over 10 minutes to a solution of [2-(dimethoxymethyl)-3,3-dimethoxypropyl]methanesulfonate (124 g, 455.4 mmol) in MeCN (1.24 L). The reaction mixture was stirred at room temperature for 72 h, then portioned between ethyl acetate (1.24 L) and water (1.24 L). The layers were separated and the organic layer was isolated, washed with brine. The organics were dried over MgSO₄, filtered and evaporated to give 3-(dimethoxymethyl)-4,4-dimethoxybutanenitrile 11 as a dark brown oil (86.1 g).

Step 2: 3-(dimethoxymethyl)-4,4-dimethoxy-2-methylbutanenitrile 12a and 3-(dimethoxymethyl)-4,4-dimethoxy-2,2-dimethylbutanenitrile 13a To a solution of 3-(dimethoxymethyl)-4,4-dimethoxy-butanenitrile 11 (250 mg, 1.205 mmol) in THF (3 mL) at −75° C. was added a solution of iodomethane (513.1 mg, 225.0 μL, 3.615 mmol) in THF (1 ml). A THF solution of (bis(trimethylsilyl)amino)sodium (1.808 mL of 2M, 3.615 mmol) was then added, keeping the temperature below −60° C. After addition, the reaction mixture was stirred at −75° C. for 2 hrs and then slowly quenched with aq. sat. NH₄Cl solution (5 ml). The mixture diluted with water and ether and layers separated. The organic layer was washed with brine, dried (Na₂SO₄) and concentrated in vacuo to afford a yellow oil which was purified by chromatography on silica gel, eluting with a petroleum ether:EtOAc gradient of 100:0 to 80:20. Solvents were concentrated in vacuo to afford a clear oil (194 mg). NMR proved this oil to be a mixture of 80% mono methyl compound 12a with and 20% bis methyl compound 13a. This mixture was used directly in subsequent steps.

Step 3: 3-(dimethoxymethyl)-2-ethyl-4,4-dimethoxybutanenitrile 12b and 3-(dimethoxymethyl)-2-diethyl-4,4-dimethoxybutanenitrile 13b When ethyl iodide was used instead of methyl iodide in a similar procedure to Scheme 3, step 2, above, a mixture of monosubstituted compound 12b and disubstituted compound 13b was isolated and used directly in subsequent steps.

Preparation 4: 1H-benzo[d][1,2,3]triazol-1-yl 2-amino-6-(cyanomethyl)pyrazolo[1,5-a]pyrimidine-3-carboxylate

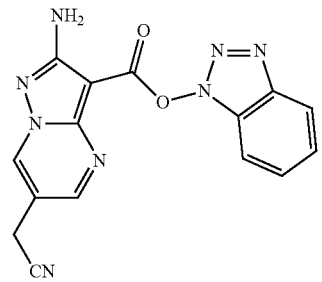

6c

Step 1: allyl 2-amino-6-(cyanomethyl)-pyrazolo[1,5-a]pyrimidine-3-carboxylate 4c To a suspension of allyl 3,5-diamino-1H-pyrazole-4-carboxylate 3 (63.49 g, 348.5 mmol) in a mixture of DMSO (340 mL) and water (340 mL), was added 3-(dimethoxymethyl)-4,4-dimethoxy-butanenitrile (85 g, 418.2 mmol), followed by para-toluene Sulfonic acid hydrate (1) (11.27 g, 59.24 mmol). The reaction mixture was heated to 85° C. and stirred overnight. The reaction mixture was cooled with an ice bath. The mixture was diluted with EtOAc (680 mL) and a saturated aqueous solution of NaHCO₃ (1.36 L). The precipitate was filtered and rinsed with water, then with a mixture of water and EtOAc. The brown solid was dried under vacuum to give allyl 2-amino-6-(cyanomethyl)-pyrazolo[1,5-a]pyrimidine-3-carboxylate 4c as a brown solid (55.94 g, 62% yield).

Step 2: 2-amino-6-(cyanomethyl)-pyrazolo[1,5-a]pyrimidine-3-carboxylic acid 5c

To a suspension of allyl 2-amino-6-(cyanomethyl)-pyrazolo[1,5-a]pyrimidine-3-carboxylate 4c (10.2 g, 39.65 mmol) in DCM (350 mL) was added phenylsilane (8.581 g, 9.773 mL, 79.3 mmol), followed by Pd(PPh₃)₄ (1.5 g, 1.298 mmol). The reaction was stirred at room temperature for 2 h. The reaction mixture was filtered and the solid was washed with DCM and dried under vacuum to provide 2-amino-6-(cyanomethyl)-pyrazolo[1,5-a]pyrimidine-3-carboxylic acid 5c as a yellow solid (8.61 g, 100% yield).

Step 3: 1H-benzo[d][1,2,3]triazol-1-yl 2-amino-6-(cyanomethyl)pyrazolo[1,5-a]pyrimidine-3-carboxylate 6c To a solution of 2-amino-6-(cyanomethyl)-pyrazolo[1,5-a]pyrimidine-3-carboxylic acid 5c (5.11 g, 23.53 mmol) in DCM (51 mL) was added TBTU boron tetrafluoride (9.067 g, 28.24 mmol) and TEA (2.858 g, 3.937 mL, 28.24 mmol). The reaction mixture was stirred at room temperature for one hour. The resulting suspension was filtered, and the solid triturated in hot chloroform to afford the title compound 6c as a beige solid (6.59 g, 84%).

Preparation 5: 1H-benzo[d][1,2,3]triazol-1-yl 2-amino-5-(trifluoromethyl)pyrazolo[1,5-a]pyrimidine-3-carboxylate

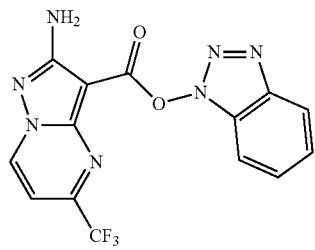

6d

Step 1: allyl 2-amino-5-(trifluoromethyl)pyrazolo[1,5-a]pyrimidine-3-carboxylate 4d 4-methylbenzenesulfonic acid monohydrate (500.1 mg, 467.4 µL, 2.629 mmol) was added to a solution of 4-ethoxy-1,1,1-trifluoro-but-3-en-2-one (200.97 g, 1.195 mol) and ethylene glycol (77.27 g, 69.42 mL, 1.245 mol) in toluene (502.5 mL). The reaction mixture was heated to reflux for 1 h30 min. (oil bath). Then, the reflux was continued with simultaneous distillation of ethanol/toluene. The Dean-Stark was removed and the flask was connected to a distillation apparatus. 3-(1,3-dioxolan-2-yl)-1,1,1-trifluoro-propan-2-one was distilled using a KNF pump (Bp 81° C.) as a light yellow oil (148 g, 67% yield).

3-(1,3-Dioxolan-2-yl)-1,1,1-trifluoro-propan-2-one (55.58 g, 301.9 mmol) and allyl 3,5-diamino-1H-pyrazole-4-carboxylate (55 g, 301.9 mmol) were dissolved in 1,4-dioxane (330 mL). KOH (1.694 g, 30.19 mmol) was added and the yellow suspension was stirred at room temperature for 4 h30 min. The reaction mixture was heated at 90° C. for 16 h. The mixture was cooled down to room temperature. The reaction mixture was concentrated onto silica and purified by column chromatography (CombiFlash Companion XL, 1.5 kg column, 0.5 to 40% EtOAc in DCM) to afford allyl 2-amino-5-(trifluoromethyl)pyrazolo[1,5-a]pyrimidine-3-carboxylate 4d as a bright yellow solid (68 g, 79% yield).

Step 2: 2-amino-5-(trifluoromethyl)pyrazolo[1,5-a]pyrimidine-3-carboxylic acid 5d allyl 2-amino-5-(trifluoromethyl)pyrazolo[1,5-a]pyrimidine-3-carboxylate 4d (67.45 g, 235.7 mmol) in dioxane (670 mL)/water (670 mL) was treated with lithium hydroxide (16.93 g, 707.1 mmol). The resulting light brown suspension was stirred at 70° C. for 1 h45 min. The bright yellow suspension was cooled down to ambient temperature and concentrated in vacuo. The crude mixture was cooled down in a water bath containing ice (T° ~10° C.) and the pH was adjusted to ~3 with 2M HCl. The mixture was stirred for 2 h and the yellow solid was filtered, washed with water and dried on the sinter to give 63.6 g of a wet yellow solid. The solid was dried overnight in a vacuum oven at 40° C. (KNF pump) to afford 2-amino-5-(trifluoromethyl)pyrazolo[1,5-a]pyrimidine-3-carboxylic acid 5d as a yellow solid (55.2 g, 95% yield).

Step 3: 1H-benzo[d][1,2,3]triazol-1-yl 2-amino-5-(trifluoromethyl)pyrazolo[1,5-a]pyrimidine-3-carboxylate 6d Triethylamine (994.9 mg, 1.370 mL, 9.832 mmol) was added to a suspension of 2-amino-5-(trifluoromethyl)pyrazolo[1,5-a]pyrimidine-3-carboxylic acid 5d (2.2 g, 8.938 mmol) in chloroform (22 mL). TBTU (2.870 g, 8.938 mmol) was added to the solution and the reaction mixture was heated at 50° C. for 20 min, during which time a yellow precipitate formed. The reaction mixture was cooled to ambient temperature. The precipitate was isolated by filtration and washed with chloroform to leave the product (benzotriazol-1-yl 2-amino-5-(trifluoromethyl)pyrazolo[1,5-a]pyrimidine-3-carboxylate) 6d as an off white solid (2.8 g, 86% yield).

Preparation 6: 1H-benzo[d][1,2,3]triazol-1-yl 2-amino-5-(2-(dimethylamino)ethoxy)pyrazolo[1,5-a]pyrimidine-3-carboxylate

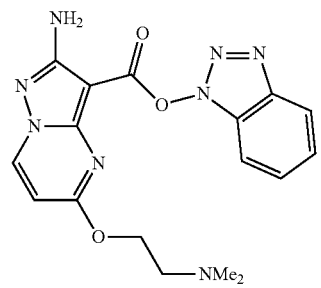

6e

Step 1: allyl 2-amino-5-(2-(dimethylamino)ethoxy)pyrazolo[1,5-a]pyrimidine-3-carboxylate 4e To a suspension of allyl 3,5-diamino-1H-pyrazole-4-carboxylate 3 (1.0 g, 5.4 mmol) and $Cs_2CO_3$ (2.5 g, 7.6 mmol) in EtOH (10 mL) was added methyl prop-2-ynoate (553.0 mg, 586.0 µl, 6.5 mmol), dropwise over 15 minutes and the reaction mixture was stirred overnight at room temperature. The deep orange mixture was filtered. The filtrate was cooled on an ice-bath and ether (100 mL) was slowly added with stirring. The mixture was stirred at 0° C. for 20 minutes by which time a yellow solid had precipitated out of solution. The solid was filtered, further triturated in ether (20 mL) and filtered. The yellow solid was dried to afford allyl 2-amino-5-oxo-4,5-dihydropyrazolo[1,5-a]pyrimidine-3-carboxylate (700 mg, 54% yield).

To a mixture of allyl 2-amino-5-oxo-4H-pyrazolo[1,5-a]pyrimidine-3-carboxylate (1 g, 4.270 mmol) in MeCN (15 mL) was added 2,3,4,6,7,8,9,10-octahydropyrimido[1,2-a]azepine (975.1 mg, 957.9 µL, 6.405 mmol) and benzotriazol-1-yloxy(tripyrrolidin-1-yl)phosphonium (Phosphorus Hexafluoride Ion) (2.666 g, 5.124 mmol). After 5 minutes, 2-dimethylaminoethanol (3.806 g, 4.291 mL, 42.70 mmol) and cesium carbonate (5 g) were added and the mixture was stirred at room temperature for 30 minutes, followed by heating to 50° C. for 30 minutes. After cooling to room temperature the mixture was filtered and the solid was rinsed with acetonitrile. The filtrate was concentrated in vacuo to an orange oil and purified by column chromatography using 4% MeOH/DCM as eluant. Solvent evaporations in vacuo afforded allyl 2-amino-5-(2-(dimethylamino)ethoxy)pyrazolo[1,5-a]pyrimidine-3-carboxylate as a light orange solid. (450 mg, 35% yield).

Step 2: 2-amino-5-(2-(dimethylamino)ethoxy)pyrazolo[1,5-a]pyrimidine-3-carboxylic acid 5e To a solution of phenylsilane (478.5 mg, 550.0 μL, 4.422 mmol) and allyl 2-amino-5-[2-(dimethylamino)ethoxy]pyrazolo[1,5-a]pyrimidine-3-carboxylate (900 mg, 2.948 mmol) in DCM (5 mL) was added palladium triphenylphosphane (170.3 mg, 0.1474 mmol). The reaction mixture was stirred at room temperature for 3 h. Ether was slowly added to the mixture and a white solid precipitated. This solid was filtered off, washed with small amount of diethyl ether and dried to afford pure 2-amino-5-(2-(dimethylamino)ethoxy)pyrazolo[1,5-a]pyrimidine-3-carboxylic acid as off-white solid. (530 mg, 67% yield).

Step 3: 3a,7a-dihydro-1H-benzo[d][1,2,3]triazol-1-yl 2-amino-5-(2-(dimethylamino)ethoxy)pyrazolo[1,5-a]pyrimidine-3-carboxylate 6e To a suspension of 2-amino-5-[2-(dimethylamino)ethoxy]pyrazolo[1,5-a]pyrimidine-3-carboxylic acid (80 mg, 0.3016 mmol) in NMP (1 mL) was added Et₃N (37.24 mg, 51.29 μL, 0.3680 mmol). To the mixture was added TBTU (Boron Tetrafluoride Ion (1)) (109.0 mg, 0.3396 mmol) portionwise over a 5 minutes. The mixture was allowed to stir at room temperature for 20 minutes before being partitioned between ethylacetate and water. The aqueous layer was extracted twice with ethylacetate and the combined organic layers were washed with brine, dried (MgSO₄), and concentrated in vacuo to afford the product 3a,7a-dihydro-1H-benzo[d][1,2,3]triazol-1-yl 2-amino-5-(2-(dimethylamino)ethoxy)pyrazolo[1,5-a]pyrimidine-3-carboxylate as an oil (92 mg, 80% yield).

Example 1

(R)-2-amino-6-fluoro-N-(4-((1-methylpiperidin-3-yl)oxy)pyrimidin-5-yl)pyrazolo[1,5-a]pyrimidine-3-carboxamide

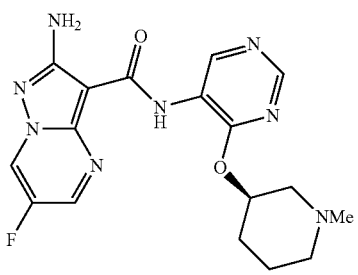

I-A-1

A solution of benzotriazol-1-yl 2-amino-6-fluoro-pyrazolo[1,5-a]pyrimidine-3-carboxylate 6a (125 mg, 0.3990 mmol) and 4-[[(3R)-1-methyl-3-piperidyl]oxy]pyrimidin-5-amine 7a (83.10 mg, 0.3990 mmol) in NMP (2 mL) was heated at 100° C. overnight. The reaction mixture was cooled to RT, passed through a SCX cartridge, eluting with 2M ammonia in methanol. The product fractions were combined, concentrated in vacuo and purified by HPLC. The title product I-A-1 was isolated (60 mg., 38.9%)

The following compounds were prepared according to a methodology similar to the one described in Example 1, starting from the appropriate activated acid 6 a-e and aromatic amine:

(S)-2-amino-6-fluoro-N-(4-((1-methylpiperidin-3-yl)oxy)pyrimidin-5-yl)pyrazolo[1,5-a]pyrimidine-3-carboxamide I-A-2;

(R)-2-amino-6-fluoro-N-(4-(quinuclidin-3-yloxy)pyrimidin-5-yl)pyrazolo[1,5-a]pyrimidine-3-carboxamide I-A-3;

(S)-2-amino-6-fluoro-N-(4-(quinuclidin-3-yloxy)pyrimidin-5-yl)pyrazolo[1,5-a]pyrimidine-3-carboxamide I-A-4;

2-amino-6-fluoro-N-(4-((1-methylpiperidin-4-yl)oxy)pyrimidin-5-yl)pyrazolo[1,5-a]pyrimidine-3-carboxamide I-A-5;

2-amino-6-chloro-N-(4-((1-methylpiperidin-4-yl)oxy)pyrimidin-5-yl)pyrazolo[1,5-a]pyrimidine-3-carboxamide I-A-6;

2-amino-N-(4-((1-methylpiperidin-4-yl)oxy)pyrimidin-5-yl)-5-(trifluoromethyl)pyrazolo[1,5-a]pyrimidine-3-carboxamide I-A-7;

2-amino-6-fluoro-N-(4-((1-(oxetan-3-yl)piperidin-4-yl)oxy)pyrimidin-5-yl)pyrazolo[1,5-a]pyrimidine-3-carboxamide I-A-8;

2-amino-6-chloro-N-(4-((1-(oxetan-3-yl)piperidin-4-yl)oxy)pyrimidin-5-yl)pyrazolo[1,5-a]pyrimidine-3-carboxamide I-A-9;

(R)-2-amino-6-fluoro-N-(4-((1-methylpyrrolidin-3-yl)oxy)pyrimidin-5-yl)pyrazolo[1,5-a]pyrimidine-3-carboxamide I-A-10;

(S)-2-amino-6-fluoro-N-(4-((1-methylpyrrolidin-3-yl)oxy)pyrimidin-5-yl)pyrazolo[1,5-a]pyrimidine-3-carboxamide I-A-11;

2-amino-N-(4-(((1r,4r)-4-(dimethylamino)cyclohexyl)oxy)pyrimidin-5-yl)-6-fluoropyrazolo[1,5-a]pyrimidine-3-carboxamide I-A-12;

2-amino-N-(4-(((1r,4r)-4-(dimethylamino)cyclohexyl)oxy)pyrimidin-5-yl)-5-(trifluoromethyl)pyrazolo[1,5-a]pyrimidine-3-carboxamide I-A-13;

2-amino-6-fluoro-N-(4-isopropoxypyrimidin-5-yl)pyrazolo[1,5-a]pyrimidine-3-carboxamide I-A-14;

2-amino-5-(2-(dimethylamino)ethoxy)-N-(4-isopropoxypyrimidin-5-yl)pyrazolo[1,5-a]pyrimidine-3-carboxamide I-A-15;

2-amino-5-(2-(dimethylamino)ethoxy)-N-(4-methoxypyrimidin-5-yl)pyrazolo[1,5-a]pyrimidine-3-carboxamide I-A-16;

2-amino-6-(cyanomethyl)-N-(4-methoxypyrimidin-5-yl)pyrazolo[1,5-a]pyrimidine-3-carboxamide I-A-17;

2-amino-6-fluoro-N-(4-(4-(4-methylpiperazine-1-carbonyl)piperidin-1-yl)pyrimidin-5-yl)pyrazolo[1,5-a]pyrimidine-3-carboxamide I-A-19;

2-amino-6-fluoro-N-(4-(4-methylpiperazin-1-yl)pyrimidin-5-yl)pyrazolo[1,5-a]pyrimidine-3-carboxamide I-A-20;

2-amino-6-fluoro-N-(5-(4-methylpiperazin-1-yl)pyridazin-4-yl)pyrazolo[1,5-a]pyrimidine-3-carboxamide I-B-1;

2-amino-6-fluoro-N-(5-(4-(oxetan-3-yl)piperazin-1-yl)pyridazin-4-yl)pyrazolo[1,5-a]pyrimidine-3-carboxamide I-B-2;

2-amino-6-fluoro-N-(5-(4-(tetrahydro-2H-pyran-4-yl)piperazin-1-yl)pyridazin-4-yl)pyrazolo[1,5-a]pyrimidine-3-carboxamide I-B-3;

2-amino-6-fluoro-N-(5-(2-methylpyridin-3-yl)pyridazin-4-yl)pyrazolo[1,5-a]pyrimidine-3-carboxamide I-B-4;

2-amino-6-fluoro-N-(5-(4-(4-methylpiperazine-1-carbonyl)piperidin-1-yl)pyridazin-4-yl)pyrazolo[1,5-a]pyrimidine-3-carboxamide I-B-5;

2-amino-N-(5-(4-((3,3-difluoropyrrolidin-1-yl)methyl)piperidin-1-yl)pyridazin-4-yl)-6-fluoropyrazolo[1,5-a]pyrimidine-3-carboxamide I-B-6;
2-amino-6-fluoro-N-(5-(4-((4-methylpiperazin-1-yl)methyl)phenyl)pyridazin-4-yl)pyrazolo[1,5-a]pyrimidine-3-carboxamide I-B-7;
2-amino-6-fluoro-N-(5-(4-(morpholinomethyl)piperidin-1-yl)pyridazin-4-yl)pyrazolo[1,5-a]pyrimidine-3-carboxamide I-B-8;
2-amino-6-fluoro-N-(5-(piperidin-1-yl)pyridazin-4-yl)pyrazolo[1,5-a]pyrimidine-3-carboxamide I-B-9;
2-amino-N-(5-(4-(4-(tert-butyl)piperazine-1-carbonyl)piperidin-1-yl)pyridazin-4-yl)-6-fluoropyrazolo[1,5-a]pyrimidine-3-carboxamide I-B-10;
2-amino-6-fluoro-N-(5-(4-((4-methylpiperazin-1-yl)methyl)piperidin-1-yl)pyridazin-4-yl)pyrazolo[1,5-a]pyrimidine-3-carboxamide I-B-11;
2-amino-6-fluoro-N-(5-morpholinopyridazin-4-yl)pyrazolo[1,5-a]pyrimidine-3-carboxamide I-B-12;
2-amino-6-fluoro-N-(5-(4-(4-methylpiperazine-1-carbonyl)phenyl)pyridazin-4-yl)pyrazolo[1,5-a]pyrimidine-3-carboxamide I-B-13;
2-amino-6-fluoro-N-(6-methyl-5-(4-(4-methylpiperazine-1-carbonyl)piperidin-1-yl)pyridazin-4-yl)pyrazolo[1,5-a]pyrimidine-3-carboxamide I-B-14;
2-amino-6-fluoro-N-(5-(1-methyl-1H-imidazol-5-yl)pyridazin-4-yl)pyrazolo[1,5-a]pyrimidine-3-carboxamide I-B-15;
2-amino-6-fluoro-N-(5-(pyrrolidin-1-yl)pyridazin-4-yl)pyrazolo[1,5-a]pyrimidine-3-carboxamide I-B-16;
2-amino-6-fluoro-N-(5-(o-tolyl)pyridazin-4-yl)pyrazolo[1,5-a]pyrimidine-3-carboxamide I-B-17;
2-amino-N-(5-cyclopropylpyridazin-4-yl)-6-fluoropyrazolo[1,5-a]pyrimidine-3-carboxamide I-B-18;
N-(5-(2-oxa-7-azaspiro[3.5]nonan-7-yl)pyridazin-4-yl)-2-amino-6-fluoropyrazolo[1,5-a]pyrimidine-3-carboxamide I-B-19;
2-amino-6-fluoro-N-(5-(4-fluoropiperidin-1-yl)pyridazin-4-yl)pyrazolo[1,5-a]pyrimidine-3-carboxamide I-B-20;
2-amino-N-(5-(4-(3,3-difluoroazetidine-1-carbonyl)piperidin-1-yl)pyridazin-4-yl)-6-fluoropyrazolo[1,5-a]pyrimidine-3-carboxamide I-B-21;
2-amino-6-fluoro-N-(5-(4-(3-fluoroazetidine-1-carbonyl)piperidin-1-yl)pyridazin-4-yl)pyrazolo[1,5-a]pyrimidine-3-carboxamide I-B-22;
2-amino-6-fluoro-N-(5-(4-(methylsulfonyl)piperidin-1-yl)pyridazin-4-yl)pyrazolo[1,5-a]pyrimidine-3-carboxamide I-B-23;
2-amino-6-fluoro-N-(5-(4-(4-methylpiperazin-1-yl)piperidin-1-yl)pyridazin-4-yl)pyrazolo[1,5-a]pyrimidine-3-carboxamide I-B-24;
2-amino-6-fluoro-N-(3-(4-(oxetan-3-yl)piperazin-1-yl)pyridin-4-yl)pyrazolo[1,5-a]pyrimidine-3-carboxamide I-C-1;
2-amino-6-fluoro-N-(3-(4-methylpiperazin-1-yl)pyridin-4-yl)pyrazolo[1,5-a]pyrimidine-3-carboxamide I-C-2;
2-amino-6-fluoro-N-(3-(4-(4-methylpiperazine-1-carbonyl)piperidin-1-yl)pyridin-4-yl)pyrazolo[1,5-a]pyrimidine-3-carboxamide I-C-3;
2-amino-N-(3-methoxypyridin-4-yl)-5-(trifluoromethyl)pyrazolo[1,5-a]pyrimidine-3-carboxamide I-C-4;
2-amino-6-fluoro-N-(2'-methyl-[3,3'-bipyridin]-4-yl)pyrazolo[1,5-a]pyrimidine-3-carboxamide I-C-5;
2-amino-6-fluoro-N-(3'-methyl-[3,4'-bipyridin]-4-yl)pyrazolo[1,5-a]pyrimidine-3-carboxamide I-C-6;

2-amino-6-fluoro-N-(3-(4-(methylsulfonyl)piperidin-1-yl)pyridin-4-yl)pyrazolo[1,5-a]pyrimidine-3-carboxamide I-C-10; and
2-amino-6-fluoro-N-(3-(pyrrolidin-1-yl)pyridin-4-yl)pyrazolo[1,5-a]pyrimidine-3-carboxamide I-C-11.

Example 2

N-(4-((4s,6r)-1-azaspiro[3.3]heptan-6-yloxy)pyrimidin-5-yl)-2-amino-6-fluoropyrazolo[1,5-a]pyrimidine-3-carboxamide

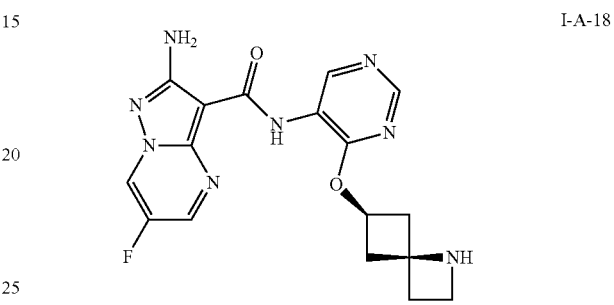

I-A-18

A solution of (4s,6r)-tert-butyl 6-((5-aminopyrimidin-4-yl)oxy)-1-azaspiro[3.3]heptane-1-carboxylate (prepared according to a procedure similar to Example 1) (242 mg, 0.7899 mmol) and benzotriazol-1-yl 2-amino-6-fluoro-pyrazolo[1,5-a]pyrimidine-3-carboxylate (247.4 mg, 0.7899 mmol) in NMP (2.5 mL) was heated at 100° C. for 72 h. The reaction mixture was filtered through a SCX cartridge, eluting with a 2M NH₃ in MeOH. The appropriate fractions were concentrated in vacuo and the residue was dissolved in DCM (10 mL). TFA (2 mL, 26 mmol) was added and the mixture was stirred at RT for 2 h, then concentrated in vacuo. The residue was purified using preparative HPLC (32 mg, 6.4%).

Example 3

2-amino-6-fluoro-N-(3-(4-(4-(oxetan-3-yl)piperazine-1-carbonyl)piperidin-1-yl)pyridin-4-yl)pyrazolo[1,5-a]pyrimidine-3-carboxamide

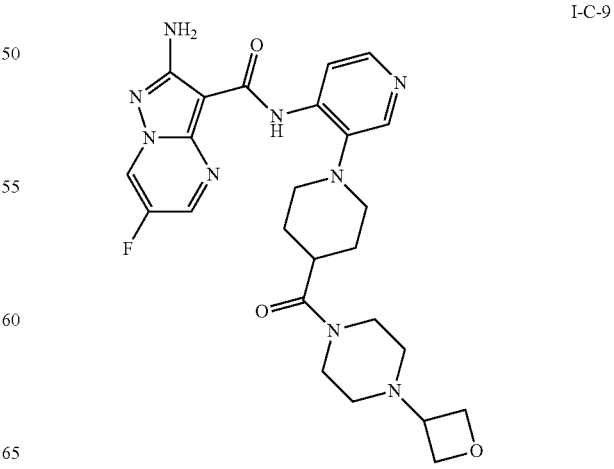

I-C-9

Step 1: 1-(4-(2-amino-6-fluoropyrazolo[1,5-a]pyrimidine-3-carboxamido)pyridin-3-yl)piperidine-4-carboxylic acid To a suspension of tert-butyl 1-[4-[(2-amino-6-fluoropyrazolo[1,5-a]pyrimidine-3-carbonyl)amino]-3-pyridyl]piperidine-4-carboxylate trifluoroacetic acetate (prepared according to a methodology similar to the one described in Example 1) (101 mg, 0.1773 mmol) in DCM (5 mL) was added TFA (1 mL, 12.98 mmol). The mixture was stirred at room temperature for 20 hours. The solvent was removed in vacuo and the residue azeotroped with DCM (×2) and diethyl ether (×2) to give title compound as a beige solid (98% Yield, di-TFA salt). $^1$H NMR (500 MHz, DMSO) δ 11.10 (s, 1H), 9.58 (dd, 1H), 8.91 (d, 1H), 8.86 (d, 1H), 8.68 (s, 1H), 8.56 (d, 1H), 6.92 (s, 2H), 3.10 (d, 2H), 2.99-2.82 (m, 2H), 2.53-2.50 (m, 1H), 2.15-1.93 (m, 4H); $^{19}$F NMR (471 MHz, DMSO) δ −74.10, −151.83; LC-MS ES+: 400.0.

Step 2: 2-amino-6-fluoro-N-(3-(4-(4-(oxetan-3-yl)piperazine-1-carbonyl)piperidin-1-yl)pyridin-4-yl)pyrazolo[1,5-a]pyrimidine-3-carboxamide I-C-9

A mixture of 1-[4-[(2-amino-6-fluoro-pyrazolo[1,5-a]pyrimidine-3-carbonyl)amino]-3-pyridyl]piperidine-4-carboxylic acid (ditrifluoroacetate) (36 mg, 0.05738 mmol), 1-(oxetan-3-yl)piperazine (20.41 mg, 0.1435 mmol), Et$_3$N (23.22 mg, 31.98 uL, 0.2295 mmol) and TBTU tetrafluoroborate (27.64 mg, 0.08607 mmol) in DMF (1 mL) was stirred at ambient temperature for 66 hours. The crude reaction mixtures was purified directly by reverse phase preparative HPLC (Waters Sunfire C18, 10 μM, 100 Å column) to give the title compound as a beige solid. (17 mg, 39%/TFA salt). $^1$H NMR (500 MHz, DMSO) δ 11.16 (s, 1H), 9.57 (dd, 1H), 9.17 (d, 1H), 8.92 (d, 1H), 8.65 (s, 1H), 8.57 (d, 1H), 6.92 (s, 2H), 4.69 (d, 4H), 4.06 (br s, 2H), 3.80 (br s, 4H), 3.12 (dd, 2H), 3.01-2.80 (m, 6H), 2.15 (qd, 2H), 1.82 (d, 2H); $^{19}$F NMR (471 MHz, DMSO) δ −73.97, −151.62; LC-MS ES+: 524.2, ES−522.2.

The following compounds were prepared according to a methodology similar to the one described in Example 3, starting from the appropriate aromatic amine:

N-(3-(4-(1,4-diazabicyclo[3.2.2]nonane-4-carbonyl)piperidin-1-yl)pyridin-4-yl)-2-amino-6-fluoropyrazolo[1,5-a]pyrimidine-3-carboxamide I-C-7; and 2-amino-6-fluoro-N-(3-(4-(4-(pyrrolidin-1-yl)piperidine-1-carbonyl)piperidin-1-yl)pyridin-4-yl)pyrazolo[1,5-a]pyrimidine-3-carboxamide I-C-8.

The synthesis of the novel intermediates below was required for the preparation of some of the compounds described in this patent application.

Preparation 7: (R)-4-((1-methylpiperidin-3-yl)oxy)pyrimidin-5-amine

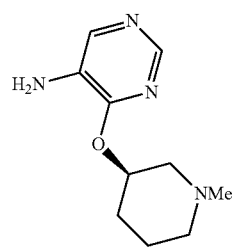

7a

Step 1: (R)-4-chloro-6-((1-methylpiperidin-3-yl)oxy)pyrimidin-5-amine

Sodium t-butoxide (586.0 mg, 6.098 mmol) was added to a solution of 4,6-dichloropyrimidin-5-amine (500 mg, 3.049 mmol) and (3R)-1-methylpiperidin-3-ol (351.2 mg, 3.049 mmol) in THF (25.00 mL) at RT. The reaction mixture was heated at 70° C. overnight. The reaction mixture was quenched with 1 mL water and concentrated in vacuo. The residue was extracted with DCM and the combined organic extract were dried and concentrated in vacuo to afford (R)-4-chloro-6-((1-methylpiperidin-3-yl)oxy)pyrimidin-5-amine which was used in next step without further purification.

Step 2: (R)-4((1-methylpiperidin-3-yl)oxy)pyrimidin-5-amine 7a (R)-4-chloro-6-((1-methylpiperidin-3-yl)oxy)pyrimidin-5-amine was dissolved in MeOH (15.0 mL) and Pd/C 10% (324.5 mg, 0.3049 mmol) was added and the reaction mixture stirred under a hydrogen atmosphere for 2 h. The reaction vessel was evacuated and flushed with nitrogen (3×), filtered through a celite pad washing with methanol followed by ethyl acetate. The combined filtrates were concentrated in vacuo to leave the title product 7a as a colourless oil (631 mg, 99%).

The following amines were prepared according to a methodology similar to the one described in Preparation 7:

(S)-6-((1-methylpiperidin-3-yl)oxy)pyrimidin-5-amine 7b;

(R)-6-(quinuclidin-3-yloxy)pyrimidin-5-amine 7c;

(S)-6-(quinuclidin-3-yloxy)pyrimidin-5-amine 7d;

4-((1-methylpiperidin-4-yl)oxy)pyrimidin-5-amine 7e;

4-((1-(oxetan-3-yl)piperidin-4-yl)oxy)pyrimidin-5-amine 7f;

(4s,6r)-tert-butyl 6-((5-aminopyrimidin-4-yl)oxy)-1-azaspiro[3.3]heptane-1-carboxylate 7g;

(R)-4-((1-methylpyrrolidin-3-yl)oxy)pyrimidin-5-amine 7h;

(S)-4-((1-methylpyrrolidin-3-yl)oxy)pyrimidin-5-amine 7i;

4-(((1r,4r)-4-(dimethylamino)cyclohexyl)oxy)pyrimidin-5-amine 7j;

4-isopropoxypyrimidin-5-amine 7k; and (1-(5-aminopyrimidin-4-yl)piperidin-4-yl)(4-methylpiperazin-1-yl)methanone 7p; and 4-(4-methylpiperazin-1-yl)pyrimidin-5-amine 7gg.

Preparation 8.1: 3-(4-(oxetan-3-yl)piperazin-1-yl)pyridin-4-amine 7l

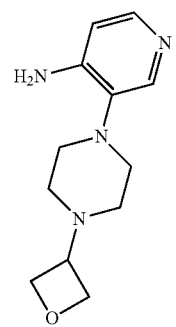

Step 1: 1-(4-nitro-1-oxido-pyridin-1-ium-3-yl)-4-(oxetan-3-piperazine

A mixture of 3-bromo-4-nitro-1-oxido-pyridin-1-ium (500 mg, 2.283 mmol) and 1-(oxetan-3-yl)piperazine (649.3 mg, 4.566 mmol) in EtOH (10 mL) were heated at reflux for 17 hours. The reaction was cooled to ambient temperature and the solvent removed in vacuo. The residue was passed through a 25 g SCX-2 cartridge (pre-wetted with MeOH), eluting with 2M $NH_3$ in MeOH/DCM. The solvents were removed in vacuo and the residue purified by column chromatography (ISCO Companion, 40 g column, eluting with 0 to 10% MeOH/DCM, loaded in DCM) to give 1-(4-nitro-1-oxido-pyridin-1-ium-3-yl)-4-(oxetan-3-yl)piperazine as an orange solid (553 mg, 86% Yield).

Step 2: 3-(4-(oxetan-3-yl)piperazin-1-yl)pyridin-4-amine 71

1-(4-nitro-1-oxido-pyridin-1-ium-3-yl)-4-(oxetan-3-yl)piperazine (553 mg, 1.973 mmol) in MeOH (15 mL)/EtOAc (25 mL) was passed through the H-cube apparatus to hydrogenate over raney nickel at 20° C. and full $H_2$ mode, flow rate 1 ml/min. The solvent was removed in vacuo to give the title compound 71 as an orange solid (462 mg, 100% Yield).

The following amines were prepared according to a methodology similar to the one described in Preparation 8.1:

3-(4-methylpiperazin-1-yl)pyridin-4-amine 7m;

(1-(4-aminopyridin-3-yl)piperidin-4-yl)(1-methylpiperidin-4-yl)methanone 7n;

tert-butyl 1-(4-aminopyridin-3-yl)piperidine-4-carboxylate 7w;

3-(4-(methylsulfonyl)piperidin-1-yl)pyridin-4-amine 7hh; and 3-(pyrrolidin-1-yl)pyridin-4-amine 7ii.

Preparation 8.2: 2'-methyl-[3,3'-bipyridin]-4-amine

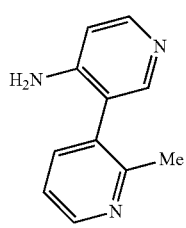

7q

A mixture of (4-amino-3-pyridyl)boronic acid hydrochloric acid (100 mg, 0.5734 mmol), 3-bromo-2-methyl-pyridine (108.5 mg, 0.64 mmol), $NaHCO_3$ (860 μL of 2 M, 1.72 mmol) and palladium triphenylphosphane (66.26 mg, 0.05734 mmol) in dioxane (4 mL) was heated at 105° C. for 12 h. The mixture was then cooled to room temperature and partitioned between DCM and water. The organic layer was filtered through a SCX column, eluting with a 2M solution of $NH_3$ in MeOH. The eluate was concentrated in vacuo to give the title compound 7q (60 mg, 56% Yield).

The following amines were prepared according to a methodology similar to the one described in Preparation 8.2: 3'-methyl-[3,4'-bipyridin]-4-amine 7r.

Preparation 9.1: 5-(4-methylpiperazin-1-yl)pyridazin-4-amine

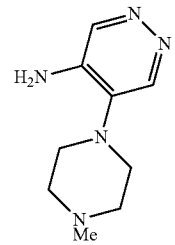

7o

Step 1: 3,4-dichloro-5-(4-methylpiperazin-1-yl)pyridazine 3,4,5-Trichloropyridazine (3 g, 16.36 mmol) was dissolved in dry NMP (18 mL) and cooled in an ice-bath. DIPEA (2.326 g, 3.135 mL, 18 mmol) was added, followed, dropwise, by 1-methylpiperazine (1.721 g, 1.906 mL, 17.18 mmol). The resulting mixture was stirred at RT overnight. The reaction mixture was concentrated under reduced pressure to give an brown solid which was partitioned between 10% MeOH in DCM and saturated $NaHCO_3$. The aqueous layer was extracted with further 10% MeOH in DCM (5×20 mL) and the combined organics were dried over $Na_2SO_4$, filtered and concentrated under reduced pressure to give a brown oil which was purified by column chromatography (7.5% MeOH in DCM, ~300 mL silica, loaded in DCM) to provide 3,4-dichloro-5-(4-methylpiperazin-1-yl)pyridazine as a light yellow solid (2.36 g, 58% Yield).

Step 2: [4-chloro-5-(4-methylpiperazin-1-yl)pyridazin-3-yl]hydrazine 3,4-Dichloro-5-(4-methylpiperazin-1-yl)pyridazine (500 mg, 2.023 mmol) was placed in a microwave tube and hydrazine monohydrate (1.772 g, 1.717 mL, 35.40 mmol) was added. The resulting suspension was stirred at 100° C. for ~10 mins. The brown reaction mixture was allowed to cool to RT, whereupon solid started to precipitate. The suspension was sonicated and the suspended solid was collected by filtration. This material was dissolved in water, basified with saturated $NaHCO_3$ and partitioned with 10% MeOH in DCM. The aqueous layer was extracted with further 10% MeOH in DCM (6×10 mL) and the combined organics were dried over $Na_2SO_4$, filtered and concentrated under reduced pressure to give a yellow solid. This material was sonicated in ether and the suspended solid was collected by filtration to give [4-chloro-5-(4-methylpiperazin-1-yl)pyridazin-3-yl]hydrazine as an ochre powder (155.9 mg, 32% Yield).

Step 3: 4-chloro-5-(4-methylpiperazin-1-yl)pyridazine

[4-Chloro-5-(4-methylpiperazin-1-yl)pyridazin-3-yl]hydrazine (145 mg, 0.5974 mmol) and copper sulfate pentahydrate (522.1 mg, 2.091 mmol) were dissolved in water (9 mL) and stirred at 95° C. for ~30 minutes. The brown suspension was allowed to cool and 15 wt % NaOH (2 mL) was added. The resulting suspension was heated to 95° C. for ~5 mins, allowed to cool to RT and filtered through a pre-wetted (10% MeOH in DCM) celite cartridge (10 g). The cartridge was washed with 10% MeOH in DCM and the filtrate was partitioned with water. The aqueous layer was extracted with further 10% MeOH in DCM (3×10 mL) and the combined organics were dried over $Na_2SO_4$, filtered and concentrated under reduced pressure. The residue was purified by column chromatography (7.5% MeOH/1% NH4OH in DCM, ~75 mL silica) to give 4-chloro-5-(4-methylpiperazin-1-yl)pyridazine as an off-white solid (100.6 mg, 79% Yield).

Step 4: 5-(4-methylpiperazin-1-yl)pyridazin-4-amine 7o 4-chloro-5-(4-methylpiperazin-1-yl)pyridazine (720 mg, 3.385 mmol), tert-butyl carbamate (1.982 g, 16.92 mmol), sodium tert-butoxide (1.659 g, 17.26 mmol), BrettPhos pre-catalyst (269.7 mg, 0.3385 mmol) and BrettPhos (181.7 mg, 0.3385 mmol) were placed in a Schlenk tube and degassed by vacuum/nitrogen cycles (×5). Dry toluene (14.4 mL) was added and the resulting mixture was placed into a pre-heated block at 100° C. The mixture was stirred at 100° C. overnight. The reaction mixture was partitioned between 10% MeOH in DCM and saturated $NH_4Cl$. The aqueous layer was extracted with further 10% MeOH in DCM (3×10 mL) and the combined organics were dried over $Na_2SO_4$, filtered and concentrated under reduced pressure to give an orange gum which was purified by column chromatography (7.5% MeOH/1% $NH_4OH$ in DCM, ~100 mL silica) to give an orange foam (618.8 mg, 62% Yield). The material was dissolved in DCM (5 mL) and cooled in an ice-bath. TFA (5 mL) was added slowly and the resultant solution was stirred at 0° C. for ~20 mins and at RT for ~90 mins. The reaction mixture was concentrated under reduced pressure. The residue was dissolved in MeOH and added to a pre-wetted (MeOH)SCX-2 cartridge (25 g), eluting with 2M $NH_3$ in MeOH. The light yellow eluate was concentrated under reduced pressure to give a light yellow gum which was purified by column chromatography (9% MeOH/1% $NH_4OH$ in DCM, ~100 mL silica) to give 5-(4-methylpiperazin-1-yl)pyridazin-4-amine 7o as a light yellow solid (286.3 mg, 44% Yield).

The following amines were prepared according to a methodology similar to the one described in Preparation 9.1:

5-(4-(oxetan-3-yl)piperazin-1-yl)pyridazin-4-amine 7s;

5-(4-(tetrahydro-2H-pyran-4-yl)piperazin-1-yl)pyridazin-4-amine 7t;

(1-(5-aminopyridazin-4-yl)piperidin-4-yl)(4-methylpiperazin-1-yl)methanone 7u;

(1-(5-aminopyridazin-4-yl)piperidin-4-yl)(4-(tert-butyl)piperazin-1-yl)methanone 7x;

(1-(5-amino-3-methylpyridazin-4-yl)piperidin-4-yl)(4-methylpiperazin-1-yl)methanone 7y;

5-(pyrrolidin-1-yl)pyridazin-4-amine 7jj;

5-(2-oxa-7-azaspiro[3.5]nonan-7-yl)pyridazin-4-amine 7kk;

5-(4-fluoropiperidin-1-yl)pyridazin-4-amine 7ll;

(1-(5-aminopyridazin-4-yl)piperidin-4-yl)(3,3-difluoroazetidin-1-yl)methanone 7 mm;

(1-(5-aminopyridazin-4-yl)piperidin-4-yl)(3-fluoroazetidin-1-yl)methanone 7nn;

5-(4-(methylsulfonyl)piperidin-1-yl)pyridazin-4-amine 7oo; and 5-(4-(4-methylpiperazin-1-yl)piperidin-1-yl)pyridazin-4-amine 7 pp.

Preparation 9.2: 5-(2-methylpyridin-3-yl)pyridazin-4-amine

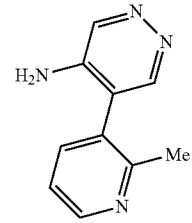

7v

A mixture of 5-chloropyridazin-4-amine (50 mg, 0.386 mmol), (2-methyl-3-pyridyl)boronic acid (63.43 mg, 0.463 mmol), palladium triphenylphosphane (22.3 mg, 0.0193 mmol) and $Na_2CO_3$ (386 µL of 2M, 0.772 mmol) in dioxane (2 mL) was heated at 140° C. for 1 h. The mixture was then cooled to room temperature and partitioned between DCM and water. The organic layer was filtered through a SCX column, eluting with a 2M solution of $NH_3$ in MeOH. The eluate was concentrated in vacuo to give the title compound 7v (72 mg, 100% Yield).

The following amines were prepared according to a methodology similar to the one described in Preparation 9.2:

(4-(5-aminopyridazin-4-yl)phenyl)(4-methylpiperazin-1-yl)methanone 7z;

5-(4-((4-methylpiperazin-1-yl)methyl)phenyl)pyridazin-4-amine 7aa;

5-(1-methyl-1H-imidazol-5-yl)pyridazin-4-amine 7qq;

5-(o-tolyl)pyridazin-4-amine 7rr; and 5-cyclopropylpyridazin-4-amine 7ss.

Preparation 9.3: 5-(4-((3,3-difluoropyrrolidin-1-yl)methyl)piperidin-1-yl)pyridazin-4-amine

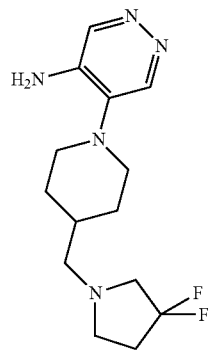

7bb

Step 1: tert-butyl 4((3,3-difluoropyrrolidin-1-yl)methyl)piperidine-1-carboxylate A mixture of 3,3-difluoropyrrolidine hydrochloride (965 mg, 6.722 mmol), tert-butyl 4-formylpiperidine-1-carboxylate (1.720 g, 8.066 mmol), DIPEA (955.6 mg, 1.288 mL, 7.394 mmol) and crushed 4A MS (965 mg) in DCE (30 mL)

were stirred at ambient temperature for 3 hours. NaBH(OAc)$_3$ (2.848 g, 13.44 mmol) was added and the reaction stirred at ambient temperature for a further 16 hours. The mixture was filter through Celite (washing with DCM) and the filtrate concentrated in vacuo. The residue was purified by column chromatography (ISCO Companion, 80 g column, eluting with 0 to 10% MeOH/DCM, loaded in DCM) to give the sub-title product as a colourless oil that was used directly into next step without further purification. LC-MS ES+: 305.1.

Step 2:
4-((3,3-difluoropyrrolidin-1-yl)methyl)piperidine

TFA (766.5 mg, 517.9 µL, 6.722 mmol) was added to a stirred solution of tert-butyl 4-[(3,3-difluoropyrrolidin-1-yl)methyl]piperidine-1-carboxylate (2.046 g, 6.722 mmol) in DCM (15 mL) and the reaction stirred at ambient temperature for 66 hours. The solvent was removed in vacuo and the residue azeotroped with DCM (×2) and ether (×2). The residue was passed through a 50 g SCX-2 cartridge and washed with MeOH/DCM mixtures. The product was eluted by washing the cartridge with 2M NH$_3$ in MeOH/DCM mixtures. The solvent was removed in vacuo to give the sub-title compound as a pale yellow solid (1.15 g, 84% Yield). $^1$H NMR (500 MHz, DMSO) δ 2.89 (dt, 2H), 2.82 (t, 2H), 2.64 (t, 2H), 2.42 (td, 2H), 2.32-2.09 (m, 4H), 1.67-1.58 (m, 2H), 1.52-1.44 (m, 1H), 0.95 (dtd, 2H); $^{19}$F NMR (471 MHz, DMSO) δ −90.80; LC-MS ES+: 205.1.

Step 3: 5-(4-((3,3-difluoropyrrolidin-1-yl)methyl)piperidin-1-yl)pyridazin-4-amine 7bb A mixture of 5-chloropyridazin-4-amine (50 mg, 0.3860 mmol), 4-[(3,3-difluoropyrrolidin-1-yl)methyl]piperidine (197.1 mg, 0.9650 mmol) in NMP (10 mL) were heated under microwave conditions at 170° C. for 7 hours. The reaction was passed through a 10 g SCX-2 cartridge and washed with MeOH/DCM mixtures. The product was eluted by washing the cartridge with 2M NH$_3$ in MeOH/DCM mixtures. The solvent was removed in vacuo and the residue was purified by column chromatography (ISCO Companion, 12 g column, eluting with 0 to 10% MeOH/DCM, loaded in DCM) to give the sub-title product as a beige solid (27 mg, 23% Yield). $^1$H NMR (500 MHz, DMSO) δ 8.46 (d, 1H), 8.41 (s, 1H), 5.85 (s, 2H), 3.20 (d, 2H), 2.87 (t, 2H), 2.69 (t, 2H), 2.59 (td, 2H), 2.34 (d, 2H), 2.24 (tt, 2H), 1.83-1.74 (m, 2H), 1.65-1.53 (m, 1H), 1.43-1.30 (m, 2H); $^{19}$F NMR (471 MHz, DMSO) δ −90.81; LC-MS ES+: 298.1, ES−: 296.1.

The following amines were prepared according to a methodology similar to the one described in Preparation 9.3:
5-morpholinopyridazin-4-amine 7 cc;
5-(4-((4-methylpiperazin-1-yl)methyl)piperidin-1-yl)pyridazin-4-amine 7dd;
5-(piperidin-1-yl)pyridazin-4-amine 1ee; and
5-(4-(morpholinomethyl)piperidin-1-yl)pyridazin-4-amine 7ff.

Preparation 10: 1-(tetrahydro-2H-pyran-4-yl)-1H-imidazol-5-amine

Tetrahydropyran-4-amine (451 mg, 4.459 mmol) was added to a stirred solution of ethyl N-(cyanomethyl)formimidate (500 mg, 4.459 mmol) in DCM (5 mL) and the reaction was heated at reflux for 1 hour. The reaction was cooled to ambient temperature then passed through a 25 g SCX-2 cartridge and washed with MeOH/DCM mixtures. The product was eluted by washing the cartridge with 2M NH$_3$ in MeOH/DCM mixtures. The solvent was removed in vacuo and the residue tritruated from DCM/Et$_2$O and the resultant precipitate isolated by filtration to give the sub-title compound as a grey solid (123 mg, 17% Yield). MS (ES+) 168.1.

The following aminoimidazoles intermediates were synthesized according to Preparation 10:
1-cyclopropyl-1H-imidazol-5-amine:

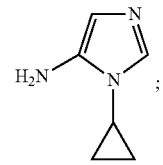

1-(pyridin-3-yl)-1H-imidazol-5-amine:

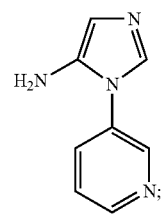

and
1-phenyl-1H-imidazol-5-amine:

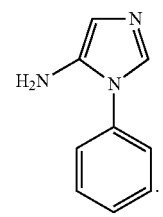

Example 4

2-amino-6-fluoro-N-(1-(tetrahydro-2H-pyran-4-yl)-1H-imidazol-5-yl)pyrazolo[1,5-a]pyrimidine-3-carboxamide (Compound I-D-4)

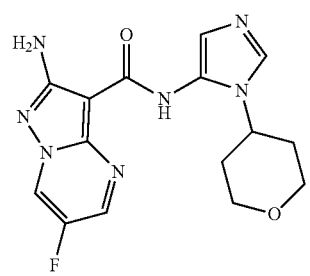

(6-chlorobenzotriazol-1-yl) 2-amino-6-fluoro-pyrazolo[1,5-a]pyrimidine-3-carboxylate (120.1 mg, 0.3454 mmol) and 3-tetrahydropyran-4-ylimidazol-4-amine (75 mg, 0.314 mmol) (prepared according to a procedure similar to Preparation 10) were suspended in NMP (1 mL) and stirred at 100° C. for 19 hours. The reaction was cooled to ambient temperature and purified by passing the crude reaction mixture through a 10 g SCX-2 cartridge (pre-washed with MeOH). The cartridge was washed with DCM/MeOH mixtures then the product eluted with 2M NH₃ in MeOH/DCM mixtures. The solvent was removed in vacuo and the material was purified by fractionlynx. The clean fractions were freeze-dried to give title compound 2-amino-6-fluoro-N-(1-(tetrahydro-2H-pyran-4-yl)-1H-imidazol-5-yl)pyrazolo[1,5-a]pyrimidine-3-carboxamide as a beige solid (21.1 mg, 19% Yield). MS (ES+) 346.1.

The following compounds were successfully prepared using a procedure similar to Example 4:
2-amino-N-(1-benzyl-1H-imidazol-5-yl)-6-(cyanomethyl) pyrazolo[1,5-a]pyrimidine-3-carboxamide (Compound I-D-1);
2-amino-6-fluoro-N-(1-phenyl-1H-imidazol-5-yl)pyrazolo [1,5-a]pyrimidine-3-carboxamide (Compound I-D-2);
2-amino-N-(1-cyclopropyl-1H-imidazol-5-yl)-6-fluoropyrazolo[1,5-a]pyrimidine-3-carboxamide (Compound I-D-3); and
2-amino-6-fluoro-N-(1-(pyridin-3-yl)-1H-imidazol-5-yl) pyrazolo[1,5-a]pyrimidine-3-carboxamide (Compound I-D-5).

Example 5

2-amino-6-fluoro-N-(2-methyl-1-phenyl-1H-imidazol-5-yl)pyrazolo[1,5-a]pyrimidine-3-carboxamide (Compound I-D-6)

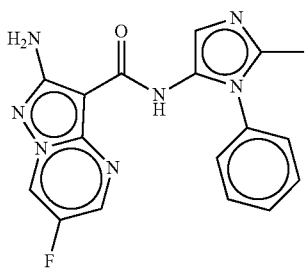

Step 1: benzyl(2-methyl-1-phenyl-1H-imidazol-5-yl) carbamate

To a suspension of 2-methyl-3-phenyl-imidazole-4-carboxylic acid (Hydrochloric Acid (1)) (500 mg, 2.095 mmol) in dioxane (6 mL) was sequentially added dppa (634.1 mg, 0.4966 mL, 2.304 mmol) and Et₃N (466.4 mg, 0.6424 mL, 4.609 mmol). The mixture was heated at 90° C. for 5 mins before benzyl alcohol (0.651 mL, 6.291 mmol) was added. The reaction mixture was heated at 90° C. for 1 h, then partitioned between water and EtOAc. The combined organics were washed with brine, dried (MgSO₄) and concentrated in vacuo to give a brown oil. The crude product was purified by chromatography on silica gel eluting with 1% MeOH in EtOAc (0.1% NH₄OH) to give benzyl(2-methyl-1-phenyl-1H-imidazol-5-yl)carbamate as a yellow oil. (75 mg, 9.5%). MS (ES+) 309.3.

Step 2: 2-methyl-1-phenyl-1H-imidazol-5-amine

To a mixture of benzyl N-(2-methyl-3-phenyl-imidazol-4-yl)carbamate (510 mg, 1.659 mmol) and Pd on C, wet, Degussa (176.6 mg, 0.1659 mmol) was added methanol (10 mL). The reaction was hydrogenated (balloon pressure) for 2 h before the catalyst was filtered off and the filtrate concentrated in vacuo yielding 2-methyl-1-phenyl-1H-imidazol-5-amine as a yellow oil that is immediately used in next step without further purification. MS (ES+) 174.4.

Step 3: 2-cyano-N-(2-methyl-1-phenyl-1H-imidazol-5-yl)acetamide

To a solution of 2-methyl-1-phenyl-1H-imidazol-5-amine (250 mg, 1.44 mmol) in DCM (7.5 mL) was sequentially added DIPEA (1.006 mL, 5.776 mmol) and cyanoacetic acid (184.2 mg, 2.165 mmol). The mixture was cooled on an ice bath then 3-(ethyliminomethyleneamino)-N,N-dimethyl-propan-1-amine; hydrochloride (415.0 mg, 2.165 mmol) was added. The reaction mixture was stirred at 0° C. for 30 mins and then allowed to warm to room temperature and stirred overnight. The reaction mixture was partitioned between DCM and water. Combined organic extract was dried (MgSO₄) and concentrated in vacuo to give a redish oil which was purified by chromatography on silica gel, eluting with 5% MeOH in DCM (0.5% NH₄OH) to give 2-cyano-N-(2-methyl-1-phenyl-1H-imidazol-5-yl)acetamide as a redish oil/solid. (105 mg, 32.3%). MS (ES+) 242.1.

Step 4: 3-amino-4,4,4-trichloro-2-cyano-N-(2-methyl-1-phenyl-1H-imidazol-5-yl)but-2-enamide To a solution of 2-cyano-N-(2-methyl-3-phenyl-imidazol-4-yl)acetamide (100 mg, 0.4162 mmol) in Ethanol (1.5 mL) was sequentially added sodium acetate (68.28 mg, 0.8324 mmol), 2,2,2-trichloroacetonitrile (0.051 mL, 0.5016 mmol) and the reaction was stirred at room temperature for 4 h. A further 10 mg of sodium acetate and 10 uL 2,2,2-trichloroacetonitrile was sequentially added and the mixture was stirred for a further 2 h at RT. The reaction was concentrated in vacuo and the residue was partitioned between water and EtOAc. Combined organic extract was washed with brine, dried (MgSO₄) and concentrated in vacuo to give 3-amino-4,4,4-trichloro-2-cyano-N-(2-methyl-1-phenyl-1H-imidazol-5-yl) but-2-enamide as a redish oil. (153 mg, 79%). MS (ES+) 384.0.

Step 5: 3,5-diamino-N-(2-methyl-1-phenyl-1H-imidazol-5-yl)-1H-pyrazole-4-carboxamide To a solution of 3-amino-4,4,4-trichloro-2-cyano-N-(2-methyl-3-phenyl-imidazol-4-yl)but-2-enamide (150 mg, 0.39 mmol) in NMP (1.5 mL) was added hydrazine hydrate (0.032 mL, 1.02 mmol) and the mixture heated to 85° C. for 3 h. The reaction was allowed to cool to RT and concentrated in vacuo to give 3,5-diamino-N-(2-methyl-1-phenyl-1H-imidazol-5-yl)-1H-pyrazole-4-carboxamide as an orange oil. (116 mg, 100%). MS (ES+) 298.2.

Step 6: 2-amino-6-fluoro-N-(2-methyl-1-phenyl-1H-imidazol-5-yl)pyrazolo[1,5-a]pyrimidine-3-carboxamide To a mixture of 3,5-diamino-N-(2-methyl-3-phenyl-imidazol-4-yl)-1H-pyrazole-4-carboxamide (116 mg, 0.3902 mmol), 3-(diisopropylamino)-2-fluoro-prop-2-enal (67.59 mg, 0.3902 mmol) in isopropanol (0.58 mL) and water (0.58 mL) was added acetic acid (0.221 mL, 3.904 mmol) and the solution was heated to 88° C. for 2.5 h. The reaction mixture was partitioned between EtOAc and saturated sodium carbonate solution. Combined organic extract was dried (MgSO₄), and concentrated in vacuo to give as a redish oil that was purified by fractionlynx. Clean fractions were freeze-dried to give 2-amino-6-fluoro-N-(2-methyl-1-phenyl-1H-imidazol-5-yl)pyrazolo[1,5-a]pyrimidine-3-carboxamide as a yellow solid. (16.4 mg, 8.5%). MS (ES+) 352.2.

Preparation 11: 2-amino-N-(4-bromo-3-methyl-isothiazol-5-yl)-6-fluoropyrazolo[1,5-a]pyrimidine-3-carboxamide

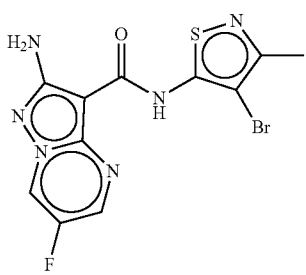

NaH (210.3 mg, 5.259 mmol) was added to a solution of 4-bromo-3-methyl-isothiazol-5-amine (533 mg, 2.761 mmol) in dry NMP (21.95 mL) at RT. The solution was stirred at RT for 5 min before (6-chlorobenzotriazol-1-yl) 2-amino-6-fluoro-pyrazolo[1,5-a]pyrimidine-3-carboxylate 6a* (914.4 mg, 2.630 mmol) was added. After 10 min, the reaction mixture was treated with water (120 mL) and stirred for 15 mins. The pale brown solid was filtered off and dried in vacuo to afford 4-bromo-3-methylisothiazol-5-yl 2-amino-6-fluoropyrazolo[1,5-a]pyrimidine-3-carboxylate. (801 mg, 82%). MS (ES+) 370.5.

Preparation 12:
3-methyl-4-(pyridin-3-yl)isothiazol-5-amine

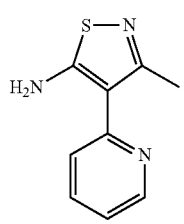

3-pyridylboronic acid (127.3 mg, 1.036 mmol), 4-bromo-3-methyl-isothiazol-5-amine (100 mg, 0.518 mmol), Na₂CO₃ (777 μL of 2 M, 1.554 mmol), palladium triphenylphosphane (29.93 mg, 0.0259 mmol) in dioxane (6 mL) was heated at 110° C. in a microwave for 30 min. The mixture was concentrated in vacuo and the residue was loaded on a SCX column, washed with DCM/MeOH mixtures before the product was eluted with a 2M solution of ammonia in MeOH. The eluent was concentrated in vacuo to yield 3-methyl-4-(pyridin-3-yl)isothiazol-5-amine as a pale yellow oil that was used in next step without further purification. MS (ES+) 192.0.

The following 3-aminoisothiazole intermediates were prepared using preparation 12:

3-methyl-4-(2-methylpyridin-3-yl)isothiazol-5-amine:

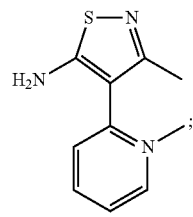

4-cyclopropyl-3-methylisothiazol-5-amine:

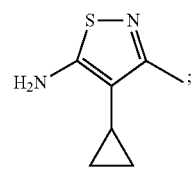

3-methyl-4-(1-methyl-1,2,3,6-tetrahydropyridin-4-yl)isothiazol-5-amine:

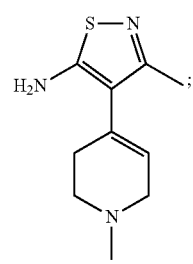

4-(3,6-dihydro-2H-pyran-4-yl)-3-methylisothiazol-5-amine:

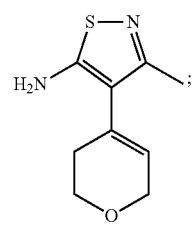

and
3-methyl-4-phenylisothiazol-5-amine:

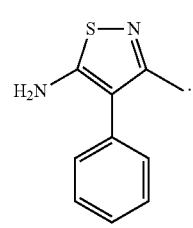

Preparation 13: 3-methyl-4-(pyrrolidin-1-yl) isothiazol-5-amine

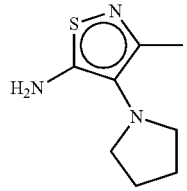

Step 1: methyl 2-((3-methyl-4-nitroisothiazol-5-yl) carbamoyl)benzoate

A mixture of 5-bromo-3-methyl-4-nitro-isothiazole (200 mg, 0.8967 mmol), (1,3-dioxoisoindolin-2-yl)potassium (174.4 mg, 0.9415 mmol) in dry DMF (2 mL) was stirred at RT overnight. The mixture was quenched by the addition of methanol, stirred at RT for 1 h, then the reaction mixture was concentrated in vacuo. The residue was triturated in a small volume of dry MeOH. The precipitate was collected by filtration and dried in vacuo, yielding methyl 2-((3-methyl-4-nitroisothiazol-5-yl)carbamoyl)benzoate as a pale yellow solid. (165 mg, 57%) MS (ES+) 322.1.

Step 2: methyl 2-((4-amino-3-methylisothiazol-5-yl) carbamoyl)benzoate

Methyl 2-((3-methyl-4-nitroisothiazol-5-yl)carbamoyl) benzoate was suspended in MeOH (30 mL), Pd/C 10% (477.1 mg, 4.483 mmol) was added and the mixture was hydrogenated at RT under 1 atm of hydrogen (balloon pressure) for 2 h. The catalyst was filtered off and the mixture was concentrated in vacuo, yielding methyl 2-((4-amino-3-methyl-isothiazol-5-yl)carbamoyl)benzoate. (150 mg, 100%). MS (ES+) 292.1.

Step 3: 2-(3-methyl-4-(pyrrolidin-1-yl)isothiazol-5-yl)isoindoline-1,3-dione DIEA (332.7 mg, 448.4 µL, 2.574 mmol), 1,4-dibromobutane (555.8 mg, 307.4 µL, 2.574 mmol) was added to a solution of methyl 2-[(4-amino-3-methyl-isothiazol-5-yl)carbamoyl]benzoate (150 mg, 0.5149 mmol) in DMF (4 mL) and the mixture was stirred at 130° C. for 40 min in a microwave. The reaction mixture was concentrated in vacuo to yield 2-(3-methyl-4-(pyrrolidin-1-yl)isothiazol-5-yl)isoindoline-1,3-dione that was used in next step without further purification. MS (ES+) 314.1.

Step 4: 3-methyl-4-(pyrrolidin-1-yl)isothiazol-5-amine

Hydrazine hydrate (25.56 mg, 25.03 µL, 0.5106 mmol) was added to a solution of 2-(3-methyl-4-pyrrolidin-1-yl-isothiazol-5-yl)isoindoline-1,3-dione (160 mg, 0.5106 mmol) in EtOH (5 mL) and the mixture was stirred at RT for 10 min. The mixture was heated for 15 min at 120° C. in a microwave, then was concentrated in vacuo. The residue was purified by fractionlynx. The clean fractions were concentrated in vacuo and dried by azeotropic distillation with toluene (×2) to yield 3-methyl-4-(pyrrolidin-1-yl)isothiazol-5-amine as pale yellow solid. (61.7 mg, 59.9% over two steps). MS (ES+) 184.1.

Example 6

2-amino-6-fluoro-N-(3-methyl-4-(1-methyl-1H-imidazol-5-yl)isothiazol-5-yl)pyrazolo[1,5-a]pyrimidine-3-carboxamide (compound I-E-6)

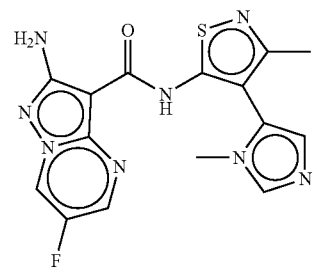

2-amino-N-(4-bromo-3-methyl-isothiazol-5-yl)-6-fluoro-pyrazolo[1,5-a]pyrimidine-3-carboxamide (20 mg, 0.05388 mmol), tributyl-(3-methylimidazol-4-yl)stannane (40.01 mg, 0.1078 mmol) dichloropalladium triphenylphosphane (7.566 mg, 0.01078 mmol) in DMF (2 mL) was degassed for 5 min, then heated at 110° C. After 2 h, the reaction mixture was loaded on a SCX column, washed with DCM/MeOH mixtures. The product was eluted with a 2M solution of ammonia in MeOH and the eluent was concentrated in vacuo. The residue was purified by fractionlynx to yield 2-amino-6-fluoro-N-(3-methyl-4-(1-methyl-1H-imidazol-5-yl)isothiazol-5-yl)pyrazolo[1,5-a]pyrimidine-3-carboxamide as a pale yellow solid. (8.09 mg, 37.4%). MS (ES+) 373.1.

Example 7

2-amino-6-fluoro-N-(3-methyl-4-(morpholinomethyl)isothiazol-5-yl)pyrazolo[1,5-a]pyrimidine-3-carboxamide (compound I-E-15)

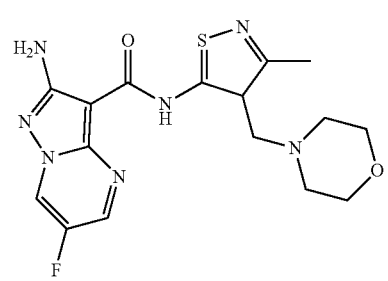

2-amino-N-(4-bromo-3-methyl-isothiazol-5-yl)-6-fluoro-pyrazolo[1,5-a]pyrimidine-3-carboxamide (50 mg, 0.1078 mmol), trifluoro(morpholinomethyl)boranuide (Potassium Ion (1)) (29.01 mg, 0.1401 mmol), dicesium carbonate (105.4 mg, 0.3234 mmol), palladium(+2) cation diacetate (4.84 mg, 0.02156 mmol), dicyclohexyl-[2-(2,4,6-triisopropylphenyl) phenyl]phosphane (20.56 mg, 0.04312 mmol) in dioxane (4 mL)-water (0.5 mL) was heated at 90° C. for 5 h. The reaction mixture was concentrated in vacuo and the residue was purified by fractionlynx. The clean fractions were freeze dried, yielding 2-amino-6-fluoro-N-(3-methyl-4-(morpholinomethyl)isothiazol-5-yl)pyrazolo[1,5-a]pyrimidine-3-carboxamide as a pale yellow solid. (21 mg, 32%). MS (ES+) 392.2.

Example 8

2-amino-6-fluoro-N-(3-methyl-4-(pyrrolidin-1-yl)isothiazol-5-yl)pyrazolo[1,5-a]pyrimidine-3-carboxamide (compound I-E-21)

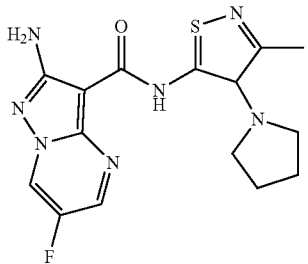

A mixture of (6-chlorobenzotriazol-1-yl) 2-amino-6-fluoro-pyrazolo[1,5-a]pyrimidine-3-carboxylate (140.4 mg, 0.4038 mmol), 3-methyl-4-(pyrrolidin-1-yl)isothiazol-5-amine (37 mg, 0.2019 mmol) (synthesized according to preparation 13) in pyridine (3 mL) was heated at 105° C. for 24 h. The mixture was concentrated in vacuo and the residue was purified by fractionlynx. The clean fractions were combined and freeze dried to yield 2-amino-6-fluoro-N-(3-methyl-4-(pyrrolidin-1-yl)isothiazol-5-yl)pyrazolo[1,5-a]pyrimidine-3-carboxamide as a pale yellow solid. (25 mg, 26%). MS (ES+) 362.1.

The following compounds were successfully prepared using a procedure similar to Example 6 or Example 7:
N-(4-(1-acetyl-1,2,3,6-tetrahydropyridin-4-yl)-3-methylisothiazol-5-yl)-2-amino-6-fluoropyrazolo[1,5-a]pyrimidine-3-carboxamide (compound I-E-9);
2-amino-6-fluoro-N-(3-methyl-4-(pyrimidin-5-yl)isothiazol-5-yl)pyrazolo[1,5-a]pyrimidine-3-carboxamide (compound I-E-11);
2-amino-6-fluoro-N-(3-methyl-4-(1-methyl-1H-pyrazol-4-yl)isothiazol-5-yl)pyrazolo[1,5-a]pyrimidine-3-carboxamide (compound I-E-12);
2-amino-6-fluoro-N-(3-methyl-4-(2-methylpyridin-4-yl)isothiazol-5-yl)pyrazolo[1,5-a]pyrimidine-3-carboxamide (compound I-E-13);
2-amino-6-fluoro-N-(3-methyl-4-(pyridin-4-yl)isothiazol-5-yl)pyrazolo[1,5-a]pyrimidine-3-carboxamide (compound I-E-14);
2-amino-6-fluoro-N-(3-methyl-4-(morpholinomethyl)isothiazol-5-yl)pyrazolo[1,5-a]pyrimidine-3-carboxamide (compound I-E-15);
2-amino-N-(4-(1,3-dimethyl-1H-pyrazol-5-yl)-3-methylisothiazol-5-yl)-6-fluoropyrazolo[1,5-a]pyrimidine-3-carboxamide (compound I-E-16);
2-amino-6-fluoro-N-(3-methyl-4-(pyrrolidin-1-ylmethyl)isothiazol-5-yl)pyrazolo[1,5-a]pyrimidine-3-carboxamide (compound I-E-17);
2-amino-N-(4-(1,3-dimethyl-1H-pyrazol-4-yl)-3-methylisothiazol-5-yl)-6-fluoropyrazolo[1,5-a]pyrimidine-3-carboxamide (compound I-E-18);
2-amino-6-fluoro-N-(3-methyl-4-((4-methylpiperazin-1-yl)methyl)isothiazol-5-yl)pyrazolo[1,5-a]pyrimidine-3-carboxamide (compound I-E-19); and
2-amino-6-fluoro-N-(4-(methoxymethyl)-3-methylisothiazol-5-yl)pyrazolo[1,5-a]pyrimidine-3-carboxamide (compound I-E-20).

The following compounds were successfully prepared using a procedure similar to Example 8:
2-amino-6-fluoro-N-(3-methyl-4-(2-methylpyridin-3-yl)isothiazol-5-yl)pyrazolo[1,5-a]pyrimidine-3-carboxamide (compound I-E-1);
2-amino-N-(4-cyclopropyl-3-methylisothiazol-5-yl)-6-fluoropyrazolo[1,5-a]pyrimidine-3-carboxamide (compound I-E-2);
2-amino-6-fluoro-N-(3-methyl-4-(pyridin-3-yl)isothiazol-5-yl)pyrazolo[1,5-a]pyrimidine-3-carboxamide (compound I-E-3);
2-amino-N-(4-(3,6-dihydro-2H-pyran-4-yl)-3-methylisothiazol-5-yl)-6-fluoropyrazolo[1,5-a]pyrimidine-3-carboxamide (compound I-E-4);
2-amino-6-fluoro-N-(3-methyl-4-(1-methyl-1,2,3,6-tetrahydropyridin-4-yl)isothiazol-5-yl)pyrazolo[1,5-a]pyrimidine-3-carboxamide (compound I-E-5);
2-amino-6-fluoro-N-(3-methyl-4-phenylisothiazol-5-yl)pyrazolo[1,5-a]pyrimidine-3-carboxamide (compound I-E-7); and
2-amino-6-fluoro-N-(3-methyl-4-(pyrrolidin-1-yl)isothiazol-5-yl)pyrazolo[1,5-a]pyrimidine-3-carboxamide (compound I-E-21).

Example 9

2-amino-6-fluoro-N-(3-methyl-4-(1H-pyrazol-1-yl)isothiazol-5-yl)pyrazolo[1,5-a]pyrimidine-3-carboxamide (compound I-E-10)

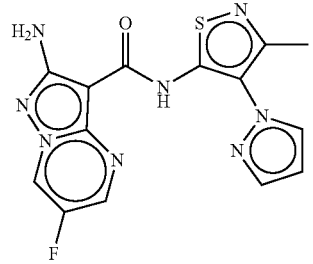

A mixture of 2-amino-N-(4-bromo-3-methyl-isothiazol-5-yl)-6-fluoro-pyrazolo[1,5-a]pyrimidine-3-carboxamide (20 mg, 0.05388 mmol), 1H-pyrazole (7.339 mg, 0.1078 mmol), CuI (21 mg, 0.1103 mmol), $Cs_2CO_3$ (71 mg, 0.2179 mmol) in DMF (2 mL) was degassed with nitrogen and heated at 140° C. in a microwave for 1 h. The insoluble material was filtered off and the filtrate was purified by fractionlynx. The clean fractions were freeze-dried yielding 2-amino-6-fluoro-N-(3-methyl-4-(1H-pyrazol-1-yl)isothiazol-5-yl)pyrazolo[1,5-a]pyrimidine-3-carboxamide as a pale yellow solid. (0.63 mg, 1.9%). MS (ES+) 359.1.

Compound Analytical Data

| Cmpds of Formula I and I-A | LCMS ES+ | LCMS (Rt min) | HNMR |
|---|---|---|---|
| I-A-1 | 387.3 | 2.18 | $^1$H NMR (500 MHz, DMSO-d6) δ 1.67 (2H, m), 2.01 (2H, m), 2.26 (3H, m), 2.52 (br s, 3H), 2.92 (1H, m), 5.26 (1H, m), 6.74 (2H, br s), 8.49 (1H, s), 8.74 (1H, m), 9.50 (2H, m) and 9.99 (1H, br s). |
| I-A-2 | 387.3 | 2.17 | $^1$H NMR (500 MHz, DMSO-d6) δ 1.61-.171 (2H, m), 1.93 (1H, m), 2.02 (1H, m), 2.29 (1H, m), 2.40 (1H, m), 2.47 (1H, m), 2.85 (1H, m), 5.21-5.25 (1H, m), 6.74 (2H, br s), 8.48 (1H, m), 8.73 (1H, d), 9.50 (2H, m) and 10.01 (1H, s) ppm. |
| I-A-3 | 399.0 | 2.01 | $^1$H NMR (500 MHz, DMSO-d6) δ 9.92 (s, 1H), 9.81 (s, 1jH), 9.55 (s, 1H), 9.52 (dd, J = 4.8, 2.5 Hz, 1H), 8.74 (dd, J = 2.5, 0.5 Hz, 1H), 8.50 (s, 1H), 6.78 (s, 2H), 5.50-5.42 (m, 1H), 3.90 (m, 1H), 3.53-3.25 (m, 5H), 2.59 (s, 1H), 2.47-2.37 (m, 1H), 2.08-1.93 (m, 3H). |
| I-A-4 | 399.0 | 2.02 | $^1$H NMR (500 MHz, DMSO-d6) δ 9.87 (s, 1H), 9.82 (s, 1H), 9.55 (s, 1H), 9.52 (dd, J = 4.8, 2.5 Hz, 1H), 8.79-8.72 (m, 1H), 8.51 (s, 1H), 6.78 (s, 2H), 5.45 (d, J = 9.1 Hz, 1H), 3.90 (m, 1H), 3.50-3.26 (m, 5H), 2.43 (d, J = 11.4 Hz, 1H), 2.07-1.94 (m, 3H). |
| I-A-5 | 387.0 | 2.00 | $^1$H NMR (500 MHz, DMSO-d6 @ 375K) δ 2.25-2.34 (5H, m), 3.44 (3H, m), 5.47 (1H, m), 8.50 (1H, s), 8.73 (1H, m), 9.34 (1H, m), 9.49 (1H, s) and 9.78 (1H, br s) ppm. |
| I-A-6 | 403.1 | 2.08 | $^1$H NMR (500 MHz, DMSO-d6) δ 9.90 (s, 1H), 9.50 (s, 1H), 9.45 (d, J = 2.2 Hz, 1H), 8.60 (d, J = 2.2 Hz, 1H), 8.48 (s, 1H), 6.80 (s, 2H), 5.21 (s, 1H), 2.74 (br s, 2H), 2.32 (br s, 2H), 2.24 (s, 3H), 2.08 (br s, 2H), 1.91 (br s, 2H). |
| I-A-7 | 437.2 | 2.30 | $^1$H NMR (500 MHz, DMSO-d6) δ 9.49 (s, 1H), 9.35 (s, 1H), 9.29 (d, J = 6.9 Hz, 1H), 8.52 (s, 1H), 7.53 (d, J = 6.9 Hz, 1H), 7.04 (s, 2H), 5.24 (br s, 1H), 2.79 (br s, 2H), 2.21 (s, 3H), 2.14-1.98 (m, 4H), 1.91-1.70 (m, 2H). |
| I-A-8 | 429.2 | 1.90 | $^1$H NMR (500 MHz, DMSO-d6 @ 360K) δ 2.21-2.38 (4H, m), 3.22-3.30 (4H, m), 4.35 (1H, m), 4.79 (4H, m), 5.45 (1H, m), 8.50 (1H, s), 8.72 (1H, m), 9.38 (1H, m), 9.49 (1H, s) and 9.81 (1H, br s) ppm. |
| I-A-9 | 445.1 | 1.99 | $^1$H NMR (500 MHz, DMSO-d6) δ 9.88 (s, 1H), 9.50 (s, 1H), 9.45 (d, J = 2.2 Hz, 1H), 8.60 (d, J = 2.2 Hz, 1H), 8.49 (s, 1H), 6.80 (s, 2H), 5.25 (dp, J = 11.8, 4.0 Hz, 1H), 4.56 (t, J = 6.5 Hz, 2H), 4.47 (t, J = 6.1 Hz, 2H), 3.45 (p, J = 6.4 Hz, 1H), 2.68-2.61 (m, 2H), 2.25 (t, J = 9.5 Hz, 2H), 2.15-2.06 (m, 2H), 1.90 (dtd, J = 11.7, 8.1, 3.3 Hz, 2H). |
| I-A-10 | 373.0 | 1.97 | $^1$H NMR (500 MHz, DMSO-d6) δ 10.25 (s, 1H), 9.91 (d, J = 44.6 Hz, 1H), 9.52 (s, 2H), 8.90 (d, J = 2.4 Hz, 1H), 8.53 (s, 1H), 6.76 (s, 2H), 5.72 (d, J = 4.4 Hz, 1H), 4.18-3.76 (m, 3H), 3.46-3.18 (m, 2H), 2.94 (dd, J = 26.9, 3.9 Hz, 3H). |
| I-A-11 | 373.0 | 1.97 | $^1$H NMR (500 MHz, DMSO-d6) δ 10.35 (s, 1H), 9.91 (d, J = 44.9 Hz, 1H), 9.52 (d, J = 2.5 Hz, 2H), 8.89 (d, J = 2.5 Hz, 1H), 8.53 (s, 1H), 6.75 (s, 1H), 5.71 (d, J = 6.2 Hz, 1H), 3.92 (s, 4H), 3.62-3.18 (m, 2H), 3.01-2.84 (m, 3H). |
| I-A-12 | 415.0 | 2.16 | $^1$H NMR (500 MHz, DMSO-d6) δ 10.08 (s, 1H), 9.74 (s, 1H), 9.52 (dd, J = 4.8, 2.5 Hz, 1H), 9.48 (s, 1H), 8.84 (d, J = 2.5 Hz, 1H), 8.49 (s, 1H), 6.74 (s, 2H), 5.15 (m, 1H), 3.42-3.32 (m, 1H), 2.80 (d, J = 4.9 Hz, 6H), 2.35 (d, J = 8.9 Hz, 2H), 2.12 (s, 2H), 1.80-1.58 (m, 4H). |
| I-A-13 | 465.0 | 2.44 | $^1$H NMR (500 MHz, DMSO-d6) δ 9.48 (s, 1H), 9.35 (s, 1H), 9.31-9.24 (m, 1H), 8.50 (s, 1H), 7.52 (d, J = 6.9 Hz, 1H), 7.03 (s, 2H), 5.24 (td, J = 10.9, 5.4 Hz, 1H), 2.20 (s, 6H), 2.18 (s, 1H), 2.15 (m, 2H), 1.93-1.85 (m, 2H), 1.54 (td, J = 12.7, 12.0, 3.3 Hz, 2H), 1.38 (qd, J = 13.3, 3.2 Hz, 2H). |
| I-A-14 | 332.1 | 2.39 | $^1$H NMR (500 MHz, DMSO-d6) δ 1.47-1.49 (6H, d), 5.41-5.43 (1H, m), 8.50 (1H, s), 8.82-8.83 (1H, d), 9.47 (1H, s), 9.50-9.51 (1H, dd), 10.06 (1H, s). |
| I-A-15 | 401.2 | 2.23 | $^1$H NMR (500 MHz, DMSO-d6) δ 1.4 (6H, d), 2.88-2.92 (6H, m), 3.6-3.63 (2H, m), 4.8-4.82 (2H, m), 6.5 (2H, brs), 6.6 (1H, d), 8.55 (1H, s), 8.82 (1H, d), 9.06 (1H, s), 9.22 (1H, s), 9.62 (1H, brs). |

-continued

| Cmpds of Formula I and I-A | LCMS ES+ | LCMS (Rt min) | HNMR |
|---|---|---|---|
| I-A-16 | 373.2 | 1.92 | $^1$H NMR (500 MHz, DMSO-d6) δ 2.82-2.87 (6H, m), 3.6-3.63 (2H, m), 4.12 (3H, s), 4.8-4.83 (2H, m), 6.5 (2H, brs), 6.6 (1H, d), 8.55 (1H, s), 8.82 (1H, d), 9.52 (1H, s), 9.62 (1H, brs) |
| I-A-17 | 325.1 | 1.79 | — |
| I-A-18 | 385.0 | 1.83 | $^1$H NMR (500 MHz, DMSO-d6) δ 10.05 (s, 1H), 9.55 (dd, J = 4.8, 2.5 Hz, 1H), 9.48 (s, 1H), 9.07 (s, 2H), 8.80 (d, J = 2.5 Hz, 1H), 8.49 (s, 1H), 6.76 (s, 2H), 5.21 (p, J = 6.8 Hz, 1H), 3.90-3.78 (m, 2H), 3.14-3.06 (m, 2H), 2.90-2.82 (m, 2H), 2.65 (t, J = 8.2 Hz, 2H). |
| I-A-19 | 483.4 | 1.77 | $^1$H NMR (500 MHz, DMSO-d6) δ 9.90 (s, 1H), 9.55-9.49 (m, 2H), 9.13 (s, 1H), 8.85 (d, J = 2.5 Hz, 1H), 8.63 (d, J = 0.6 Hz, 1H), 6.76 (s, 2H), 4.51 (s, 1H), 3.95 (d, J = 12.8 Hz, 2H), 3.10-2.95 (m, 5H), 2.93 (s, 2H), 2.83 (s, 3H), 2.58 (s, 1H), 1.90 (s, 2H), 1.76 (dd, J = 13.2, 3.8 Hz, 2H). |
| I-A-20 | 372.2 | 1.69 | $^1$H NMR (500 MHz, DMSO-d6) 9.82 (s, 1H), 9.53 (dd, J = 4.8, 2.5 Hz, 1H), 9.39 (s, 1H), 9.25 (s, 1H), 9.00 (dd, J = 2.6, 0.6 Hz, 1H), 8.64 (s, 1H), 6.76 (s, 2H), 4.01 (d, J = 9.9 Hz, 2H), 3.37-3.10 (m, 5H), 2.94 (s, 3H). |

| Cmpds of Formula I and I-B | LCMS ES+ | LCMS (Rt min) | HNMR |
|---|---|---|---|
| I-B-1 | 372.1 | 1.63 | $^1$H NMR (500 MHz, DMSO-d6) δ 10.11 (d, J = 0.7 Hz, 1H), 9.92 (s, 1H), 9.52 (dd, J = 4.8, 2.5 Hz, 1H), 9.03 (d, J = 0.8 Hz, 1H), 8.83 (d, J = 2.5 Hz, 1H), 6.83 (s, 2H), 3.08 (t, J = 4.8 Hz, 4H), 2.60 (t, J = 4.8 Hz, 4H), 2.32 (s, 3H). |
| I-B-2 | 414.2 | 1.55 | $^1$H NMR (500 MHz, DMSO-d6) δ 12.38 (s, 1H), 10.16 (s, 1H), 9.95 (s, 1H), 9.58 (dd, J = 4.6, 2.5 Hz, 1H), 9.22 (s, 1H), 9.08 (d, J = 2.7 Hz, 1H), 6.88 (s, 2H), 4.92 (t, J = 6.7 Hz, 2H), 4.75 (t, J = 7.2 Hz, 2H), 4.66 (s, 1H), 3.62-3.55 (m, 4H), 3.18 (s, 4H). |
| I-B-3 | 442.2 | 1.73 | $^1$H NMR (500 MHz, Methanol-d4) δ 10.27 (d, J = 0.7 Hz, 1H), 9.13 (dd, J = 4.3, 2.5 Hz, 1H), 9.04 (d, J = 0.7 Hz, 1H), 8.84 (dd, J = 2.6, 0.6 Hz, 1H), 4.15 (dd, J = 11.6, 4.5 Hz, 2H), 3.58-3.44 (m, 10H), 2.18 (d, J = 11.6 Hz, 2H), 1.81 (tt, J = 13.3, 6.7 Hz, 2H), 1.39-1.27 (m, 1H). |
| I-B-4 | 365.0 | 1.68 | $^1$H NMR (500 MHz, DMSO-d6) δ 10.47 (s, 1H), 9.61 (s, 1H), 9.44 (dd, J = 4.7, 2.5 Hz, 1H), 9.11 (s, 1H), 8.83 (dd, J = 5.0, 1.8 Hz, 1H), 7.98 (d, J = 2.6 Hz, 1H), 7.59 (s, 1H), 6.60 (bs, 3H), 2.32 (s, 3H). |
| I-B-5 | 483.2 | 1.78 | $^1$H NMR (500 MHz, DMSO-d6) δ 1.75 (2H, m), 2.09-2.14 (2H, m), 2.21 (3H, s), 2.29 (2H, m), 2.37 (2H, m), 2.91-2.96 (3H, m), 3.17 (2H, m), 3.57 (4H, m), 6.84 (2H, br s), 9.01 (1H, s), 9.04 (1H, d), 9.52 (1H, dd), 10.24 (1H, s) and 10.27 (1H, br s) ppm. |
| I-B-6 | 476.1 | 2.56 | $^1$H NMR (500 MHz, Methanol-d4) δ 10.14 (s, 1H), 9.14 (dd, J = 4.3, 2.5 Hz, 1H), 9.06 (s, 1H), 8.79 (d, J = 2.4 Hz, 1H), 3.87-3.72 (m, 4H), 3.69-3.48 (m, 2H), 3.26-2.98 (m, 4H), 2.63 (ddd, J = 21.3, 14.6, 7.9 Hz, 2H), 2.11 (ddt, J = 18.4, 7.4, 3.7 Hz, 1H), 2.04 (d, J = 12.7 Hz, 2H), 1.70 (qd, J = 12.7, 12.2, 3.8 Hz, 2H). |
| I-B-7 | 462.1 | 2.03 | $^1$H NMR (500 MHz, DMSO-d6) δ 10.42 (d, J = 0.9 Hz, 1H), 10.07 (s, 1H), 9.47 (dd, J = 4.8, 2.5 Hz, 1H), 9.06 (d, J = 0.9 Hz, 1H), 8.17 (d, J = 2.5 Hz, 1H), 7.65 (s, 4H), 6.82 (s, 2H), 3.85 (br s, 2H), 3.43 (br s, 2H), 3.06 (br s, 4H), 2.81 (s, 3H), 2.47 (br s, 4H). |
| I-B-8 | 456.2 | 2.06 | $^1$H NMR (500 MHz, DMSO-d6) δ 10.14 (s, 1H), 9.91 (s, 1H), 9.56 (dd, J = 4.8, 2.5 Hz, 1H), 9.32 (s, 1H), 9.06 (d, J = 2.5 Hz, 1H), 8.91 (s, 1H), 6.87 (s, 2H), 4.01 (d, J = 12.9 Hz, 2H), 3.73 (t, J = 12.3 Hz, 2H), 3.52 (d, J = 12.7 Hz, 2H), 3.38 (d, J = 11.6 Hz, 2H), 3.31-3.22 (m, 2H), 3.18-3.07 (m, 2H), 2.97-2.88 (m, 2H), 2.06 (s, 1H), 1.92 (d, J = 12.3 Hz, 2H), 1.57 (dd, J = 23.7, 11.3 Hz, 2H). |

-continued

| Cmpds of Formula I and I-B | LCMS ES+ | LCMS (Rt min) | HNMR |
|---|---|---|---|
| I-B-9 | 357.0 | 2.28 | $^1$H NMR (500 MHz, DMSO-d6) δ 10.01 (s, 1H), 9.96 (s, 1H), 9.54 (dd, J = 4.7, 2.5 Hz, 1H), 9.09 (s, 1H), 8.91 (d, J = 2.5 Hz, 1H), 6.84 (s, 2H), 3.22 (t, J = 5.4 Hz, 4H), 1.82-1.74 (m, 4H), 1.66 (q, J = 5.9 Hz, 2H). |
| I-B-10 | 525.2 | 2.18 | $^1$H NMR (500 MHz, DMSO-d6) δ 10.29-10.22 (m, 2H), 10.15 (s, 1H), 9.55 (dd, J = 4.8, 2.5 Hz, 1H), 9.07-8.98 (m, 2H), 6.85 (s, 2H), 4.64 (d, J = 13.6 Hz, 1H), 4.28 (d, J = 14.5 Hz, 1H), 3.58 (ddd, J = 37.3, 20.9, 8.3 Hz, 4H), 3.22 (d, J = 11.2 Hz, 1H), 3.10 (dt, J = 24.6, 12.0 Hz, 2H), 2.95 (tdd, J = 11.8, 9.4, 3.4 Hz, 4H), 2.12 (dd, J = 23.3, 12.2 Hz, 2H), 1.83 (t, J = 16.7 Hz, 2H), 1.37 (s, 10H). |
| I-B-11 | 469.1 | 1.94 | $^1$H NMR (500 MHz, DMSO-d6) δ 10.04 (s, 1H), 9.91 (s, 1H), 9.56 (dd, J = 4.7, 2.5 Hz, 1H), 9.10 (s, 1H), 8.87 (d, J = 2.5 Hz, 1H), 6.86 (s, 2H), 4.89 (br s, 4H), 3.53 (br d, 4H), 3.53-3.16 (br m, 2H), 2.97 (t, J = 11.4 Hz, 2H), 2.81 (s, 3H), 2.74 (br s, 2H), 1.89 (d, J = 12.2 Hz, 3H), 1.49 (q, J = 12.6 Hz, 2H). |
| I-B-12 | 359.0 | 1.68 | $^1$H NMR (500 MHz, DMSO-d6) δ 10.10 (s, 1H), 10.00 (s, 1H), 9.54 (dd, J = 4.7, 2.5 Hz, 1H), 9.12 (d, J = 0.6 Hz, 1H), 9.02-8.92 (m, 1H), 6.84 (s, 2H), 3.94-3.80 (m, 4H), 3.28-3.15 (m, 4H). |
| I-B-13 | 476.0 | 1.84 | $^1$H NMR (500 MHz, DMSO-d6) δ 10.42 (d, J = 0.9 Hz, 1H), 9.83 (s, 1H), 9.28 (dd, J = 4.7, 2.5 Hz, 1H), 9.02 (d, J = 0.9 Hz, 1H), 8.31 (dd, J = 2.5, 0.5 Hz, 1H), 7.76-7.65 (m, 4H), 3.81 (s, 4H), 3.26 (s, 4H), 2.83 (s, 3H). |
| I-B-14 | 497.2 | 1.9 | $^1$H NMR (500 MHz, DMSO-d6) d 1.79 (2H, m), 2.13 (2H, m), 2.77 (3H, s), 2.85 (3H, s), 3.00-3.06 (6H, m), 3.29 (2H, m), 3.49 (2H, m), 4.34 (2H, m), 4.60 (2H, m), 6.92 (2H, br s), 9.27 (1H, s), 9.55 (1H, m), 10.07 (1H, br s), 10.35 (1H, s) and 10.95 (1H, s) ppm. |
| I-B-15 | 354.1 | 1.42 | $^1$H NMR (500 MHz, DMSO-d6) δ 10.44 (d, J = 1.0 Hz, 1H), 9.96 (s, 1H), 9.47 (dd, J = 4.8, 2.5 Hz, 1H), 9.09 (d, J = 1.0 Hz, 1H), 8.34 (d, J = 2.5 Hz, 1H), 8.10 (s, 1H), 7.32 (d, J = 1.1 Hz, 1H), 6.80 (s, 2H), 3.54 (s, 3H) |
| I-B-16 | 343.1 | 1.72 | $^1$H NMR (500 MHz, DMSO-d6) δ 1.84-1.92 (4H, m), 3.62-3.7 (4H, m), 6.75 (2H, s), 8.76 (1H, s), 8.83 (1H, d), 9.08 (1H, s), 9.49-9.53 (2H, m) |
| I-B-17 | 364.1 | 2.36 | $^1$H NMR (500 MHz, DMSO-d6) δ 10.44 (d, 1H), 9.61 (s, 1H), 9.41 (dd, 1H), 9.00 (d, 1H), 7.96 (d, 1H), 7.74-7.19 (m, 4H), 6.77 (s, 2H), 2.10 (s, 3H). |
| I-B-18 | 314.1 | 1.92 | $^1$H NMR (500 MHz, DMSO-d6) δ 10.59 (s, 1H), 10.29 (d, 1H), 9.56 (dd, 1H), 9.08 (s, 1H), 8.97 (dd, 1H), 6.87 (s, 2H), 2.05-2.01 (m, 1H), 1.33-1.29 (m, 2H), 0.97-0.94 (m, 2H). |
| I-B-19 | 399.0 | 1.66 | $^1$H NMR (500 MHz, Methanol-d4) δ 9.06 (dd, J = 4.4, 2.6 Hz, 1H), 8.97 (s, 1H), 8.71-8.66 (m, 2H), 3.98-3.83 (m, 2H), 3.80-3.74 (m, 2H), 3.74-3.66 (m, 4H), 2.12-1.93 (m, 4H). |
| I-B-20 | 375.0 | 2.02 | $^1$H NMR (500 MHz, DMSO-d6) δ 2.00-2.12 (2H, m), 2.10-2.22 (2H, m), 3.15-3.20 (2H, m), 3.22-3.27 (2H, m), 4.97-5.00 (0.5H, m), 5.05-5.10 (0.5H, m), 6.83 (2H, brs), 8.90 (1H, d), 9.15 (1H, s), 9.52-9.55 (1H, m), 10.03 (1H, s), 10.12 (1H, brs) |
| I-B-21 | 476.1 | 2.02 | $^1$H NMR (500 MHz, DMSO-d6) δ 10.28 (s, 1H), 10.24 (d, J = 0.7 Hz, 1H), 9.53 (dd, J = 4.7, 2.5 Hz, 1H), 9.05 (dd, J = 2.5, 0.6 Hz, 1H), 9.04 (d, J = 0.8 Hz, 1H), 6.84 (s, 2H), 4.75 (t, J = 12.4 Hz, 2H), 4.37 (t, J = 12.6 Hz, 2H), 3.29 (d, J = 0.9 Hz, 1H), 3.21-3.15 (m, 2H), 2.89 (td, J = 12.0, 2.4 Hz, 2H), 2.14-2.01 (m, 2H), 1.89-1.82 (m, 2H). |
| I-B-22 | 458.1 | 1.82 | $^1$H NMR (500 MHz, DMSO-d6) δ 10.29 (s, 1H), 10.24 (d, J = 0.9 Hz, 1H), 9.52 (dd, J = 4.7, 2.5 Hz, 1H), 9.10 (d, J = 2.5 Hz, 1H), 9.03 (d, J = 0.8 Hz, 1H), 6.83 (s, 2H), 5.44 (dtt, J = 57.3, 6.2, 3.1 Hz, 1H), 4.64-4.52 (m, 1H), 4.40-4.20 (m, 2H), 4.03-3.91 (m, 1H), 3.30 (d, J = 6.9 Hz, 1H), 3.17 (d, J = 11.2 Hz, 2H), 2.98-2.85 (m, 2H), 2.15-2.00 (m, 2H), 1.80 (t, J = 14.4 Hz, 2H). |
| I-B-23 | 435.0 | 1.66 | $^1$H NMR (500 MHz, DMSO-d6) δ 2.03-2.12 (2H, m), 2.18-2.25 (2H, m), 2.94-3.02 (2H, m), 3.08 (3H, s), |

| Cmpds of Formula I and I-B | LCMS ES+ | LCMS (Rt min) | HNMR |
|---|---|---|---|
| I-B-24 | 455.1 | 1.65 | 3.42-3.49 (3H, m), 6.88 (2H, brs), 8.82 (1H, d), 9.17 (1H, s), 9.54-9.57 (1H, m), 10.18 (1H, s), 10.22 (1H, brs) $^1$H NMR (500 MHz, DMSO-d6) δ 10.04 (s, 1H), 9.86 (s, 1H), 9.56 (dd, J = 4.7, 2.5 Hz, 1H), 9.09 (s, 1H), 8.84 (d, J = 3.1 Hz, 1H), 6.86 (s, 2H), 4.76 (s, 4H), 3.66-2.93 (m, 9H), 2.81 (s, 3H), 2.05 (d, J = 10.3 Hz, 2H), 1.81 (t, J = 12.1 Hz, 2H). |

| Cmpds of Formula I and I-C | LCMS ES+ | LCMS (Rt min) | HNMR |
|---|---|---|---|
| I-C-1 | 413.2 | 1.91 | $^1$H NMR (500 MHz, DMSO-d6) δ 10.41 (s, 1H), 9.49 (dd, J = 4.8, 2.5 Hz, 1H), 8.80 (d, J = 2.5 Hz, 1H), 8.48 (d, 1H), 8.41 (d, J = 5.5 Hz, 1H), 8.27 (d, J = 5.3 Hz, 1H), 6.80 (s, 2H), 4.62 (t, J = 6.5 Hz, 2H), 4.49 (t, J = 6.1 Hz, 2H), 3.66 (p, J = 6.3 Hz, 1H), 2.99 (t, J = 4.7 Hz, 4H), 2.54 (s, 4H). |
| I-C-2 | 371.2 | 2.04 | $^1$H NMR (500 MHz, DMSO-d6) δ 10.48 (s, 1H), 10.03 (s, 1H), 9.58 (dd, J = 4.7, 2.5 Hz, 1H), 9.08 (d, J = 2.5 Hz, 1H), 8.73 (d, J = 6.1 Hz, 1H), 8.66 (s, 1H), 8.51 (d, J = 6.2 Hz, 1H), 6.89 (s, 2H), 3.66 (d, J = 8.0 Hz, 2H), 3.41 (d, J = 15.4 Hz, 2H), 3.35-3.22 (m, 2H), 3.22-3.11 (m, 2H), 3.02 (s, 3H). |
| I-C-3 | 482.2 | 2.20 | $^1$H NMR (500 MHz, DMSO-d6) δ 11.04 (s, 1H), 9.78 (s, 1H), 9.56 (dd, J = 4.7, 2.5 Hz, 1H), 9.13 (dd, J = 2.5, 0.7 Hz, 1H), 8.80 (d, 1H), 8.58 (s, 1H), 8.49 (d, J = 6.2 Hz, 1H), 6.90 (s, 2H), 4.60 & 4.29 (2 × s, 1H), 3.49 (s, 2H), 3.11 (d, J = 6.8 Hz, 2H), 3.06-2.89 (m, 4H), 2.85 (s, 3H), 2.56-2.48 (m, 4H), 2.15 (s, 2H), 1.83 (d, J = 14.3 Hz, 2H). |
| I-C-4 | 353.0 | 2.61 | $^1$H NMR (500 MHz, DMSO-d6) δ 9.81 (s, 1H), 9.26 (dd, J = 6.9, 0.7 Hz, 1H), 8.19 (dd, J = 9.1, 0.7 Hz, 1H), 8.10 (dd, J = 3.1, 0.7 Hz, 1H), 7.53-7.44 (m, 2H), 6.98 (s, 2H), 3.83 (s, 3H). |
| I-C-5 | 364.0 | 1.95 | $^1$H NMR (500 MHz, DMSO-d6) δ 9.45 (s, 1H), 9.40 (dd, J = 4.8, 2.5 Hz, 1H), 8.76 (dd, J = 4.9, 1.8 Hz, 1H), 8.59-8.51 (m, 2H), 8.36 (d, J = 0.6 Hz, 1H), 7.93 (d, J = 2.5 Hz, 1H), 7.74 (dd, J = 7.6, 1.8 Hz, 1H), 7.48 (ddd, J = 7.7, 4.9, 0.7 Hz, 1H), 6.72 (s, 2H), 2.27 (s, 3H). |
| I-C-6 | 364.0 | 2.01 | $^1$H NMR (500 MHz, DMSO-d6) δ 9.40 (dd, J = 4.8, 2.5 Hz, 1H), 9.36 (s, 1H), 8.76-8.73 (m, 1H), 8.64 (dd, J = 4.7, 0.8 Hz, 1H), 8.56 (s, 2H), 8.36 (s, 1H), 7.88 (d, J = 2.5 Hz, 1H), 7.36 (d, J = 4.9 Hz, 1H), 6.72 (s, 2H), 2.09 (s, 3H). |
| I-C-7 | 508.1 | 2.17 | $^1$H NMR (500 MHz, DMSO-d6) δ 11.15 (s, 0.4H), 11.09 (s, 0.6H), 10.22 (s, 1H), 9.57 (dd, J = 4.7, 2.5 Hz, 1H), 9.32 (d, J = 2.5 Hz, 0.4H), 9.18-9.01 (m, 0.6H), 8.85 (s, 1H), 8.61 (s, 1H), 8.53 (d, J = 6.3 Hz, 1H), 6.90 (s, 2H), 4.75 (s, 0.6H), 4.56 (s, 0.4H), 3.98 (dt, J = 11.0, 5.5 Hz, 2H), 3.54-3.35 (m, 6H), 3.24-3.07 (m, 2H), 2.94 (q, J = 12.1, 11.7 Hz, 3H), 2.32-1.97 (m, 6H), 1.84 (d, J = 12.4 Hz, 2H). |
| I-C-8 | 536.2 | 2.28 | $^1$H NMR (500 MHz, DMSO-d6) δ 11.10 (s, 1H), 9.60 (s, 1H), 9.57 (dd, J = 4.7, 2.5 Hz, 1H), 9.19 (d, J = 2.5 Hz, 1H), 8.85 (d, J = 5.1 Hz, 1H), 8.60 (s, 1H), 8.52 (d, J = 6.4 Hz, 1H), 6.90 (s, 2H), 4.62 (d, J = 13.3 Hz, 1H), 4.21 (d, J = 13.6 Hz, 1H), 3.54 (s, 2H), 3.41 (s, 2H), 3.12 (t, J = 11.3 Hz, 6H), 3.05-2.86 (m, 3H), 2.16 (dd, J = 25.6, 11.5 Hz, 3H), 2.03 (t, J = 7.4 Hz, 2H), 1.96-1.83 (m, 2H), 1.79 (d, J = 13.0 Hz, 2H), 1.61-1.38 (m, 2H). |
| I-C-9 | 524.2 | 2.04 | $^1$H NMR (500 MHz, DMSO-d6) δ 11.16 (s, 1H), 9.57 (dd, J = 4.7, 2.5 Hz, 1H), 9.17 (d, J = 2.4 Hz, 1H), 8.92 (d, J = 6.6 Hz, 1H), 8.65 (s, 1H), 8.57 (d, J = 6.5 Hz, 1H), 6.92 (s, 2H), 4.69 (d, J = 6.8 Hz, 4H), 4.06 (br s, 2H), 3.80 (br s, 4H), 3.12 (dd, J = 11.2, 4.0 Hz, 2H), 3.01-2.80 (m, 6H), 2.15 (qd, J = 12.8, 3.9 Hz, 2H), 1.82 (d, J = 11.3 Hz, 2H). |

| Cmpds of Formula I and I-C | LCMS ES+ | LCMS (Rt min) | HNMR |
|---|---|---|---|
| I-C-10 | 434.0 | 2.0 | $^1$H NMR (500 MHz, DMSO-d6) δ 10.95 (s, 1H), 9.58-9.55 (m, 1H), 8.96-8.94 (m, 1H), 8.88 (d, 1H), 8.68 (s, 1H), 8.53 (d, 1H), 6.84 (2H, brs), 3.44-3.38 (m, 1H), 3.28-3.24 (m, 1H), 3.12 (s, 3H), 2.97-2.90 (m, 2H), 2.28-2.20 (m, 2H), 2.15-2.07 (m, 2H) |
| I-C-11 | 342.1 | 2.37 | $^1$H NMR (500 MHz, DMSO-d6) δ 2.03-2.12 (4H, m), 3.02-3.10 (4H, m), 6.90 (2H, s), 8.47 (1H, d), 8.57 (1H, s), 8.83 (1H, d), 8.87 (1H, d), 9.55-9.58 (2H, m), m 10.68 (1H, s) |

| Cmpds of Formula I and I-D | LCMS ES+ | LCMS (Rt min) | HNMR |
|---|---|---|---|
| I-D-1 | 373.1 | 1.91 | $^1$H NMR (500 MHz, DMSO-d6) δ 9.60 (s, 1H), 9.07 (d, J = 2.0 Hz, 1H), 9.01 (br s, 1H), 8.57 (d, J = 2.0 Hz, 1H), 7.68 (s, 1H), 7.42-7.33 (m, 5H), 6.67 (s, 2H), 5.48 (s, 2H), 4.14 (s, 2H). |
| I-D-2 | 338.0 | 2.04 | $^1$H NMR (500 MHz, DMSO-d6) δ 9.50 (s, 1H), 9.41 (dd, J = 4.9, 2.5 Hz, 1H), 8.48 (d, J = 2.5 Hz, 1H), 7.78 (d, J = 1.2 Hz, 1H), 7.66-7.59 (m, 2H), 7.58-7.52 (m, 3H), 7.19 (dd, J = 1.1, 0.6 Hz, 1H), 6.62 (s, 2H). |
| I-D-3 | 302.1 | 1.69 | $^1$H NMR (500 MHz, DMSO-d6) δ 9.92 (s, 1H), 9.48 (dd, 1H), 8.89 (dd, 1H), 7.45 (d, 1H), 7.03 (d, 1H), 6.67 (s, 2H), 3.28-3.24 (m, 1H), 1.20-1.16 (m, 2H), 1.03-1.00 (m, 2H). |
| I-D-4 | 346.1 | 1.51 | $^1$H NMR (500 MHz, DMSO-d6) δ 9.48 (dd, 1H), 9.29 (s, 1H), 8.83 (dd, 1H), 7.75 (s, 1H), 6.94 (s, 1H), 6.64 (s, 2H), 4.16-4.09 (m, 1H), 4.00-3.96 (m, 2H), 3.47-3.42 (m, 2H), 1.99-1.92 (m, 4H). |
| I-D-5 | 339.1 | 1.45 | $^1$H NMR (500 MHz, DMSO-d6) δ 9.43 (dd, 1H), 9.39 (s, 1H), 8.78 (dd, 1H), 8.69 (dd, 1H), 8.56 (d, 1H), 8.05 (ddd, 1H), 7.92 (d, 1H), 7.64 (ddd, 1H), 7.17 (t, 1H), 6.59 (s, 2H). |
| I-D-6 | 352.0 | 2.08 | $^1$H NMR (500 MHz, DMSO-d6) d 9.57 (1H, s), 9.43 (1H, dd), 8.25 (1H, s), 7.79-7.78 (3H, m), 7.73-7.71 (3H, m), 6.65 (2H, brs), 2.37 (3H, s). |

Compound Analytical Data

| Cmpds of Formula I and I-E | LCMS ES+ | LCMS (Rt min) | HNMR |
|---|---|---|---|
| I-E-1 | 384.0 | 2.17 | $^1$H NMR (500 MHz, DMSO-d6) δ 10.30 (s, 1H), 9.47 (dd, J = 4.7, 2.5 Hz, 1H), 8.81 (dd, J = 5.2, 1.7 Hz, 1H), 8.28 (d, J = 2.5 Hz, 1H), 8.08 (d, J = 7.7 Hz, 1H), 7.72 (dd, J = 7.5, 5.2 Hz, 1H), 6.74 (s, 2H), 2.39 (s, 3H), 2.21 (s, 3H). |
| I-E-2 | 333.0 | 2.51 | $^1$H NMR (500 MHz, DMSO-d6) δ 10.89 (s, 1H), 9.53 (dd, J = 4.8, 2.5 Hz, 1H), 8.98 (d, J = 2.5 Hz, 1H), 2.39 (s, 3H), 1.70 (tt, J = 8.2, 5.4 Hz, 1H), 1.24-1.10 (m, 2H), 0.69-0.54 (m, 2H). |
| I-E-3 | 370.0 | 2.13 | $^1$H NMR (500 MHz, DMSO-d6) δ 10.75 (s, 1H), 9.49 (dd, J = 4.7, 2.5 Hz, 1H), 8.82 (dd, J = 2.3, 0.9 Hz, 1H), 8.80 (dd, J = 5.0, 1.6 Hz, 1H), 8.42 (d, J = 2.5 Hz, 1H), 8.16 (dt, J = 7.8, 1.9 Hz, 1H), 7.83 (ddd, J = 7.9, 5.0, 0.9 Hz, 1H), 2.34 (s, 3H). |
| I-E-4 | 375.0 | 2.28 | $^1$H NMR (500 MHz, DMSO-d6) δ 10.67 (s, 1H), 9.51 (dd, J = 4.7, 2.5 Hz, 1H), 8.84 (d, J = 2.5 Hz, 1H), 6.03-5.93 (m, 1H), 4.38 (q, J = 2.7 Hz, 2H), 3.94 (t, J = 5.3 Hz, 2H), 2.30 (s, 5H). |
| I-E-5 | 388.0 | 2.24 | $^1$H NMR (500 MHz, DMSO-d6) δ 10.55 (s, 1H), 10.19 (s, 1H), 9.48 (dd, J = 4.7, 2.5 Hz, 1H), 8.98 (dd, J = 2.5, 0.6 Hz, 1H), 6.82-6.44 (m, 2H), 6.02-5.87 (m, 1H), 4.24-3.29 (m, 6H), 3.06 (s, 3H), 2.33 (s, 3H). |

-continued

| Cmpds of Formula I and I-E | LCMS ES+ | LCMS (Rt min) | HNMR |
|---|---|---|---|
| I-E-6 | 373.0 | 1.81 | $^1$H NMR (500 MHz, DMSO-d6) δ 10.50 (s, 1H), 9.50 (dd, J = 4.7, 2.5 Hz, 1H), 8.50 (d, J = 2.5 Hz, 1H), 8.29 (s, 1H), 7.31 (d, J = 1.2 Hz, 1H), 6.76 (s, 2H), 3.52 (s, 3H), 2.25 (s, 3H). |
| I-E-7 | 369.1 | 2.74 | $^1$H NMR (500 MHz, DMSO-d6) δ 10.75 (s, 1H), 9.47 (dd, J = 4.8, 2.5 Hz, 1H), 8.40 (d, J = 2.5 Hz, 1H), 7.76-7.59 (m, 2H), 7.61-7.38 (m, 3H), 2.33 (s, 3H) |
| I-E-8 | 373.1 | 2.11 | $^1$H NMR (500 MHz, DMSO-d6) δ 10.53 (s, 1H), 9.49 (dd, J = 4.8, 2.5 Hz, 1H), 8.45 (d, J = 2.5 Hz, 1H), 7.76 (d, J = 1.9 Hz, 1H), 6.76 (s, 2H), 6.52 (d, J = 1.9 Hz, 1H), 3.66 (s, 3H), 2.25 (s, 3H). |
| I-E-9 | 416.1 | 1.98 | $^1$H NMR (500 MHz, DMSO-d6) δ 10.64 (s, 1H), 10.60 (s, 0H), 9.52 (dt, J = 4.8, 2.6 Hz, 1H), 8.89-8.78 (m, 1H), 6.75 (s, 2H), 6.00-5.74 (m, 1H), 4.28 (q, J = 2.9 Hz, 2H), 3.77 (dt, J = 10.8, 5.5 Hz, 2H), 2.30 (d, J = 5.9 Hz, 3H), 2.14 (d, J = 4.5 Hz, 3H). |
| I-E-10 | 359.1 | 2.19 | $^1$H NMR (500 MHz, DMSO-d6) δ 11.46 (s, 1H), 9.48 (dd, J = 4.8, 2.5 Hz, 1H), 8.77 (d, J = 2.5 Hz, 1H), 8.25 (dd, J = 2.4, 0.6 Hz, 1H), 8.12 (dd, J = 1.9, 0.6 Hz, 1H), 6.76 (s, 2H), 6.69 (dd, J = 2.4, 1.9 Hz, 1H), 2.41 (s, 3H). |
| I-E-11 | 370.0 | 1.85 | $^1$H NMR (500 MHz, DMSO-d6) δ 10.76 (s, 1H), 9.49 (dd, J = 4.7, 2.5 Hz, 1H), 9.37 (s, 1H), 9.06 (s, 2H), 8.36 (d, J = 2.5 Hz, 1H), 6.76 (s, 2H), 6.52 (s, 1H), 2.34 (s, 3H). |
| I-E-12 | 373.1 | 1.97 | $^1$H NMR (500 MHz, DMSO-d6) δ 10.66 (s, 1H), 9.51 (dd, J = 4.8, 2.5 Hz, 1H), 8.62 (d, J = 2.5 Hz, 1H), 8.12-8.02 (m, 1H), 7.75 (d, J = 0.8 Hz, 1H), 6.76 (s, 2H), 4.04 (s, 3H), 2.35 (s, 3H). |
| I-E-13 | 384.1 | 2.19 | $^1$H NMR (500 MHz, DMSO-d6) δ 10.86 (s, 1H), 9.51 (dd, J = 4.7, 2.5 Hz, 1H), 8.90 (d, J = 5.6 Hz, 1H), 8.60 (d, J = 2.5 Hz, 1H), 7.95-7.57 (m, 2H), 6.79 (s, 2H), 2.72 (s, 3H), 2.40 (s, 3H). |
| I-E-14 | 370.1 | 2.07 | $^1$H NMR (500 MHz, DMSO-d6) δ 10.86 (s, 1H), 9.50 (dd, J = 4.8, 2.5 Hz, 1H), 8.98-8.85 (m, 2H), 8.59 (d, J = 2.5 Hz, 1H), 7.77-7.65 (m, 2H), 6.87-6.67 (m, 2H), 2.38 (s, 3H). |
| I-E-15 | 392.0 | 2.19 | $^1$H NMR (500 MHz, DMSO-d6) δ 11.04 (s, 1H), 9.42-9.32 (m, 1H), 8.79 (s, 1H), 3.84 (s, 2H), 3.67 (s, 4H), 2.73 (s, 4H), 2.37 (s, 3H). |
| I-E-16 | 387.1 | 2.23 | $^1$H NMR (500 MHz, DMSO-d6) δ 10.50 (s, 1H), 9.49 (dd, J = 4.8, 2.5 Hz, 1H), 8.42 (d, J = 2.5 Hz, 1H), 6.76 (s, 2H), 6.28 (d, J = 0.6 Hz, 1H), 3.57 (s, 3H), 2.33 (s, 3H), 2.24 (s, 3H). |
| I-E-17 | 376.0 | 2.67 | $^1$H NMR (500 MHz, DMSO-d6) δ 10.85 (s, 1H), 9.90 (s, 1H), 9.57 (dd, J = 5.0, 2.5 Hz, 1H), 9.09-8.81 (m, 1H), 6.80 (s, 1H), 4.54 (d, J = 5.0 Hz, 1H), 3.63 (s, 1H), 3.29 (d, J = 15.4 Hz, 1H), 2.47 (s, 2H), 2.15 (s, 1H), 1.90 (d, J = 6.2 Hz, 1H). |
| I-E-18 | 387.2 | 2.02 | $^1$H NMR (500 MHz, DMSO-d6) δ 10.37 (s, 1H), 9.48 (dd, J = 4.8, 2.5 Hz, 1H), 8.48 (d, J = 2.5 Hz, 1H), 7.83 (s, 1H), 6.75 (s, 2H), 3.95 (s, 3H), 2.22 (s, 3H), 2.04 (s, 3H). |
| I-E-19 | 405.3 | 2.07 | $^1$H NMR (500 MHz, DMSO-d6) δ 11.05 (s, 1H), 9.55 (dd, J = 4.7, 2.5 Hz, 1H), 9.43 (s, 1H), 8.90-8.85 (m, 1H), 6.79 (s, 2H), 3.70 (s, 2H), 3.41 (d, J = 12.5 Hz, 2H), 3.05 (d, J = 12.8 Hz, 2H), 2.94 (d, J = 10.0 Hz, 2H), 2.75 (s, 3H), 2.44 (t, J = 11.5 Hz, 2H), 2.34 (s, 3H). |
| I-E-20 | 337.1 | 2.1 | $^1$H NMR (500 MHz, DMSO-d6) δ 11.19 (s, 1H), 9.51 (dd, J = 4.8, 2.5 Hz, 1H), 8.91 (dd, J = 2.6, 0.5 Hz, 1H), 6.75 (s, 2H), 4.62 (s, 2H), 3.54 (s, 3H), 2.30 (s, 3H). |
| I-E-21 | 362.1 | 2.74 | $^1$H NMR (500 MHz, DMSO-d6) δ 10.67 (s, 0H), 9.51 (dd, J = 4.8, 2.5 Hz, 0H), 8.92-8.80 (m, 0H), 3.26-3.07 (m, 1H), 2.33 (s, 1H), 2.12-1.99 (m, 1H). |

Example 10

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100

(Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 11

ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [γ-33P]ATP (3 mCi 33P ATP/mmol ATP, Perkin Elmer) and 800 µM target peptide (ASELPAS-QPQPFSAKKK (SEQ. ID NO: 1)).

Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µL 0.1M phosphoric acid containing 2 mM ATP. A multiscreen phosphocellulose filter 96-well plate (Millipore, Cat no. MAPHN0B50) was pretreated with 100 µL 0.2M phosphoric acid prior to the addition of 45 µL of the stopped assay mixture. The plate was washed with 5×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Table 6, below, shows the ATR Inhibition Ki values of compounds of the disclosure. Compounds with a Ki value of <0.01 µM are marked with "+++." Compounds with a Ki value >0.01 µM but <1 µM are marked with "++." Compounds with a Ki value >1 µM but <5 µM are marked with "+."

TABLE 6

| Cmpd. # | ATR Ki |
|---|---|
| I-A-1 | + |
| I-A-2 | ++ |
| I-A-3 | ++ |
| I-A-4 | ++ |
| I-A-5 | ++ |
| I-A-6 | + |
| I-A-7 | ------ |
| I-A-8 | ++ |
| I-A-9 | + |
| I-A-10 | ++ |
| I-A-11 | + |
| I-A-12 | ++ |
| I-A-13 | ++ |
| I-A-14 | ++ |
| I-A-15 | + |
| I-A-16 | + |
| I-A-17 | ++ |
| I-A-18 | + |
| I-A-19 | + |
| I-A-20 | + |
| I-B-1 | ++ |
| I-B-2 | ++ |
| I-B-3 | ++ |
| I-B-4 | ++ |
| I-B-5 | ++ |
| I-B-6 | ++ |
| I-B-7 | ++ |
| I-B-8 | ++ |
| I-B-9 | ++ |
| I-B-10 | ++ |
| I-B-11 | ++ |
| I-B-12 | ++ |
| I-B-13 | ++ |
| I-B-14 | ++ |
| I-B-15 | ++ |
| I-B-16 | + |
| I-B-17 | ------ |
| I-B-18 | ------ |

TABLE 6-continued

| Cmpd. # | ATR Ki |
|---|---|
| I-B-19 | ------ |
| I-B-20 | ++ |
| I-B-21 | ++ |
| I-B-22 | +++ |
| I-B-23 | ++ |
| I-B-24 | ++ |
| I-C-1 | ++ |
| I-C-2 | ++ |
| I-C-3 | ++ |
| I-C-4 | ++ |
| I-C-5 | ++ |
| I-C-6 | ++ |
| I-C-7 | ++ |
| I-C-8 | ++ |
| I-C-9 | ++ |
| I-C-10 | +++ |
| I-C-11 | ++ |
| I-D-1 | +++ |
| I-D-2 | ++ |
| I-D-3 | ++ |
| I-D-4 | ++ |
| I-D-5 | ++ |
| I-D-6 | ++ |
| I-E-1 | +++ |
| I-E-2 | ++ |
| I-E-3 | ++ |
| I-E-4 | +++ |
| I-E-5 | ++ |
| I-E-6 | ++ |
| I-E-7 | +++ |
| I-E-8 | ++ |
| I-E-9 | ++ |
| I-E-10 | +++ |
| I-E-11 | ++ |
| I-E-12 | ++ |
| I-E-13 | ++ |
| I-E-14 | ++ |
| I-E-15 | ++ |
| I-E-16 | ++ |
| I-E-17 | +++ |
| I-E-18 | ++ |
| I-E-19 | +++ |
| I-E-20 | ++ |
| I-E-21 | ++ |

Example 12

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

Table 7, below, shows the Cisplatin sensitization values of compounds of the disclosure. Compounds with a Cisplatin sensitization value of <0.02 µM are marked with "+++." Compounds with a Cisplatin sensitization value >0.02 µM but <0.2 µM are marked with "++." Compounds with a Cisplatin sensitization value >0.2 µM but <5 µM are marked with "+."

TABLE 7

| Cmpd. # | Cisplatin Sensitization Assay |
|---|---|
| I-A-1 | + |
| I-A-2 | + |
| I-A-3 | ++ |
| I-A-4 | ++ |
| I-A-5 | ++ |
| I-A-6 | ++ |
| I-A-7 | ------ |
| I-A-8 | +++ |
| I-A-9 | + |
| I-A-10 | + |
| I-A-11 | ++ |
| I-A-12 | ++ |
| I-A-13 | ++ |
| I-A-14 | ++ |
| I-A-15 | + |
| I-A-16 | + |
| I-A-17 | ++ |
| I-A-18 | + |
| I-A-19 | + |
| I-A-20 | + |
| I-B-1 | ++ |
| I-B-2 | ++ |
| I-B-3 | ++ |
| I-B-4 | +++ |
| I-B-5 | ++ |
| I-B-6 | +++ |
| I-B-7 | +++ |
| I-B-8 | ++ |
| I-B-9 | +++ |
| I-B-10 | ++ |
| I-B-11 | ++ |
| I-B-12 | ++ |
| I-B-13 | ++ |
| I-B-14 | +++ |
| I-B-15 | ++ |
| I-B-16 | ------ |
| I-B-17 | ------ |
| I-B-18 | ------ |
| I-B-19 | ------ |
| I-B-20 | +++ |
| I-B-21 | +++ |
| I-B-22 | +++ |
| I-B-23 | ++ |
| I-B-24 | ------ |
| I-C-1 | ++ |
| I-C-2 | ++ |
| I-C-3 | ++ |
| I-C-4 | ----- |
| I-C-5 | ++ |
| I-C-6 | ++ |
| I-C-7 | +++ |
| I-C-8 | +++ |
| I-C-9 | ++ |
| I-C-10 | +++ |
| I-C-11 | ++ |
| I-D-1 | +++ |
| I-D-2 | +++ |
| I-D-3 | +++ |
| I-D-4 | ++ |
| I-D-5 | ++ |
| I-D-6 | +++ |
| I-E-1 | +++ |
| I-E-2 | +++ |
| I-E-3 | +++ |
| I-E-4 | +++ |
| I-E-5 | +++ |
| I-E-6 | +++ |

TABLE 7-continued

| Cmpd. # | Cisplatin Sensitization Assay |
|---|---|
| I-E-7 | +++ |
| I-E-8 | +++ |
| I-E-9 | +++ |
| I-E-10 | +++ |
| I-E-11 | ++ |
| I-E-12 | ++ |
| I-E-13 | +++ |
| I-E-14 | +++ |
| I-E-15 | +++ |
| I-E-16 | +++ |
| I-E-17 | +++ |
| I-E-18 | +++ |
| I-E-19 | +++ |
| I-E-20 | +++ |
| I-E-21 | ++ |

Example 13

Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Example 14

ATR-Complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM $MgCl_2$ and 1 mM DTT. Final substrate concentrations were 10 μM [g-33P]ATP (3.5 μCi 33P ATP/nmol ATP, Perkin Elmer, Massachusetts, USA) and 800 μM target peptide (ASELPASQPQPFSAKKK (SEQ. ID NO: 1)), Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1(A891-S1105). An enzyme stock buffer solution was prepared containing all of the reagents listed above, with the exception of target peptide, ATP and the test compound of interest. This enzyme stock was pre-incubated for 30 minutes at 25° C. 8.5 μL of the enzyme stock solution was placed in a 96-well plate followed by addition of 5 μl of target peptide and 2 μL of DMSO stock containing serial dilutions of the test compound (typically starting from a final concentration of 1.5 μM with 2.5-fold serial dilutions) in duplicate (final DMSO concentration 7%). The plate was pre-incubated for 10 minutes at 25° C. and the reaction initiated by addition of 15 μL [g-33P]ATP (final concentration 10 μM).

The reaction was stopped after 20 hours by the addition of 30 μL 0.3 M phosphoric acid containing 2 mM ATP. A phosphocellulose filter 96-well plate (Multiscreen HTS MAPH-NOB50, Merck-Millipore, Massachusetts, USA) was pre-treated with 100 μL 0.1 M phosphoric acid prior to the addition of 45 μL of the stopped assay mixture. The plate was washed with 5×200 μL 0.1 M phosphoric acid. After drying, 50 μL Optiphase 'SuperMix' liquid scintillation cocktail (Perkin Elmer, Massachusetts, USA) was added to the well prior to scintillation counting (Wallac 1450 Microbeta Liquid Scintillation Counter, Perkin Elmer, Massachusetts, USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

Table 8, below, shows the ATR Inhibition Ki values of compounds of the disclosure. Compounds with a Ki value of <0.01 μM are marked with "+++." Compounds with a Ki value >0.01 μM but <1 μM are marked with "++." Compounds with a Ki value >1 μM but <5 μM are marked with "+."

TABLE 8

| Cmpd. # | ATR Ki |
|---|---|
| I-B-13 | +++ |
| I-C-1 | +++ |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:

1. A compound of formula I:

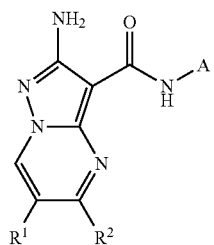

or a pharmaceutically acceptable salt thereof, wherein:

$R^1$ and $R^2$ are independently selected from H; halo; —C($J^1$)$_2$CN; —CN; W; or M; wherein at least one of $R^1$ and $R^2$ is not H;

$J^1$ is independently selected from H or $C_{1-2}$alkyl; or two occurrences of $J^1$, together with the carbon atom to which they are attached, form an 3-4 membered carbocyclic ring;

M is a $C_{1-8}$aliphatic wherein up to three methylene units are optionally replaced with —O—, —NR—, —C(O)—, or —S(O)$_z$—, each M is optionally substituted with 0-3 occurrences of $R^{2a}$;

$R^{2a}$ is independently selected from halo; —CF$_3$; —CN; a $C_{1-4}$aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur;

W is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein W is optionally substituted with 0-5 occurrences of $J^W$;

$J^W$ is independently selected from —CN, halo, —CF$_3$; a $C_{1-4}$aliphatic wherein up to two methylene units are optionally replaced with —O—, —NR—, —C(O)—, or —S(O)$_z$—; or a 3-6 membered non-aromatic ring having 0-2 heteroatoms selected from oxygen, nitrogen, or sulfur;

two occurrences of $J^W$ on the same atom, together with atom to which they are joined, form a 3-6 membered ring having 0-2 heteroatoms selected from oxygen, nitrogen, or sulfur; or two occurrences of $J^W$, together with W, form a 6-10 membered saturated or partially unsaturated bridged ring system;

A is independently selected from:

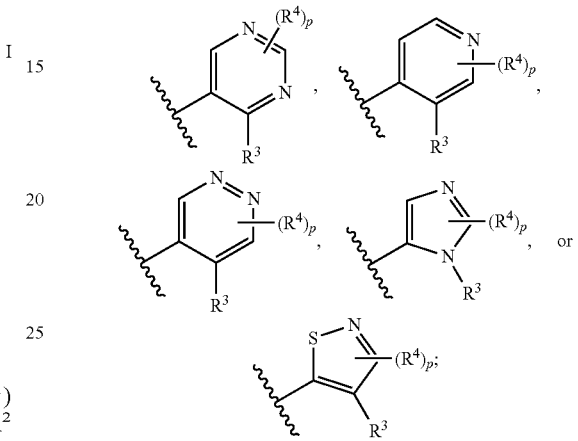

p is 0, 1, or 2;

$R^3$ is independently selected from -(L)$_n$-$Q^1$ or T;

L and T are each independently a $C_{1-10}$aliphatic chain wherein up to three methylene units of the aliphatic chain are optionally replaced with —O—, —NR—, —S(O)$_z$—, or —C(O)—; each L and T is independently substituted with 0-5 occurrences of $J^{LT}$;

$J^{LT}$ is independently selected from halo, —CN, or a $C_{1-4}$aliphatic chain wherein up to two methylene units of the aliphatic chain are optionally replaced with —O—, —NR—, —C(O)—, or —S(O)$_z$—;

n is 0 or 1;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur; wherein $Q^1$ is independently substituted with 0-5 occurrences of $J^Q$;

$J^Q$ is independently selected from halo; —CN; =O; $Q^2$; or a $C_{1-8}$aliphatic chain wherein up to three methylene units of the aliphatic chain are optionally replaced with —O—, —NR—, —C(O)—, or —S(O)$_z$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from oxygen, nitrogen, or sulfur; or a 7-12 membered fully saturated, partially unsaturated, or aromatic bicyclic ring having 0-5 heteroatoms selected from oxygen, nitrogen, or sulfur;

$J^R$ is independently selected from halo; —CN; =O; →O; $Q^3$; or a $C_{1-6}$ aliphatic chain wherein up to two methylene units of the aliphatic chain are optionally replaced with —O—, —NR—, —C(O)—, or —S(O)$_z$—; each $J^R$ is optionally substituted with 0-3 occurrences of $J^P$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; a 7-12 membered fully saturated, partially unsaturated, or aromatic bicyclic ring having 0-5 heteroatoms selected from oxygen, nitrogen, or sulfur;

$J^X$ is independently selected from halo or a $C_{1-4}$ aliphatic chain wherein up to two methylene units of the aliphatic chain are optionally replaced with —O—, —NR—, —C(O)—, or —S(O)$_z$—; or $J^P$ is independently selected from halo; —CN; =O; a $C_{1-6}$ aliphatic chain wherein up to two methylene units of the aliphatic chain are optionally replaced with —O—, —NR—, —C(O)—, or —S(O)$_z$—; or a 3-6 membered non-aromatic ring having 0-2 heteroatoms selected from oxygen, nitrogen, or sulfur; each $J^P$ is optionally substituted with 0-3 occurrences of $J^M$; or two occurrences of $J^P$ on the same atom, together with the atom to which they are joined, form a 3-6 membered ring having 0-2 heteroatoms selected from oxygen, nitrogen, or sulfur; or two occurrences of $J^P$, together with $Q^3$, form a 6-10 membered saturated or partially unsaturated bridged ring system;

$R^4$ is independently selected from H, halo, a $C_{3-4}$ membered cycloalkyl, 3-4 membered heterocyclyl, or $C_{1-4}$ aliphatic chain wherein up to two methylene units of the aliphatic chain are optionally replaced with —O—, —NR—, —C(O)—, or —S(O)$_z$—;

$J^M$ is independently selected from halo or $C_{1-6}$ aliphatic;

z is 0, 1, or 2; and

R is independently selected from H or $C_{1-4}$ aliphatic.

2. The compound of claim 1, wherein $R^1$ is fluoro.

3. The compound of claim 1, wherein $R^1$ is —CH$_2$CN or —CH(C$_{1-2}$alkyl)CN.

4. The compound of claim 1, wherein $R^1$ is chloro.

5. The compound of claim 1, wherein $R^1$ is H.

6. The compound of claim 5, wherein $R^2$ is —CF$_3$.

7. The compound of claim 5, wherein $R^2$ is $C_{1-6}$ aliphatic wherein up to two methylene units are optionally replaced with —O—, —NR—, —C(O)—, or S.

8. The compound of claim 7, wherein $R^2$ is —O(C$_{1-3}$alkyl)N(C$_{1-3}$alkyl) or —NR(C$_{1-3}$alkyl)N(C$_{1-3}$alkyl).

9. The compound of claim 1, wherein $R^2$ is H.

10. The compound of claim 1, wherein Ring A is:

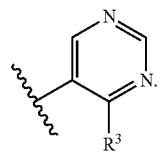

11. The compound of claim 1, wherein Ring A is:

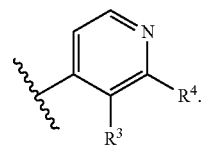

12. The compound of claim 1, wherein Ring A is:

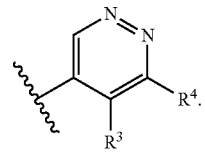

13. The compound of claim 1, wherein $R^3$ is -(L)$_n$-$Q^1$.

14. The compound of claim 13, wherein n is 1.

15. The compound of claim 14, wherein L is —O—.

16. The compound of claim 13, wherein n is 0.

17. The compound of claim 13, wherein $Q^1$ is independently selected from a 3-7 membered fully saturated, partially unsaturated, or aromatic monocyclic ring having 0-3 heteroatoms selected from oxygen, nitrogen or sulfur.

18. The compound of claim 17, wherein $Q^1$ is a 3-7 membered heterocyclyl or carbocyclyl.

19. The compound of claim 18, wherein $Q^1$ is independently selected from cyclopropyl, cyclobutyl, cyclopentyl, cyclohexyl, cycloheptyl, pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, and azetidinyl.

20. The compound of claim 19, wherein $Q^1$ is independently selected from pyrrolidinyl, cyclopropyl, cyclohexyl, piperidinyl or piperazinyl.

21. The compound of claim 17, wherein $Q^1$ is a 5-6 membered aryl or heteroaryl.

22. The compound of claim 21, wherein $Q^1$ is independently selected from phenyl, pyridinyl, pyrazinyl, pyrimidinyl, tetrahydropyridinyl, pyrrolyl, imidazolyl, pyrazolyl, 1,2,3-triazolyl, or 1,2,4-triazolyl.

23. The compound of claim 22, wherein $Q^1$ is pyridinyl.

24. The compound of claim 13, wherein $Q^1$ is a 7-12 membered fully saturated, partially unsaturated, or aromatic bicyclic ring having 1-5 heteroatoms selected from oxygen, nitrogen, or sulfur.

25. The compound of claim 24, wherein $Q^1$ is independently selected from octahydropyrrolo[1,2-a]pyrazinyl, 5,6,7,8-tetrahydroimidazo[1,2-a]pyridinyl, octahydro-1H-pyrazino[1,2-a]pyrazinyl, 5,6,7,8-tetrahydroimidazo[1,5-a]

pyrazinyl, 2,5-diazabicyclo[4.1.0]heptane, or octahydropyrazino[2,1-c][1,4]oxazinyl.

26. The compound of claim 13, wherein $J^Q$ is $C_{1-6}$aliphatic chain wherein up to three methylene units of the aliphatic chain are optionally replaced with —O—, —NR—, or —C(O)—.

27. The compound of claim 26, wherein $J^Q$ is independently selected from —C(O)—, $C_{1-4}$ alkyl, —(C$_{0-4}$alkyl)NH$_2$, —(C$_{0-4}$ alkyl)NH(C$_{1-4}$ alkyl), —(C$_{0-4}$ alkyl)N(C$_{1-4}$ alkyl)$_2$, —(C$_{0-4}$alkyl)OH, —(C$_{0-4}$alkyl)O(C$_{1-4}$alkyl), —C(O)OH, —C(O)O(C$_{1-4}$alkyl), N(C$_{1-4}$alkyl)$_2$, —C(O)N(C$_{1-4}$ alkyl)$_2$, or —(C$_{1-3}$ alkyl)O(C$_{1-2}$ alkyl)N(C$_{1-3}$ alkyl)$_2$.

28. The compound of claim 27, wherein $J^Q$ is independently selected from —C(O)—, $C_{1-4}$ alkyl, or —(C$_{0-4}$alkyl)NH$_2$.

29. The compound of claim 13, wherein $J^Q$ is $Q^2$.

30. The compound of claim 29, wherein $Q^2$ is a 3-7 membered fully saturated, partially unsaturated, or aromatic monocyclic ring having 0-3 heteroatoms selected from oxygen, sulfur, or nitrogen.

31. The compound of claim 30, wherein $Q^2$ is independently selected from selected from cyclopropyl, cyclobutyl, cyclopentyl, cyclohexyl, oxetanyl, tetrahydropyranyl, tetrahydrofuranyl, azetidinyl, pyrrolidinyl, piperidinyl, piperazinyl, thiomorpholinyl, or morpholinyl.

32. The compound of claim 31, wherein $Q^2$ is oxetanyl, pyrrolidinyl, tetrahydrofuranyl, or tetrahydropyranyl.

33. The compound of claim 29, wherein $Q^2$ is an 7-12 membered fully saturated, partially unsaturated, or aromatic bicyclic ring having 0-5 heteroatoms selected from oxygen, nitrogen, or sulfur.

34. The compound of claim 18, wherein $Q^2$ is independently selected from 5,6,7,8-tetrahydroimidazo[1,5-a]pyrazinyl or 5,6,7,8-tetrahydroimidazo[1,2-a]pyrazinyl.

35. The compound of claim 18, wherein two occurrences of $J^Q$, together with $Q^1$, form a bridged ring system.

36. The compound of claim 18, wherein $J^Q$ is =O, halo, or →O.

37. The compound of claim 18, wherein two occurrences of $J^Q$ on the same atom, taken together with the atom to which they are joined, form a 3-6 membered non-aromatic ring having 0-2 heteroatoms selected from oxygen, nitrogen, or sulfur.

38. The compound of claim 37, wherein the ring formed by the two occurrences of $J^Q$ on the same atom, taken together with the atom to which they are joined, is selected from oxetanyl, cyclobutyl, or azetidinyl.

39. The compound of claim 13, wherein $J^R$ is a 3-6 membered heterocyclyl having 1-3 heteroatoms selected from oxygen, nitrogen, or sulfur.

40. The compound of claim 39, wherein $J^R$ is independently selected from oxetanyl, piperidinyl, azetidinyl, piperazinyl, pyrrolidinyl, 1,4-diazepanyl, or morpholinyl.

41. The compound of claim 40, wherein $J^R$ is a piperazinyl.

42. The compound of claim 13, wherein $J^R$ is independently selected from halo, =O, —OH, $C_{1-4}$alkyl, —(C$_{0-4}$alkyl)N(C$_{1-4}$alkyl)$_2$, or —(C$_{0-4}$alkyl)O(C$_{1-4}$alkyl).

43. The compound of claim 30, wherein two occurrences of $J^R$ on the same atom, together with the atom to which they are joined, form a 3-6 membered aromatic or non-aromatic ring having 0-2 heteroatoms selected from oxygen, nitrogen, or sulfur.

44. The compound of claim 39, wherein $J^P$ is halo, —C$_{1-4}$alkyl, or a 3-6 membered non-aromatic ring having 0-2 heteroatoms selected from oxygen, nitrogen, or sulfur.

45. The compound of claim 44, wherein $J^P$ is selected from pyrrolidinyl or oxetanyl.

46. The compound of claim 1, wherein $R^3$ is T.

47. The compound of claim 46, wherein T is independently selected from —(C$_{1-4}$alkyl), —(C$_{1-4}$alkyl)N(C$_{1-4}$alkyl)$_2$, —(C$_{1-3}$alkyl)O(C$_{1-2}$alkyl)N(C$_{1-3}$alkyl)$_2$, —(C$_{1-4}$alkyl)OH, —(C$_{1-4}$alkyl)NH$_2$, or —(C$_{1-4}$alkyl)O(C$_{1-4}$alkyl).

48. The compound of claim 47, wherein $J^{LT}$ is halo or $C_{1-3}$alkyl.

49. The compound of claim 1, wherein A is independently selected from:

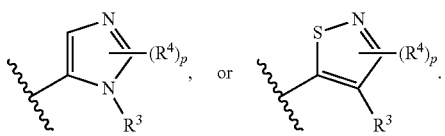

50. The compound of claim 49, wherein p is 0.

51. The compound of claim 49, wherein p is 1.

52. The compound of claim 51, wherein $R^4$ is independently selected from $C^{1-4}$alkyl or halo.

53. The compound of claim 51, wherein $R^4$ is independently selected from methyl or fluoro.

54. The compound of claim 49, wherein $R^3$ is -(L)$_n$-$Q^1$.

55. The compound of claim 54, wherein n is 0.

56. The compound of claim 54, wherein n is 1.

57. The compound of claim 56, wherein L is independently selected from $C_{1-4}$alkyl.

58. The compound of claim 54, wherein $Q^1$ is phenyl.

59. The compound of claim 54, wherein $Q^1$ is independently selected from a 3-6 membered carbocyclyl or a 4-6 membered heterocyclyl.

60. The compound of claim 59, wherein $Q^1$ is independently selected from cyclopropyl, morpholinyl, pyrrolidinyl, piperidinyl, piperazinyl, tetrahydropyran, dihydropyran, or tetrahydropyridine.

61. The compound of claim 54, wherein $Q^1$ is a 5-6 membered heteroaryl.

62. The compound of claim 61, wherein $Q^1$ is independently selected from pyrazolyl, pyridinyl, or pyrimidinyl.

63. The compound of claim 54, wherein $J^Q$ is independently selected from a $C_{1-6}$aliphatic chain wherein up to three methylene units of the aliphatic chain are optionally replaced with —O—, —NR—, or —C(O)—.

64. The compound of claim 63, wherein $J^Q$ is independently selected from —C(O)—, —C(O)C$_{1-4}$alkyl or $C_{1-4}$alkyl.

65. The compound of claim 64, wherein $J^Q$ is methyl.

66. The compound of claim 64, wherein $J^R$ is independently selected from piperidinyl or piperazinyl.

67. The compound of claim 66, wherein $J^P$ is independently selected from oxetanyl or azetidinyl.

68. The compound of claim 49, wherein $R^3$ is T.

69. The compound of claim 68, wherein T is a $C_{1-6}$aliphatic chain wherein up to three methylene units of the aliphatic chain are optionally replaced with —O—, —NR—, or —C(O)—.

70. The compound of claim 69, wherein T is —(C$_{1-3}$alkyl)O(C$_{1-3}$alkyl).

71. The compound of claim 1 independently selected from:
I-A-1
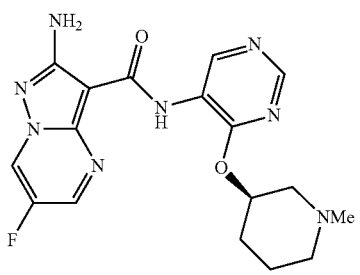
I-A-2
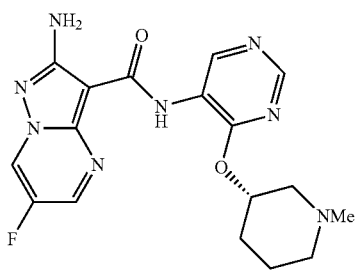
I-A-3
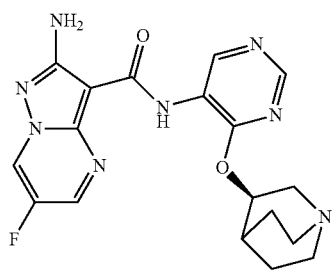
I-A-4
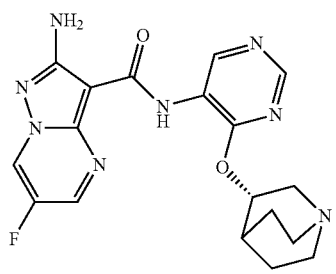
I-A-5
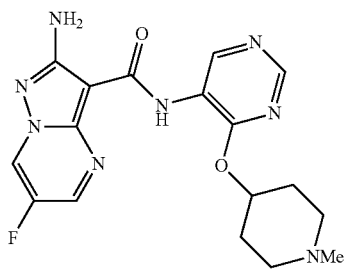
-continued
I-A-6
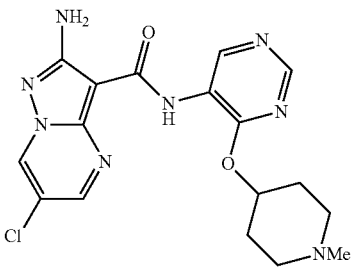
I-A-7
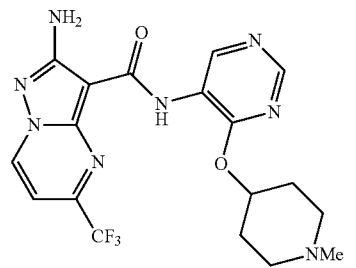
I-A-8
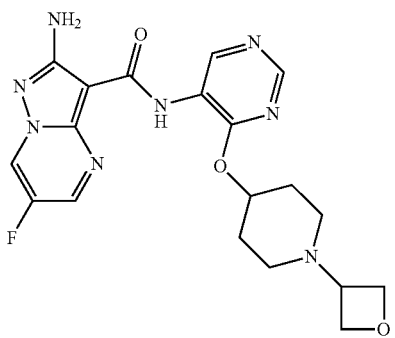
I-A-9
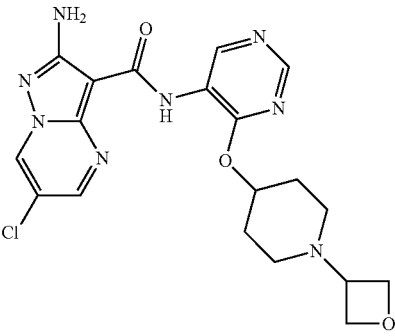
I-A-10
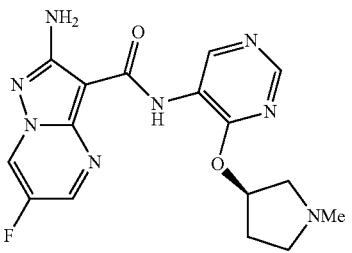

I-A-11
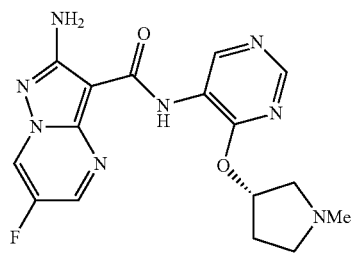
I-A-12
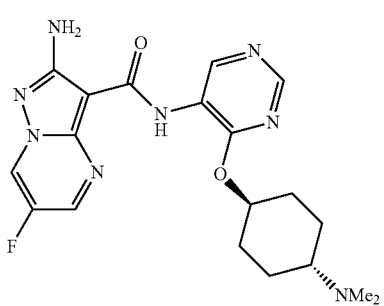
I-A-13
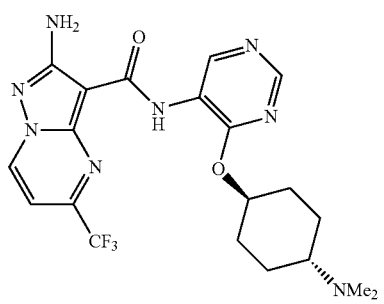
I-A-14
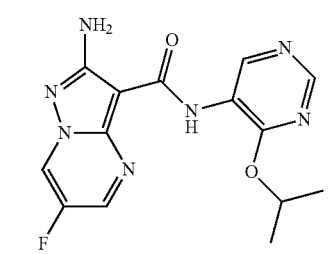
I-A-15
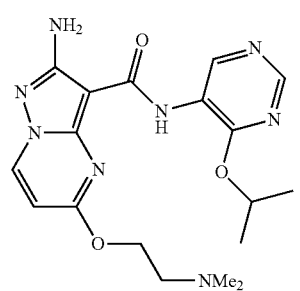
I-A-16
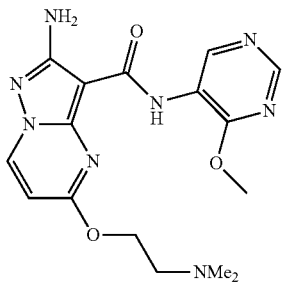
I-A-17
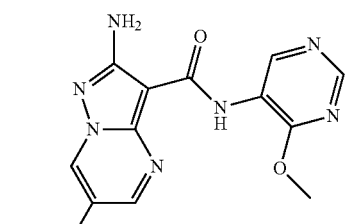
I-A-18
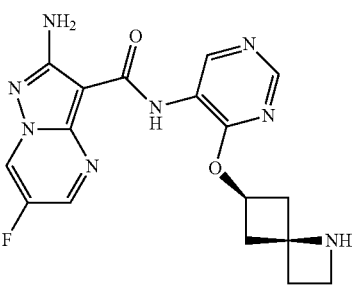
I-A-19
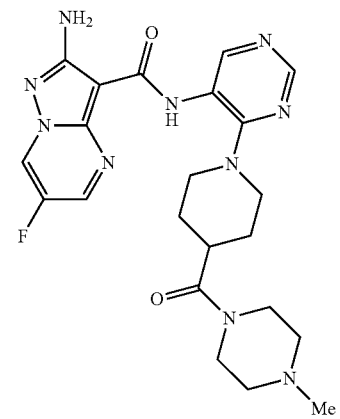
I-A-20
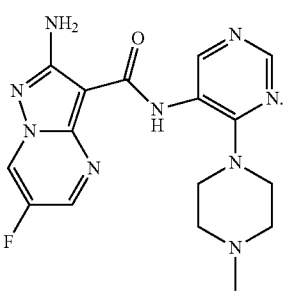

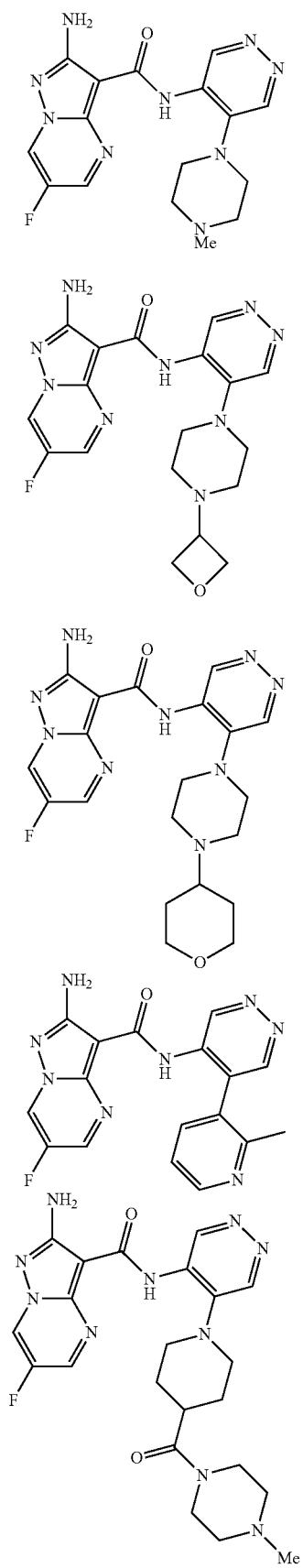
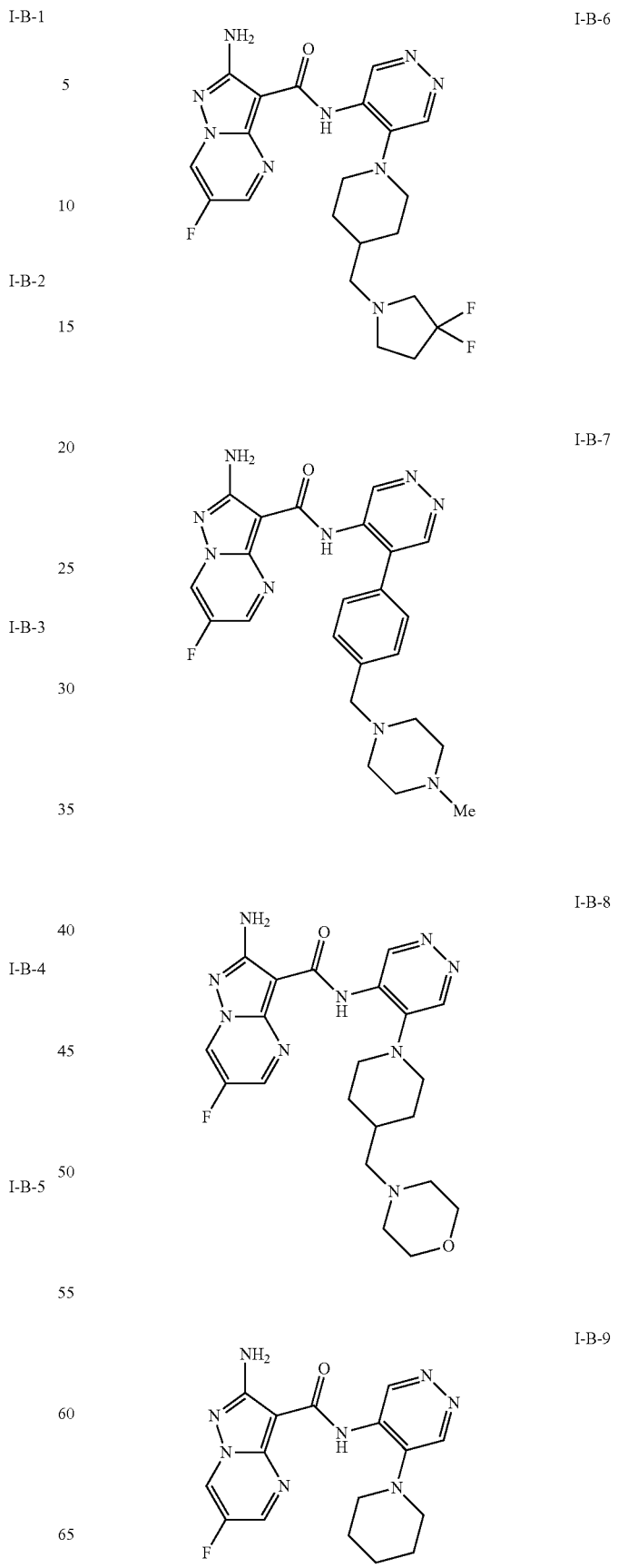

I-B-10
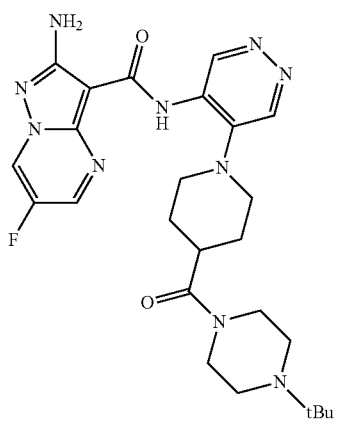
I-B-11
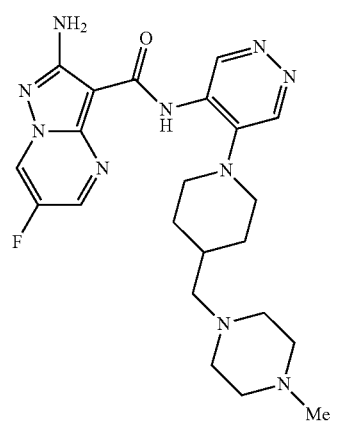
I-B-12
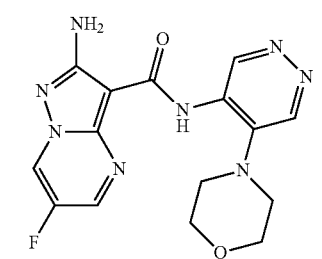
I-B-13
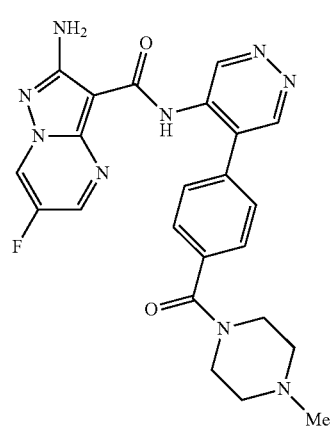
I-B-14
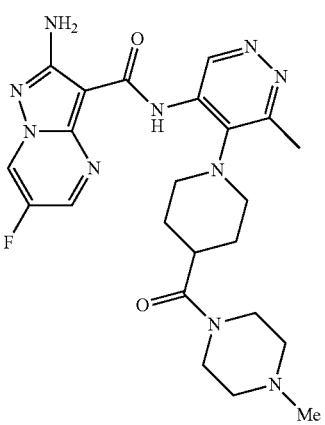
I-B-15
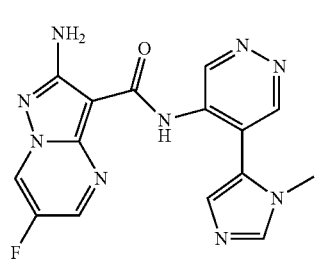
I-B-16
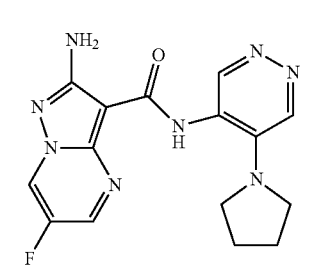
I-B-17
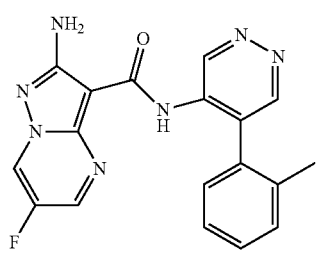
I-B-18
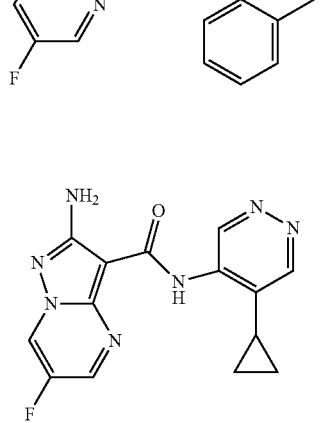

I-B-19
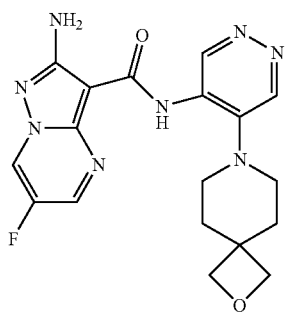
I-B-20
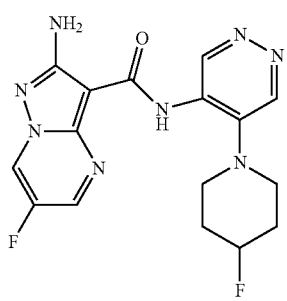
I-B-21
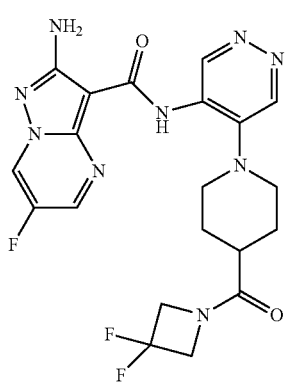
I-B-22
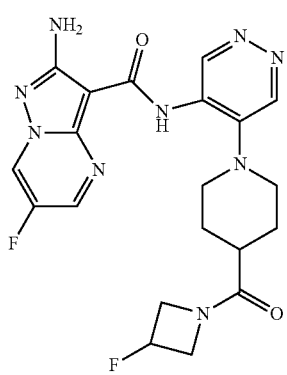
I-B-23
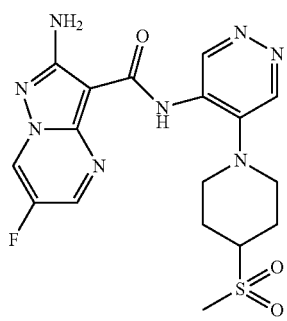
I-B-24
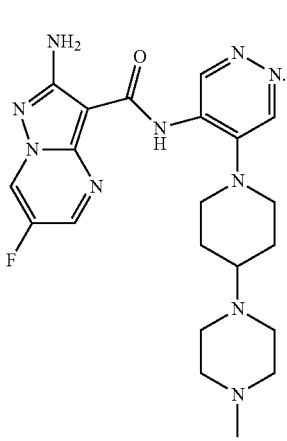
I-C-1
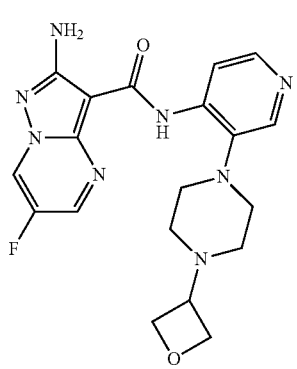
I-C-2
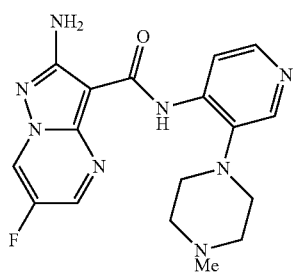

-continued

I-C-3

I-C-4

I-C-5

I-C-6

I-C-7

-continued

I-C-8

I-C-9

I-C-10

I-C-11

-continued
I-D-1
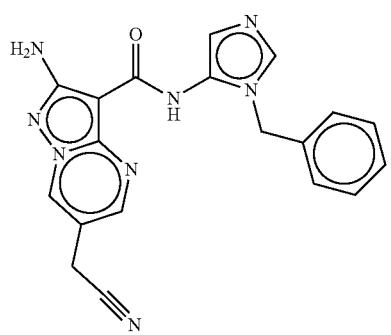
I-D-2
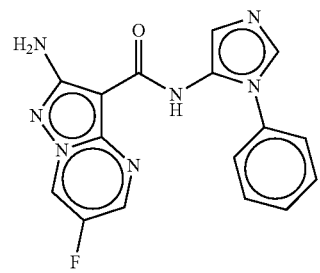
I-D-3
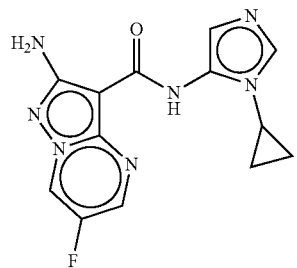
I-D-4
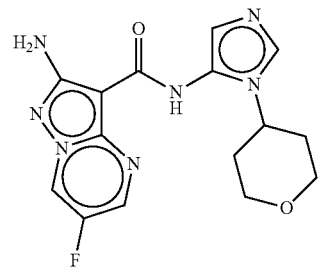
I-D-5
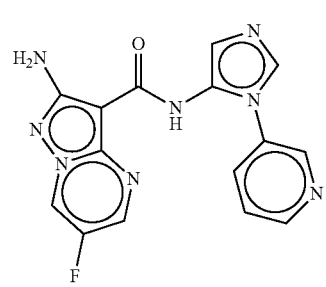
-continued
I-D-6
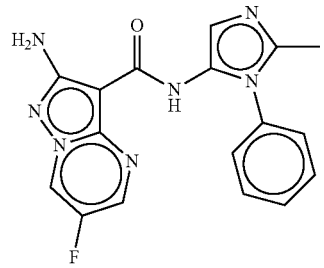
I-E-1
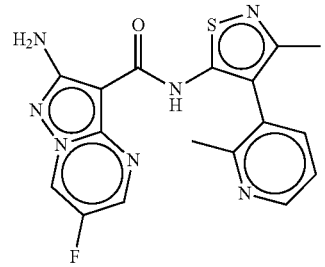
I-E-2
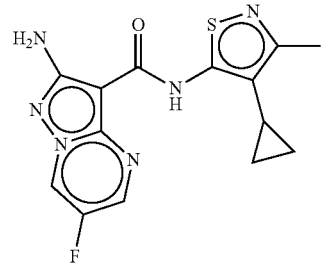
I-E-3
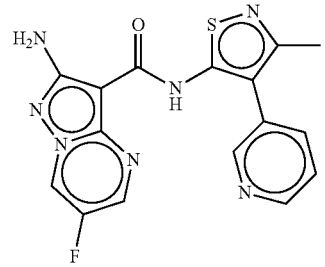
I-E-4
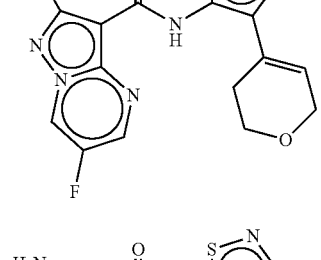
I-E-5
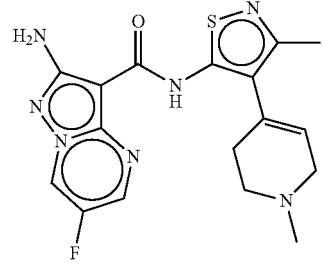

| | |
|---|---|
| I-E-6 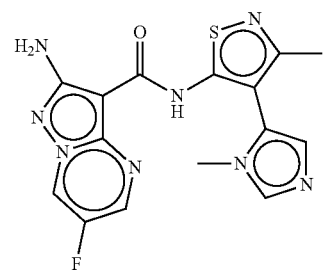 | I-E-11 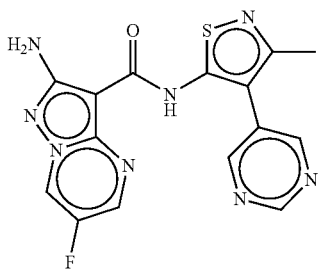 |
| I-E-7 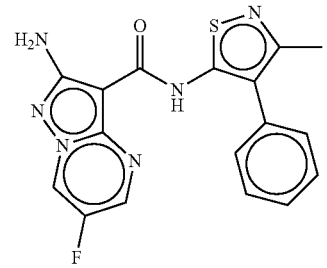 | I-E-12 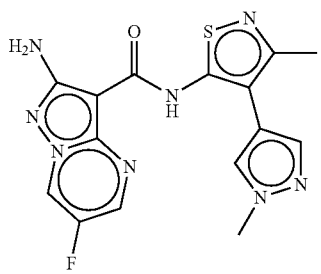 |
| I-E-8 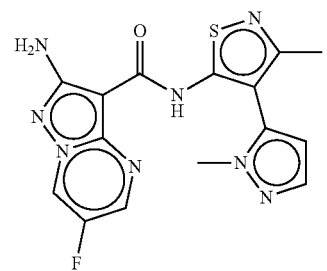 | I-E-13 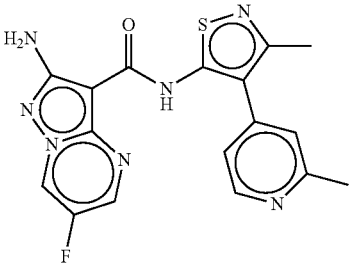 |
| I-E-9 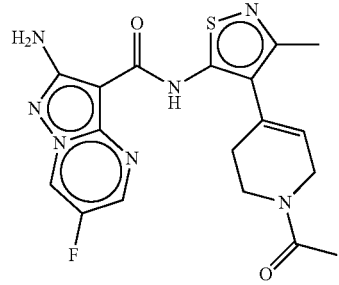 | I-E-14 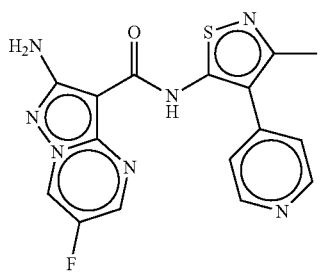 |
| I-E-10 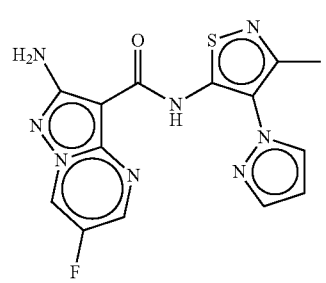 | I-E-15 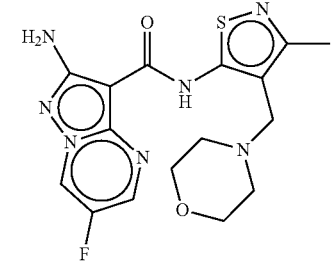 |
| | I-E-16 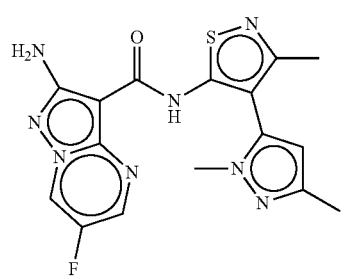 |

133
-continued

I-E-17
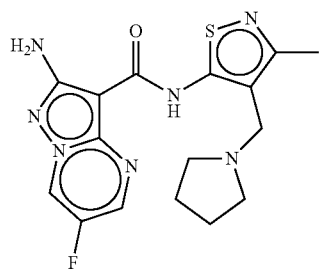

I-E-18
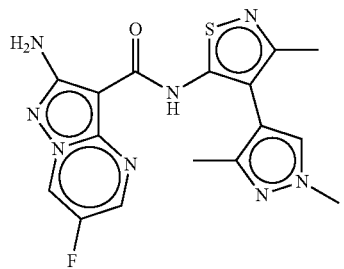

I-E-19
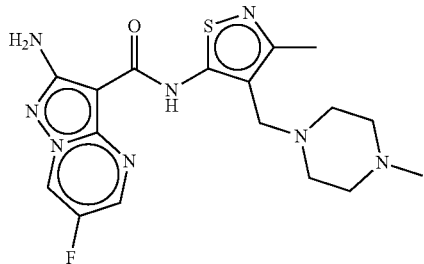

I-E-20
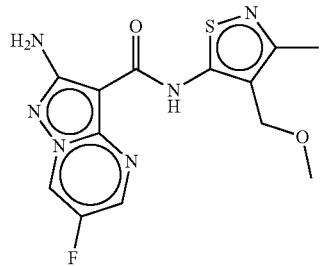

I-E-21
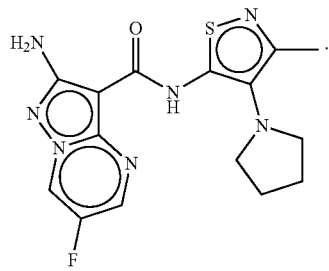

72. A pharmaceutical composition comprising a compound of claim 1 and a pharmaceutically acceptable carrier.

134

73. A process for preparing a compound of formula I:

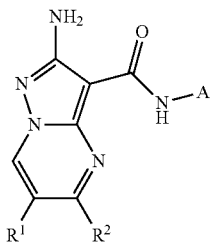

I comprising reacting a compound of formula 6:

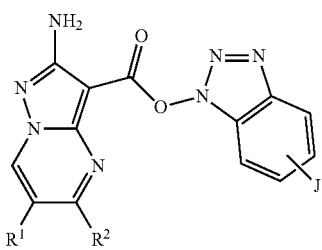

6 under suitable conditions to form an amide bond, wherein:
J is H or Cl;
$R^1$, $R^2$, and A are as defined in claim 1; and
the suitable conditions for forming the amide bond comprises reacting the compound of formula 6 with a substituted heteroaromatic amine in an aprotic solvent under heat.

74. The process of claim 73, further comprising the step of preparing a compound of formula 6:

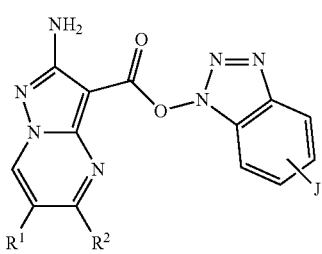

6 by reacting a compound of formula 5:

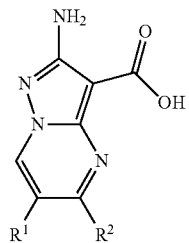

5 under suitable conditions to form an activated ester, wherein the suitable conditions for forming the activated ester comprises reacting the compound of formula 5 with an amide coupling agent in the presence of an organic base.

75. A process for preparing a compound of formula I:

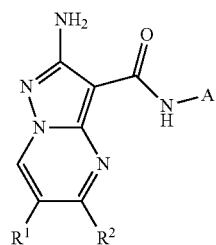

I comprising reacting a compound of formula 5:

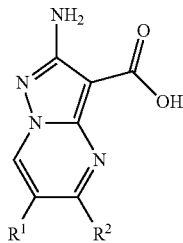

5 under suitable conditions to form an amide bond, wherein $R^1$, $R^2$, and A are as defined in claim 1 and the suitable conditions for forming the amide bond comprises reacting the compound of formula 5 with a substituted heteroaromatic amine in an aprotic solvent under heat.

76. The process of any one of claims 73-75, further comprising the step of preparing a compound of formula 5:

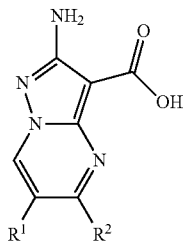

5 by reacting a compound of formula 4:

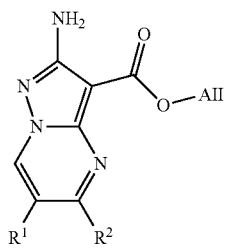

4 under suitable hydrolysis conditions, wherein the suitable hydrolysis conditions comprise reacting the compound of formula 4 with a silane in the presence of a metal catalyst.

77. The process of claim 76, further comprising the step of preparing a compound of formula 4:

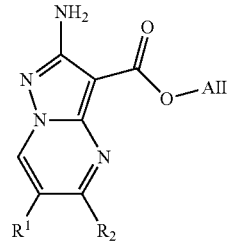

4 by reacting a compound of formula 3:

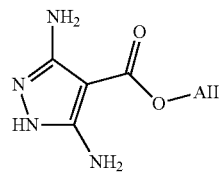

3 under suitable condensation conditions to form a pyrimidine ring, wherein the suitable condensation conditions for forming the pyrimidine ring comprises reacting a compound of formula 3 with a 1,3-dielectrophilic species in the presence of a solvent.

78. The process of claim 77, further comprising the step of preparing the compound of formula 3:

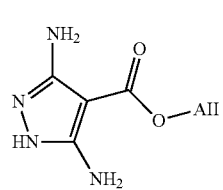

3 by reacting a compound of formula 2:

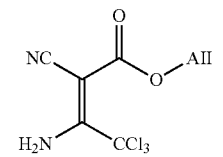

2 under suitable condensation conditions to form a pyrazole ring, wherein the suitable condensation conditions to form the pyrazole ring comprises reacting the compound of formula 2 with a hydrazine or hydrazine hydrate in the presence of an aprotic solvent under basic conditions.

79. The process of claim 78, further comprising the step of preparing a compound of formula 2:

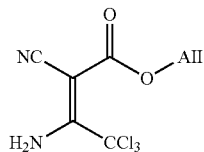

by reacting a compound of formula 1:

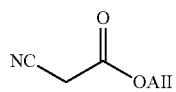

under suitable anion condensation conditions, wherein the suitable anion condensation conditions comprises:
1) reacting the compound of formula 1 with a base, in the presence of a solvent, to generate the anion of the compound of formula 1; and
2) reacting the anion of the compound of formula 1 with trichloroacetonitrile.

80. A process for preparing a compound of formula I:

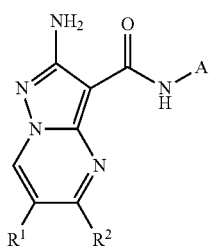

comprising reacting a compound of formula 9:

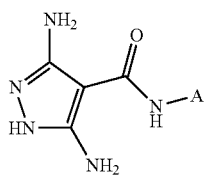

under suitable condensation conditions to form a pyrimidine ring, wherein $R^1$, $R^2$, and A are as defined in claim 1, and the suitable condensation conditions for forming the pyrimidine ring comprises reacting the compound of formula 9 with a 1,3-dielectrophilic species in the presence of a solvent.

81. The process of claim 78, further comprising the step of preparing a compound of formula 9:

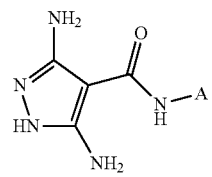

by reacting a compound of formula 8:

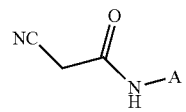

under suitable condensation conditions to form a pyrazole ring, wherein the suitable condensation conditions to form the pyrazole ring comprises:
1) reacting the compound of formula 8 with a base, in the presence of a solvent to generate the anion of formula 8;
2) reacting the anion with trichloroacetonitrile; and
3) reacting the product from 2) with a hydrazine or hydrazine hydrate in the presence of an aprotic solvent.

82. The process of claim 79, further comprising the step of preparing a compound of formula 8:

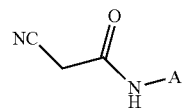

by reacting a compound of formula 7:

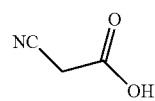

under suitable conditions to form an amide bond, wherein the suitable conditions for forming the amide bond comprises reacting the compound of formula 7 with a substituted heteroaromatic amine with an amide coupling agent in the presence of an aprotic solvent and an organic base.

* * * * *